US011643691B2

(12) United States Patent
Hanks et al.

(10) Patent No.: US 11,643,691 B2
(45) Date of Patent: May 9, 2023

(54) PREDICTIVE BIOMARKERS FOR CANCER IMMUNOTHERAPY AND METHODS OF USING SAME

(71) Applicant: Duke University, Durham, NC (US)

(72) Inventors: Brent Hanks, Durham, NC (US); Nicholas Devito, Durham, NC (US); Balamayooran Theivanthiran, Durham, NC (US); Fei Zhao, Durham, NC (US)

(73) Assignee: Duke University, Durham, NC (US)

( * ) Notice: Subject to any disclaimer, the term of this patent is extended or adjusted under 35 U.S.C. 154(b) by 329 days.

(21) Appl. No.: 16/384,710

(22) Filed: Apr. 15, 2019

(65) Prior Publication Data
US 2019/0316208 A1   Oct. 17, 2019

Related U.S. Application Data

(60) Provisional application No. 62/657,132, filed on Apr. 13, 2018.

(51) Int. Cl.
| *A61P 35/00* | (2006.01) |
| *C12Q 1/6886* | (2018.01) |
| *C07K 16/28* | (2006.01) |

(52) U.S. Cl.
CPC ............ *C12Q 1/6886* (2013.01); *A61P 35/00* (2018.01); *C07K 16/2818* (2013.01); *C12Q 2600/106* (2013.01); *C12Q 2600/158* (2013.01)

(58) Field of Classification Search
CPC .............. A61P 35/00; C12N 2501/415; C07K 16/2818; C12Q 1/6886; C12Q 2600/106; C12Q 2600/158
See application file for complete search history.

(56) References Cited

U.S. PATENT DOCUMENTS

| 7,723,477 B2 | 5/2010 | Gurney |
| 7,982,013 B2 | 7/2011 | Gurney |
| 8,324,361 B2 | 12/2012 | Gurney |
| 8,975,044 B2 | 3/2015 | Gurney |
| 9,573,998 B2 | 2/2017 | Gurney |

FOREIGN PATENT DOCUMENTS

WO   2017161188   3/2017

OTHER PUBLICATIONS

Lee et al. Molecules, 2019, 24: 1190 (Year: 2019).*
Robert et al. N Engl J Med 2015, 372: 2521-32 (Year: 2015).*
Holtzhausen et al. Cancer Immunology Research, 2015, 3(9): 1082-1095; with supp data (Year: 2015).*
Gebhardt et al. Clinical Cancer Research, 2015, 21(24): 5453-5459 (Year: 2015).*
Alsaab et al., "PD-1 and PD-L1 Checkpoint Signaling Inhibition for Cancer Immunotherapy: Mechanism, Combinations, and Clinical Outcome", Frontiers in Pharmacology, vol. 8, p. 561 (2017).
Arqués, O., et al. "Tankyrase inhibition blocks Wnt/ß-catenin pathway and reverts resistance to PI3K and AKT inhibitors in the treatment of colorectal cancer." Clinical cancer research 22.3 (2016): 644-656.6 XAV.
Banchereau, et al., (1998). Dendritic cells and the control of immunity. Nature 392, 245-252.
Bhamra, I., et al. "Novel porcupine (PORCN) inhibitor RXC004: Evaluation in models of RNF43 loss of function cancers." (2017): e14094-e14094.
Blumenthal, A., et al. "The Wingless homolog WNT5A and its receptor Frizzled-5 regulate inflammatory responses of human mononuclear cells induced by microbial stimulation." Blood 108.3 (2006): 965-973.
Chen X, et al: MicroRNA-374a Inhibits Aggressive Tumor Biological Behavior in Bladder Carcinoma by Suppressing Wnt/ß-Catenin Signaling. Cell Physiol Biochem 2018;48:815-826.
Clark, C. A., et al. "Tumor-intrinsic PD-L1 signals regulate cell growth, pathogenesis, and autophagy in ovarian cancer and melanoma." Cancer research 76.23 (2016): 6964-6974.
Collier, et al., (1993). Effect of fatty acid oxidation inhibition on glucose metabolism in diabetic rats. Horm Metab Res. 25, 9-12.
Dankort, D., et al. "Braf V600E cooperates with Pten loss to induce metastatic melanoma." Nature genetics 41.5 (2009): 544-552.
Emami, K. H., et al. "A small molecule inhibitor of ß-catenin/cyclic AMP response element-binding protein transcription." Proceedings of the National Academy of Sciences 101.34 (2004): 12682-12687.
Everts, et al., (2014). TLRdriven early glycolytic reprogramming via the kinases TBK1-IKK 3 supports the anabolic demands of dendritic cell activation. Nat. Immunol. 15, 323-332.
Fallarino, et al., (2006). The combined effects of tryptophan starvation and tryptophan catabolites down-regulate T cell receptor zeta-chain and induce a regulatory phenotype in naïve T cells. J. Immunol. 176, 6752-6761.
Fujigaki, H. et al. "Posttranslational modification of indoleamine 2, 3-dioxygenase." Analytical and bioanalytical chemistry 403.7 (2012): 1777-1782.
Fujii, N., et al. "An antagonist of dishevelled protein-protein interaction suppresses ß-catenin-dependent tumor cell growth." Cancer research 67.2 (2007): 573-579.
Gabrilovich, (2004). Mechanisms and functional significance of tumourinduced dendritic-cell defects. Nat. Rev. Immunol. 4, 941-952.
Gato-Cañas, M., et al. "PDL1 signals through conserved sequence motifs to overcome interferon-mediated cytotoxicity." Cell reports 20.8 (2017): 1818-1829.
Ghouri, Y. A., et al. "Review of hepatocellular carcinoma: Epidemiology, etiology, and carcinogenesis." Journal of carcinogenesis 16 (2017).
Handschin, et al., (2005). Nutritional regulation of hepatic heme biosynthesis and porphyria through PGC-1alpha. Cell 122, 505-515.

(Continued)

*Primary Examiner* — Meera Natarajan
(74) *Attorney, Agent, or Firm* — Quarles & Brady, LLP

(57) ABSTRACT

The present disclosure provides methods of detecting a wnt-β-catenin-mediated cancer and an immunotherapy resistant cancer by detecting the presence of an associated biomarker. Further, methods of threating the wnt-β-catenin-mediated cancer or immunotherapy resistant cancer are provided.

17 Claims, 41 Drawing Sheets
(35 of 41 Drawing Sheet(s) Filed in Color)
Specification includes a Sequence Listing.

(56) References Cited

OTHER PUBLICATIONS

Hanks, B.A. How to Integrate Immunotherapy into Your Clinical Practice. The Immune System and Cancer: Mechanisms of Immune Suppression. (2017) ASCO-SITC Joint Conference. Chicago, IL. Oral Presentation. Jun. 2, 2017.
Hanks, B.A., et al. "Targeting the Wnt5a-ß-catenin pathway in the melanoma microenvironment to augment checkpoint inhibitor immunotherapy." (2015): 3054-3054.
Hanks, et al., (2013). Type III TGF-b receptor downregulation generates an immunotolerant tumor microenvironment. J. Clin. Invest. 123, 3925-3940.
Herber, et al., (2010). Lipid accumulation and dendritic cell dysfunction in cancer. Nat. Med. 16, 880-886.
Holtzhausen, A., et al. "Early carcinogenesis involves the establishment of immune privilege via intrinsic and extrinsic regulation of indoleamine 2, 3-dioxygenase-1: translational implications in cancer immunotherapy." Frontiers in immunology 5 (2014): 438.
Holtzhausen, et al., (2015). Melanoma-derived Wnt5a promotes local dendriticcell expression of IDO and immunotolerance: opportunities for pharmacologic enhancement of immunotherapy. Cancer Immunol. Res. 3, 1082-1095.
Hossain, et al., (2015). Inhibition of fatty acid oxidation modulates immunosuppressive functions of myeloid-derived suppressor cells and enhances cancer therapies. Cancer Immunol. Res. 3, 1236-1247.
Hryhorenko, et al., (1998). Characterization of endogenous protoporphyrin IX induced by delta-aminolevulinic acid in resting and activated peripheral blood lymphocytes by four-color flow cytometry. Photochem. Photobiol. 67, 565-572.
Huang, S.-M. A., et al. "Tankyrase inhibition stabilizes axin and antagonizes Wnt signalling." Nature 461.7264 (2009): 614-620.
Hugo, et al., (2016). Genomic and Transcriptomic Features of Response to Anti-PD-1 Therapy in Metastatic Melanoma. Cell 165(1): 35-44. Author manuscript via Pubmed Central.
Inaba, et al., (1992). Generation of large numbers of dendritic cells from mouse bone marrow cultures supplemented with granulocyte/macrophage colony-stimulating factor. J. Exp. Med. 176, 1693-1702.
Jansson, et al., (2005). The Wnt/beta-catenin signaling pathway targets PPARgamma activity in colon cancer cells. Proc. Natl. Acad. Sci. USA 102, 1460-1465.
Jiang, et al., (2007). Disruption of E-cadherin—mediated adhesion induces a functionally distinct pathway of dendritic cell maturation. Immunity 27, 610-624.
Koyama, S., et al. "Adaptive resistance to therapeutic PD-1 blockade is associated with upregulation of alternative immune checkpoints." Nature communications 7.1 (2016): 1-9.
Krawczyk, et al., (2010). Toll-like receptor-induced changes in glycolytic metabolism regulate dendritic cell activation. Blood 115, 4742-4749.
Liu, et al., (2014a). A strategy for sensitive, large scale quantitative metabolomics. J. Vis. Exp. (87) https://doi.org/10.3791/51358.
Liu, et al., (2014b). Development and quantitative evaluation of a high-resolution metabolomics technology. Anal. Chem. 86, 2175-2184.
Liu, J., et al. "Targeting Wnt-driven cancer through the inhibition of Porcupine by LGK974." Proceedings of the National Academy of Sciences 110.50 (2013): 20224-20229.
Luke, et al., (2016). Correlation of WNT/b-catenin pathway activation with immune exclusion across most human cancers. Journal of Clinical Oncology 34, No. 15_suppl (May 20, 2016) 3004-3004.
Madan, B., et al. "Wnt addiction of genetically defined cancers reversed by PORCN inhibition." Oncogene 35.17 (2016): 2197-2207.
Malinarich, et al., (2015). High mitochondrial respiration and glycolytic capacity represent a metabolic phenotype of human tolerogenic dendritic cells. J. Immunol. 194, 5174-5186.

Manicassamy, et al., (2010). Activation of beta-catenin in dendritic cells regulates immunity versus tolerance in the intestine. Science 329, 849-853.
Mellor, et al., (2008). Creating immune privilege: active local suppression that benefits friends, but protects foes. Nat. Rev. Immunol. 8, 74-80.
Morais, C. "Sunitinib resistance in renal cell carcinoma." Journal of Kidney Cancer and VHL 1.1 (2014): 1.
Mullard, (2015). Immunotherapy interest drives IDO deals. Nat. Rev. Drug Discov. 14, 373.
Munn, et al., (2002). Potential regulatory function of human dendritic cells expressing indoleamine 2,3-dioxygenase. Science 297, 1867-1870.
Munn, et al., (2004). Expression of indoleamine 2,3-dioxygenase by plasmacytoid dendritic cells in tumordraining lymph nodes. J. Clin. Invest. 114, 280-290.
Munn, et al., (2007). Indoleamine 2,3-dioxygenase and tumorinduced tolerance. J. Clin. Invest. 117, 1147-1154.
Nair, et al., (2012). Isolation and generation of human dendritic cells. In Current Protocols in Immunology (John Wiley & Sons). https://doi.org/10.1002/0471142735.im0732s99, 7.32.
O'Neill, et al., (2016). Immunometabolism governs dendritic cell and macrophage function. J. Exp. Med. 213, 15-23.
Oderup, et al., (2013). Canonical and noncanonical Wnt proteins program dendritic cell responses for tolerance. J. Immunol. 190, 6126-6134.
Orabona, et al., (2008). SOCS3 drives proteasomal degradation of indoleamine 2,3-dioxygenase (IDO) and antagonizes IDO-dependent tolerogenesis. Proc. Natl. Acad. Sci. USA 105, 20828-20833.
Pallotta, et al., (2011). Indoleamine 2,3-dioxygenase is a signaling protein in long-term tolerance by dendritic cells. Nat. Immunol. 12, 870-878.
Park, H. W., et al. "Alternative Wnt signaling activates YAP/TAZ." Cell 162.4 (2015): 780-794.
Pesce, et al., (1975). Rapid kinetic measurement of lactate in plasma with a centrifugal analyzer. Clin. Chem. 21, 1932-1934.
Pitt, J. M., et al. "Resistance mechanisms to immune-checkpoint blockade in cancer: tumor-intrinsic and-extrinsic factors." Immunity 44.6 (2016): 1255-1269.
Proffitt, K. D., et al. "Pharmacological inhibition of the Wnt acyltransferase PORCN prevents growth of WNT-driven mammary cancer." Cancer research 73.2 (2013): 502-507.
Ribas, A., et al. "Association of pembrolizumab with tumor response and survival among patients with advanced melanoma." Jama 315.15 (2016): 1600-1609.
Salmon, et al., (2016). Expansion and activation of CD103(+) dendritic cell progenitors at the tumor site enhances tumor responses to therapeutic PD-L1 and BRAF inhibition. Immunity 44, 924-938.
Scarlett, et al., (2012). Ovarian cancer progression is controlled by phenotypic changes in dendritic cells. J. Exp. Med. 209, 495-506.
Schaale, K., et al. "Wnt signaling in macrophages: augmenting and inhibiting mycobacteria-induced inflammatory responses." European journal of cell biology 90.6-7 (2011): 553-559.
Sharma, et al., (2007). Plasmacytoid dendritic cells from mouse tumor-draining lymph nodes directly activate mature Tregs via indoleamine 2,3-dioxygenase. J. Clin. Invest. 117, 2570-2582.
Sharma, P., et al. "Primary, adaptive, and acquired resistance to cancer immunotherapy." Cell 168.4 (2017): 707-723.
Shen, et al., (1997). Cloned dendritic cells can present exogenous antigens on both MHC class I and class II molecules. J. Immunol. 158, 2723-2730.
Sherwood, et al., (2014). WNT5A-mediated b-catenin-independent signalling is a novel regulator of cancer cell metabolism. Carcinogenesis 35, 784-794.
Shimizu, et al., (1978). Indoleamine 2, 3-dioxygenase. Purification and some properties. J. Biol. Chem. 253, 4700-4706.
Spranger, et al., (2013). Up-regulation of PD-L1, IDO, and T(regs) in the melanoma tumor microenvironment is driven by CD8(+) T cells. Sci. Transl. Med. 5, 200ra116.
Spranger, et al., (2015). Melanoma-intrinsic b-catenin signalling prevents anti-tumour immunity. Nature 523, 231-235.

(56) References Cited

OTHER PUBLICATIONS

Spranger, et al., (2017). Tumor-residing Batf3 dendritic cells are required for effector T cell trafficking and adoptive T cell therapy. Cancer Cell 31, 711-723 e714.

Sweis, et al., (2016). Molecular drivers of the non-T-cell-inflamed tumor microenvironment in urothelial bladder cancer. Cancer Immunol. Res. 4, 563-568.

Takada, K., et al. "Targeted disruption of the BCL9/ß-catenin complex inhibits oncogenic Wnt signaling." Science translational medicine 4.148 (2012): 148ra117-148ra117.

Thomas, et al., (2001). Antioxidants inhibit indoleamine 2,3-dioxygenase in IFNgamma—activated human macrophages: post-translational regulation by pyrrolidine dithiocarbamate. J. Immunol. 166, 6332-6340.

Wang, G., et al. "Targeting YAP-dependent MDSC infiltration impairs tumor progression." Cancer discovery 6.1 (2016): 80-95.

Wisniewski, J. A., et al. "Structure-based design of 1,4-dibenzoylpiperazines as ß-catenin/B-cell lymphoma 9 protein-protein interaction inhibitors." ACS medicinal chemistry letters 7.5 (2016): 508-513.

Zhang, X et al. "Development of anticancer agents targeting the Wnt/ß-catenin signaling." American journal of cancer research 5.8 (2015): 2344.

Zhao, et al., (2014). Arsenite-induced pseudo-hypoxia results in loss of anchorage-dependent growth in BEAS-2B pulmonary epithelial cells. PLoS ONE 9, e114549.

Zhao, et al., (2015). Culture conditions profoundly impact phenotype in BEAS-2B, a human pulmonary epithelial model. J. Appl. Toxicol. 35, 945-951.

Zhao, F., et al. "Paracrine Wnt5a-ß-catenin signaling triggers a metabolic program that drives dendritic cell tolerization." Immunity 48.1 (2018): 147-160.

Zito, G, et al. "Spontaneous tumour regression in keratoacanthomas is driven by Wnt/retinoic acid signalling cross-talk." Nature communications 5.1 (2014): 1-13.

* cited by examiner

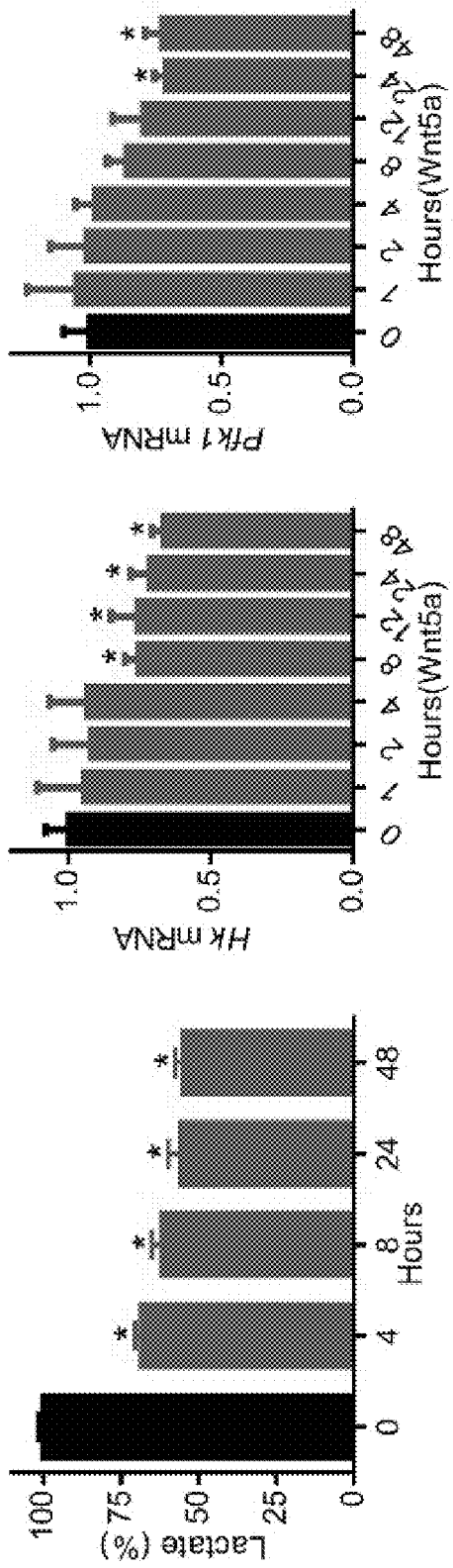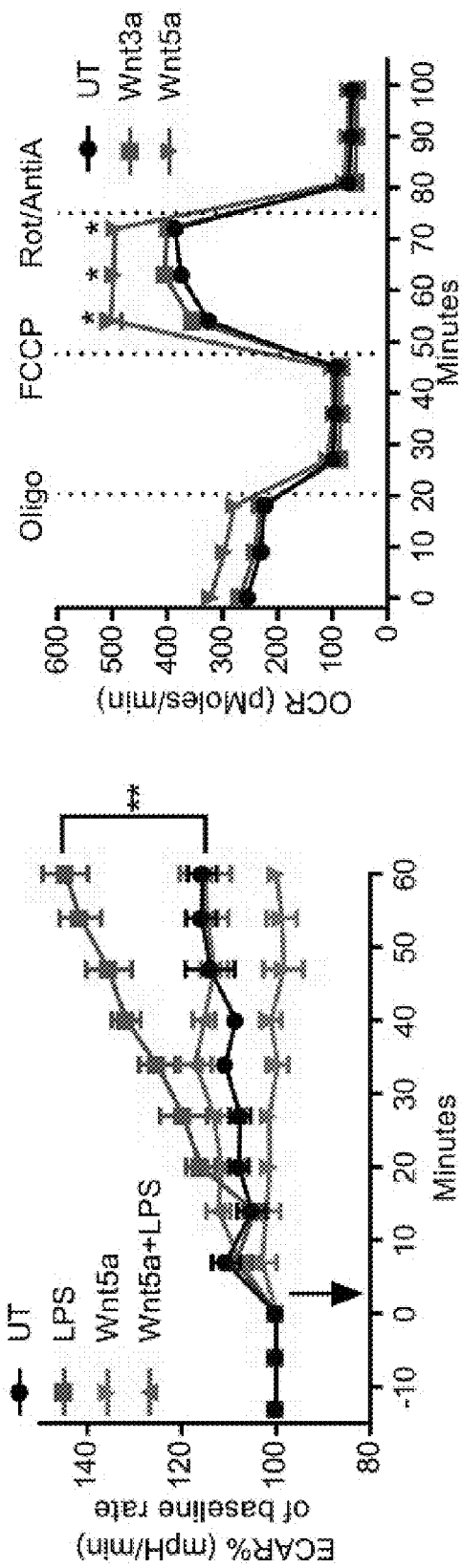

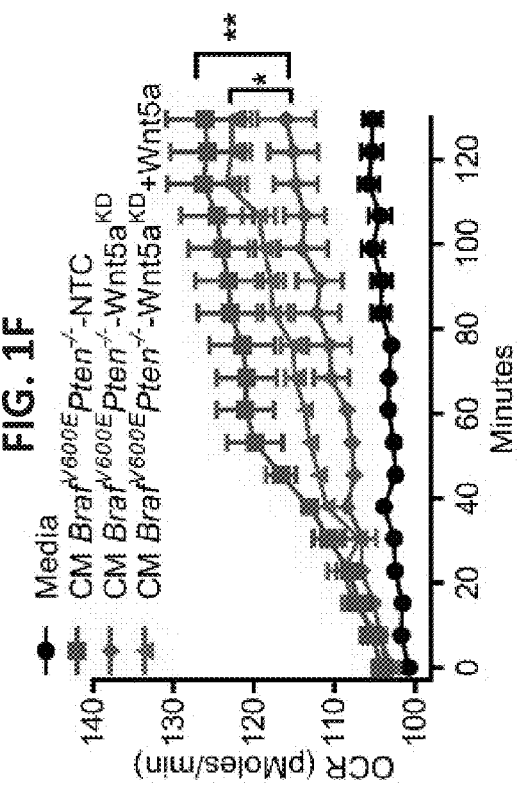
FIG. 1E
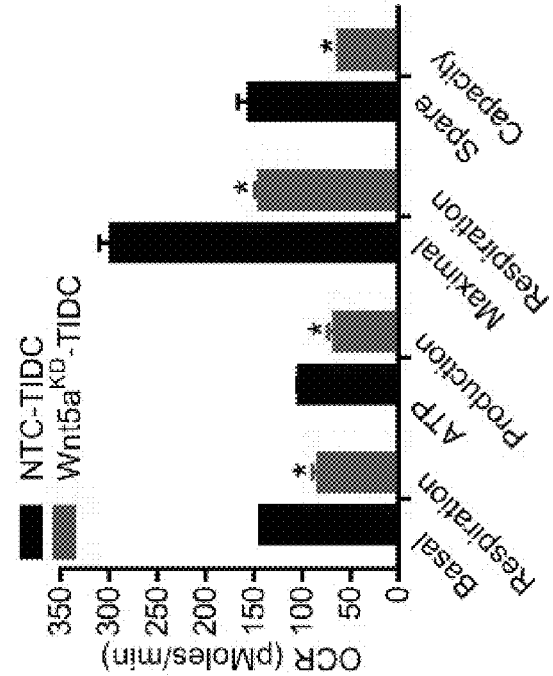
FIG. 1F
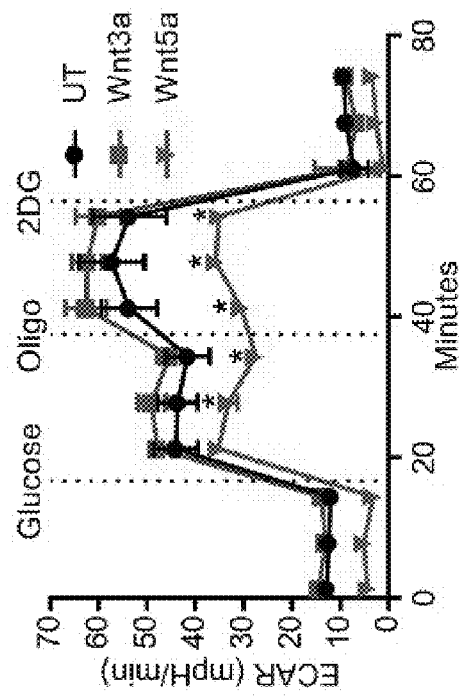
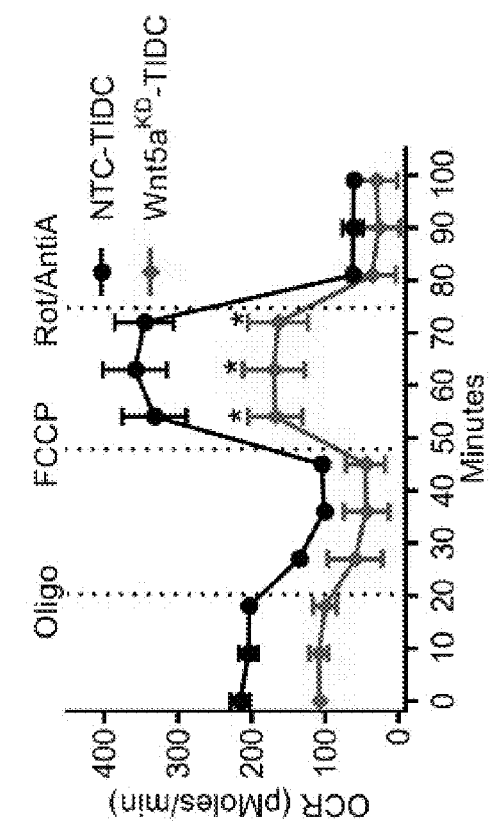
FIG. 1G
FIG. 1H

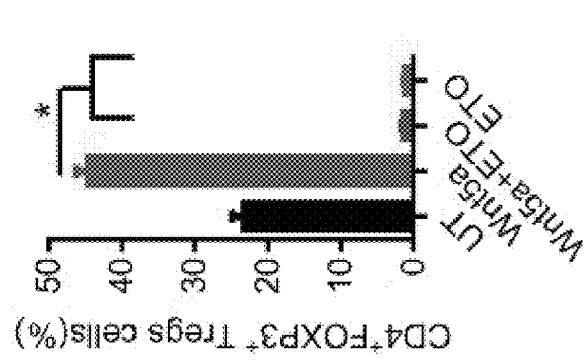
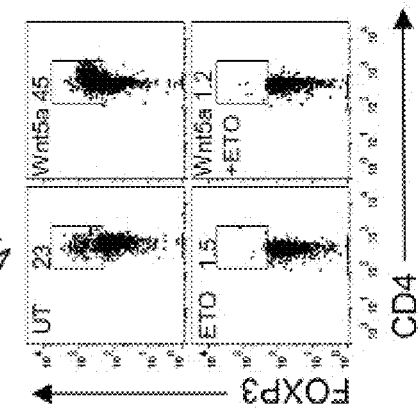
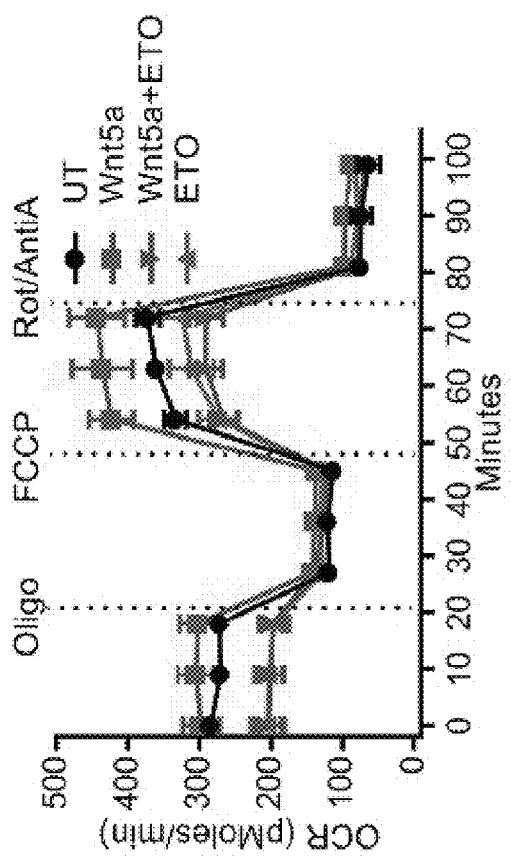
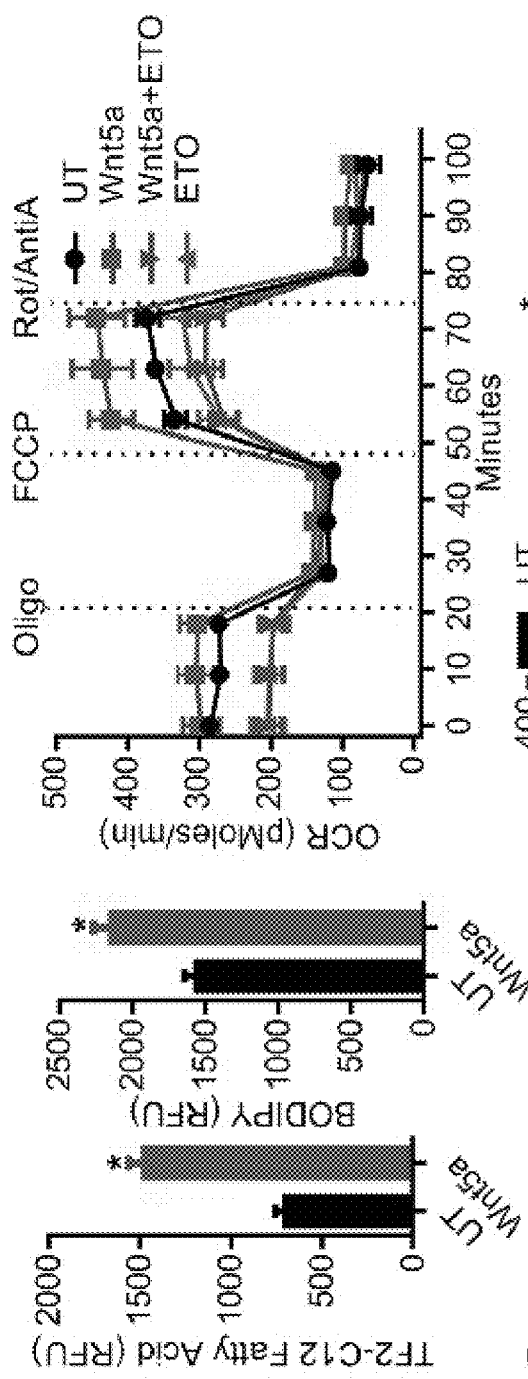
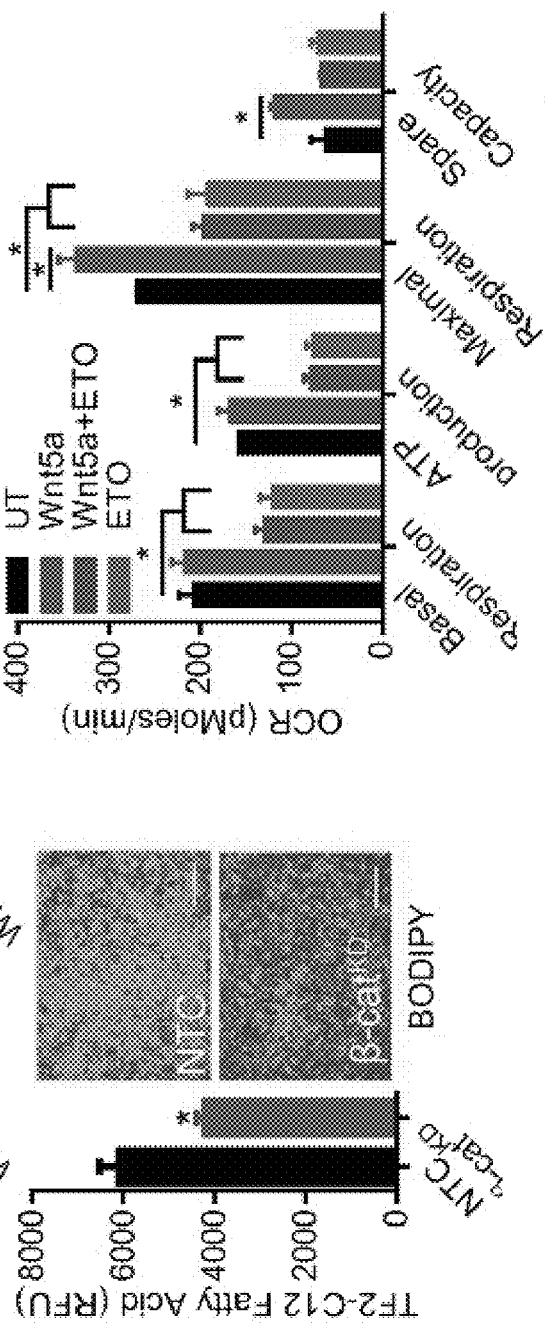

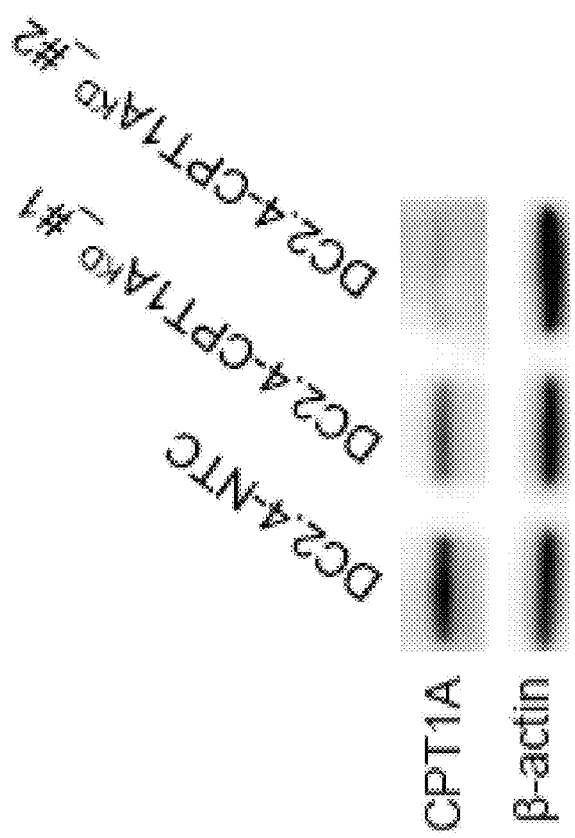
FIG. 7A
FIG. 7B
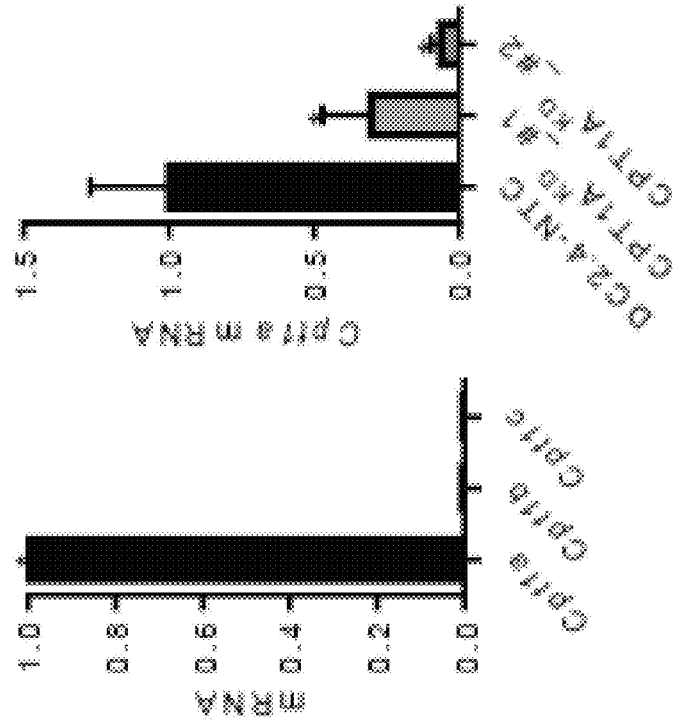
FIG. 7C

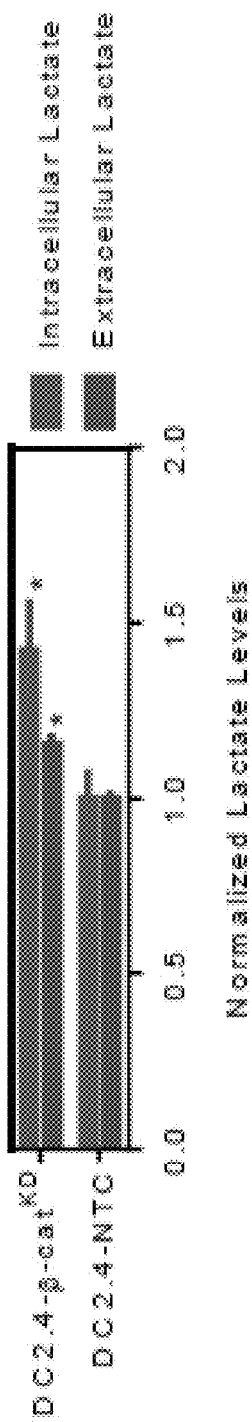
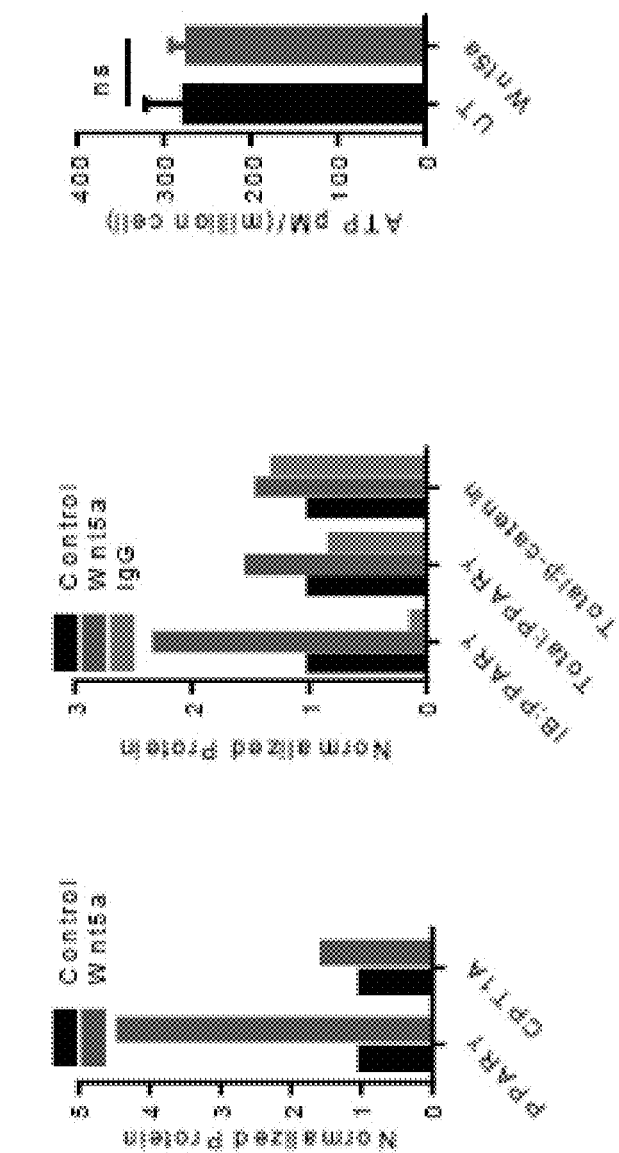
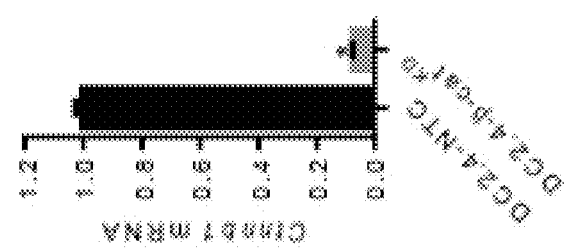
FIG. 8F  FIG. 8G  FIG. 8H  FIG. 8I  FIG. 8J

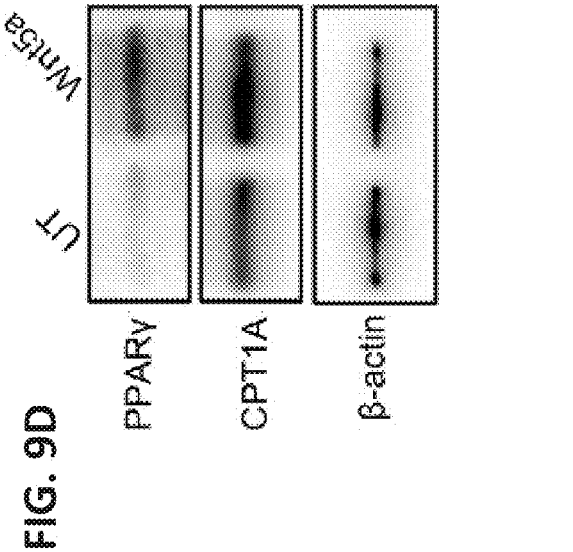
FIG. 9B  FIG. 9C  FIG. 9D
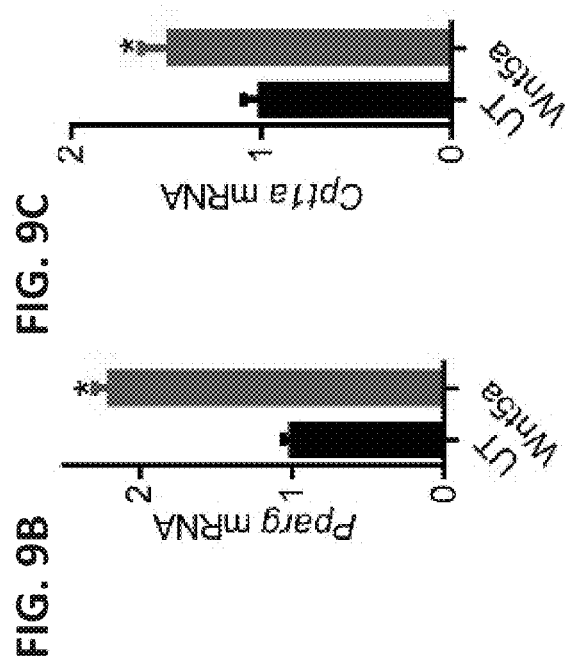
FIG. 9E  FIG. 9F  FIG. 9G
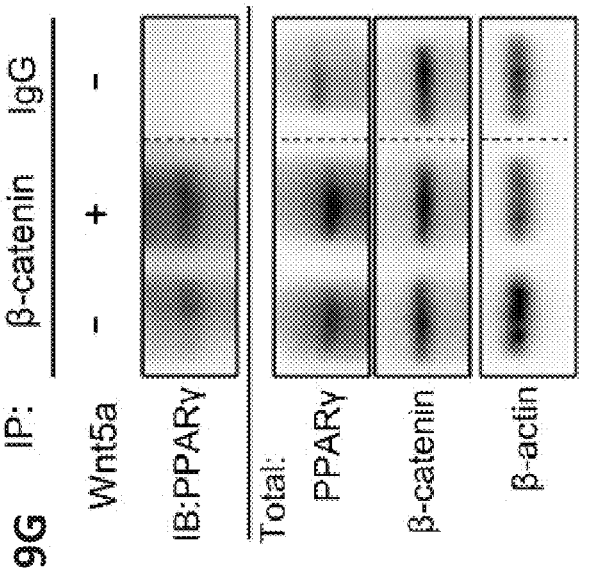
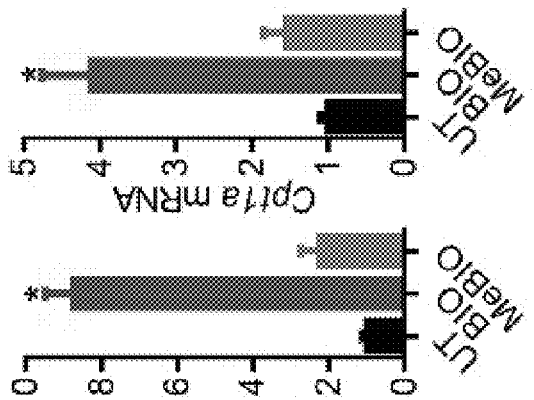
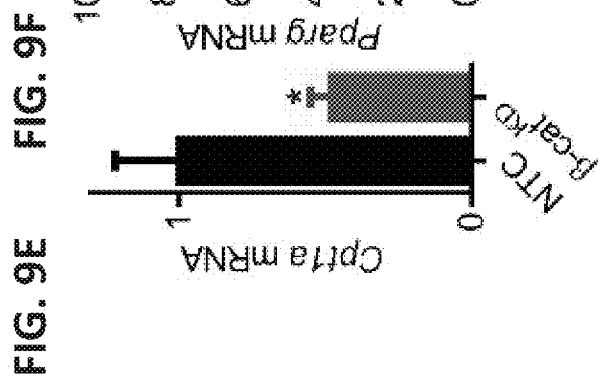

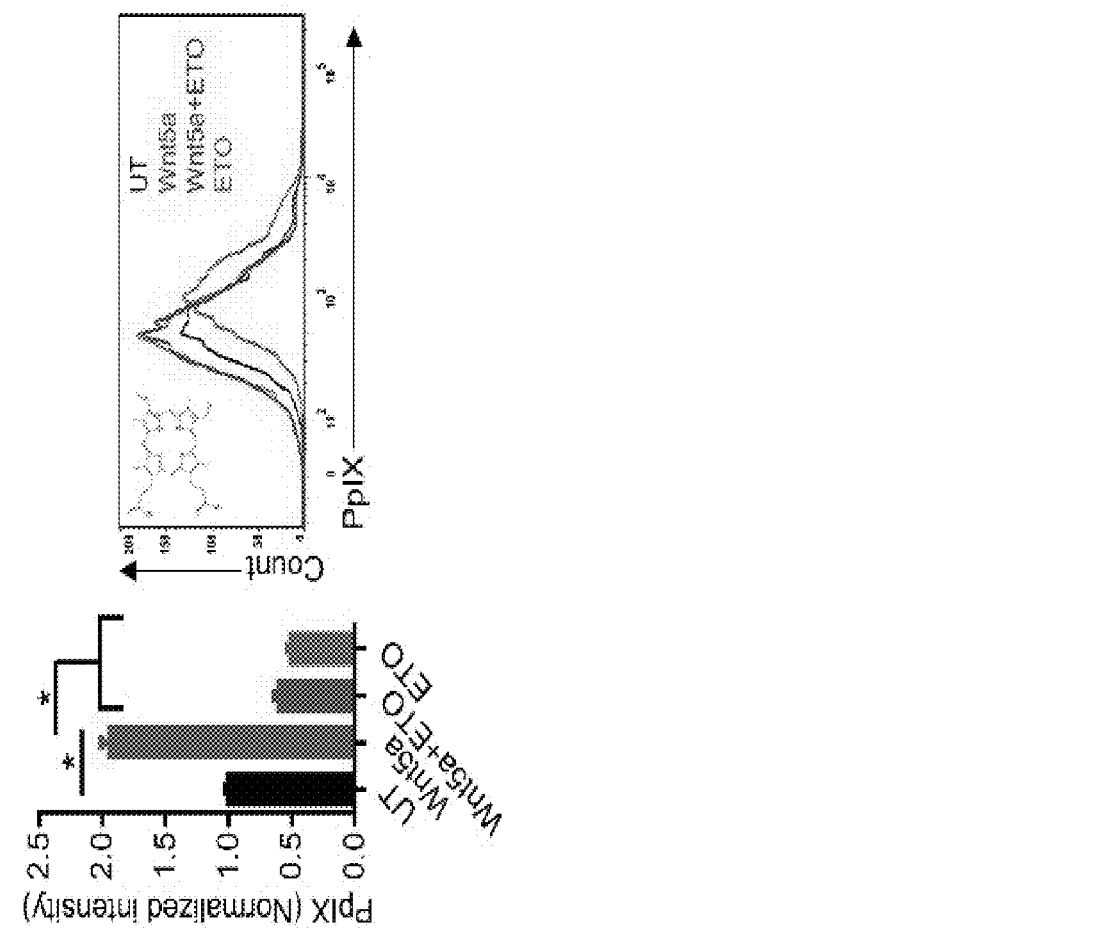
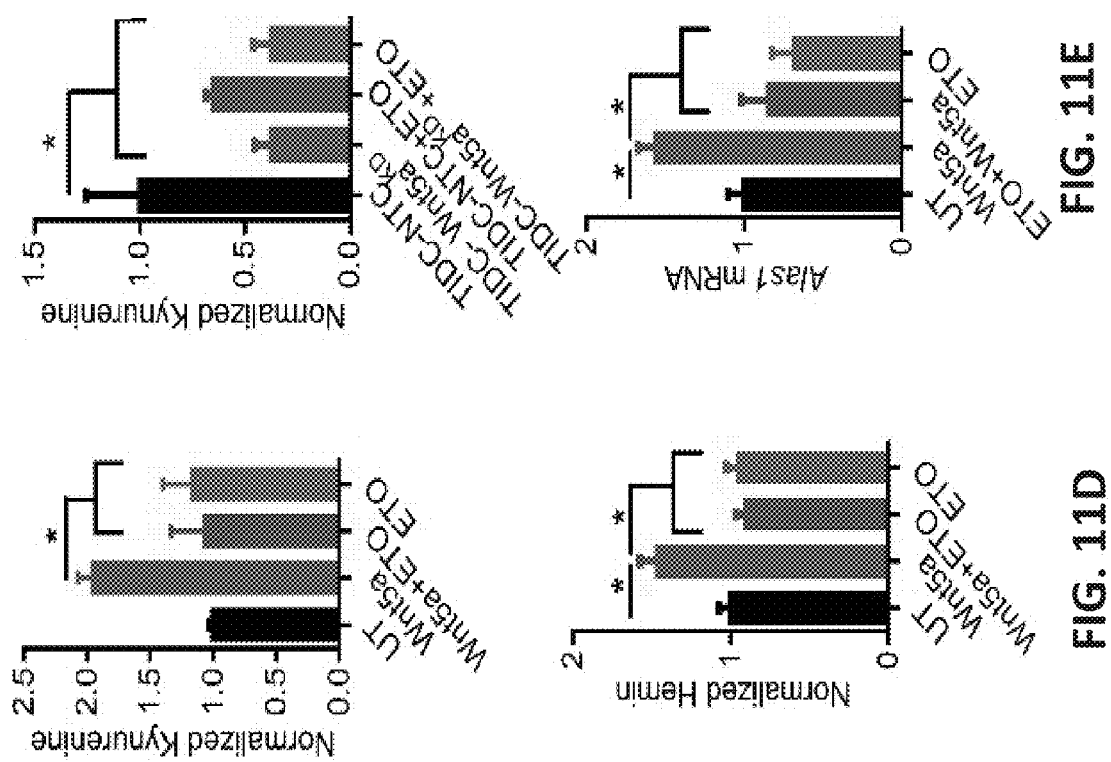

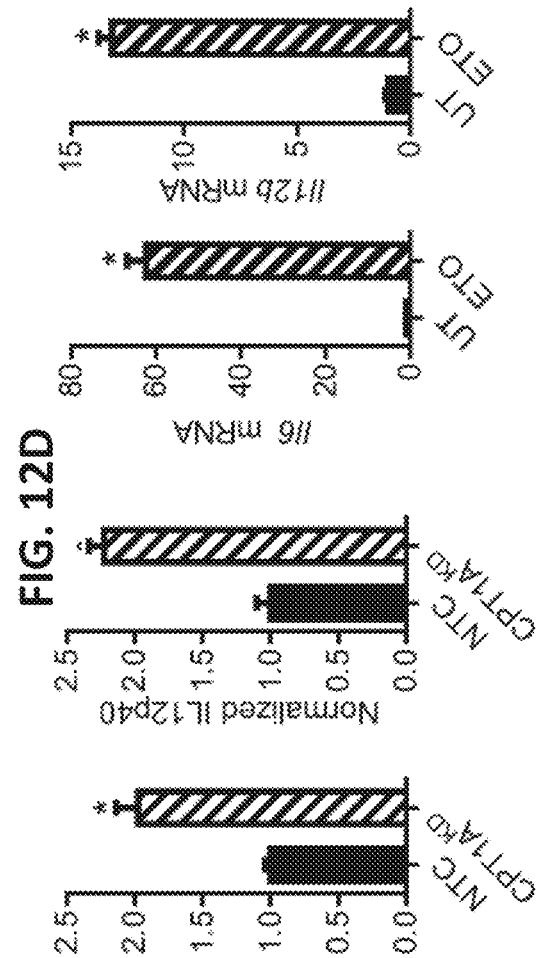
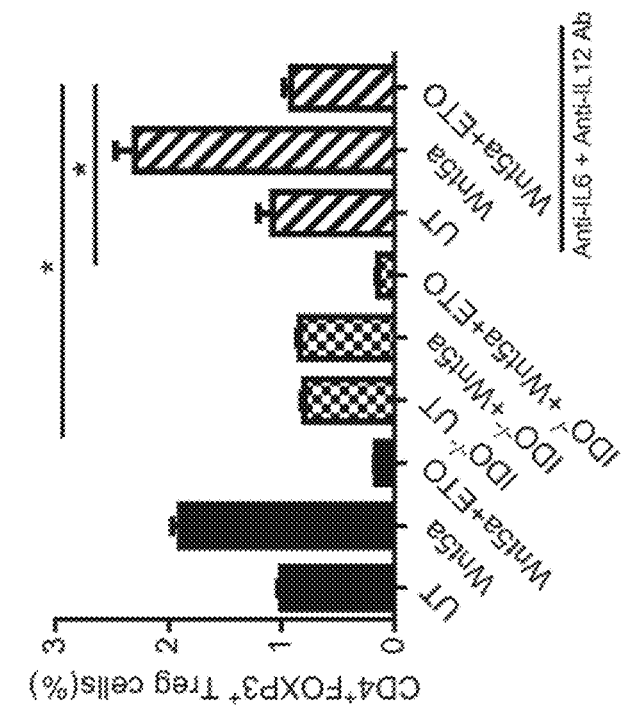
FIG. 12A
FIG. 12B
FIG. 12C
FIG. 12D

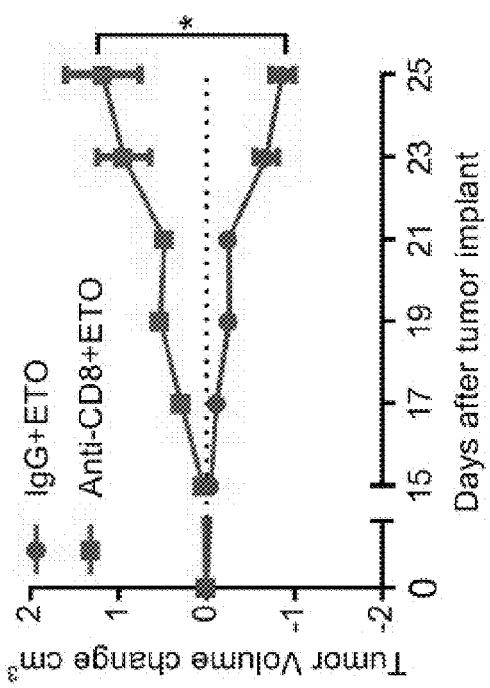
FIG. 13E
FIG. 13F
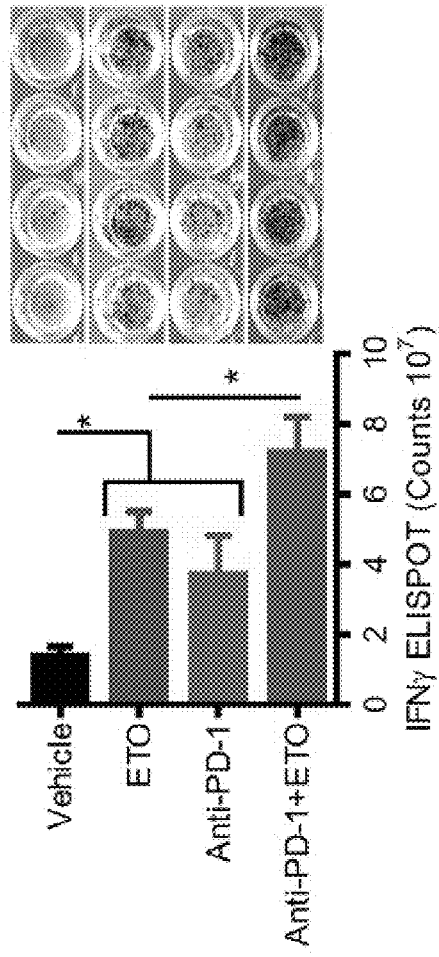
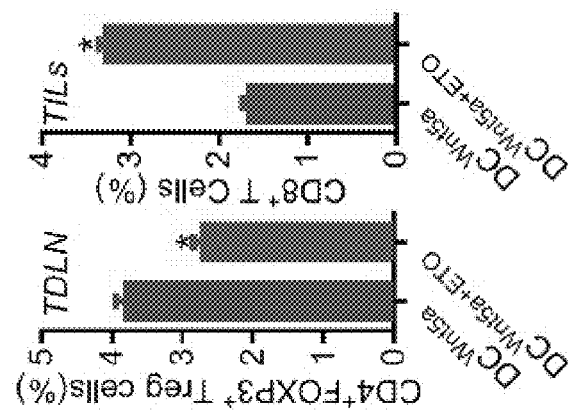
FIG. 13G
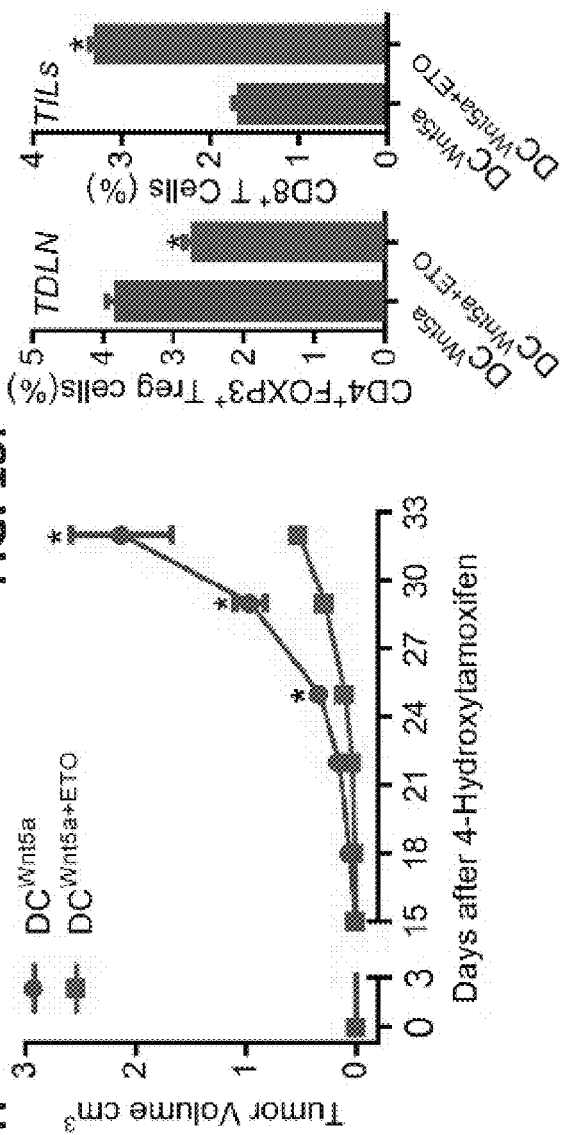
FIG. 13H
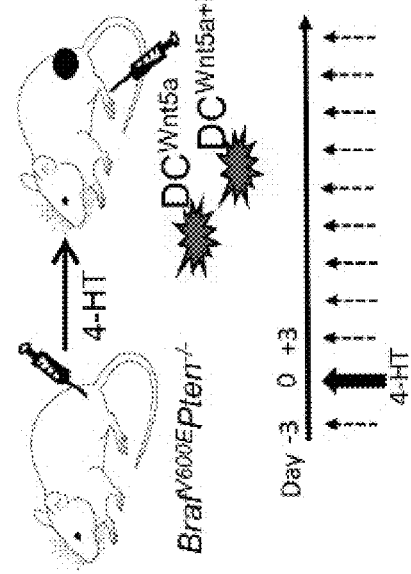
FIG. 13I PORCN inhibitors
Wnt-C59 (PubChem: 57519544)

ETC-159

IWP12 (PubChem CID: 3244448)

IWP2 (PubChem CID: 2155128)

IWPL6

LGK 974 (PubChem CID: 46926973)

IWP-01

IWP-N3

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Primer: mACTB Forward

<400> SEQUENCE: 1
ggctgtattc ccctccatcg                                          20

<210> SEQ ID NO 2
<211> LENGTH: 22
<212> TYPE: DNA
<213> ORGANISM: Artificial Sequence
<220> FEATURE:
<223> OTHER INFORMATION: Primer: mACTB Reverse

<400> SEQUENCE: 2
ccagttggta acaatgccat gt                                       22

<210> SEQ ID NO 3
<211> LENGTH: 21
<212> TYPE: DNA
<213> ORGANISM: Artificial Sequence
<220> FEATURE:
<223> OTHER INFORMATION: Primer: mPPARg Forward

<400> SEQUENCE: 3
gccctttggt gactttatgg a                                        21

<210> SEQ ID NO 4
<211> LENGTH: 20
<212> TYPE: DNA
<213> ORGANISM: Artificial Sequence
<220> FEATURE:
<223> OTHER INFORMATION: Primer: mPPARg Reverse

<400> SEQUENCE: 4
gcagcaggtt gtcttggatg                                          20

<210> SEQ ID NO 5
<211> LENGTH: 21
<212> TYPE: DNA
<213> ORGANISM: Artificial Sequence
<220> FEATURE:
<223> OTHER INFORMATION: Primer: mCPT1A Forward

<400> SEQUENCE: 5
ctcagtggga gcgactcttc a                                        21

<210> SEQ ID NO 6
<211> LENGTH: 21
<212> TYPE: DNA
<213> ORGANISM: Artificial Sequence
<220> FEATURE:
<223> OTHER INFORMATION: Primer: mCPT1A Reverse

<400> SEQUENCE: 6
ggcctctgtg gtacacgaca a                                        21

<210> SEQ ID NO 7
<211> LENGTH: 20
<212> TYPE: DNA
<213> ORGANISM: Artificial Sequence

```
<220> FEATURE:
<223> OTHER INFORMATION: Primer: mCPT1B Forward

<400> SEQUENCE: 7
ttcaacacta cacgcatccc                                               20

<210> SEQ ID NO 8
<211> LENGTH: 19
<212> TYPE: DNA
<213> ORGANISM: Artificial Sequence
<220> FEATURE:
<223> OTHER INFORMATION: Primer: mCPT1B Reverse

<400> SEQUENCE: 8
gccctcatag agccagacc                                                19

<210> SEQ ID NO 9
<211> LENGTH: 21
<212> TYPE: DNA
<213> ORGANISM: Artificial Sequence
<220> FEATURE:
<223> OTHER INFORMATION: Primer: mCPT1C Forward

<400> SEQUENCE: 9
tcttcactga gttccgatgg g                                             21

<210> SEQ ID NO 10
<211> LENGTH: 20
<212> TYPE: DNA
<213> ORGANISM: Artificial Sequence
<220> FEATURE:
<223> OTHER INFORMATION: Primer: mCPT1C Reverse

<400> SEQUENCE: 10
acgccagaga tgcctttttcc                                              20

<210> SEQ ID NO 11
<211> LENGTH: 23
<212> TYPE: DNA
<213> ORGANISM: Artificial Sequence
<220> FEATURE:
<223> OTHER INFORMATION: Primer:  mIL6  Forward

<400> SEQUENCE: 11
tagtccttcc taccccaatt tcc                                           23

<210> SEQ ID NO 12
<211> LENGTH: 21
<212> TYPE: DNA
<213> ORGANISM: Artificial Sequence
<220> FEATURE:
<223> OTHER INFORMATION: Primer:  mIL6  Reverse

<400> SEQUENCE: 12
ttggtcctta gccactcctt c                                             21

<210> SEQ ID NO 13
<211> LENGTH: 19
<212> TYPE: DNA
<213> ORGANISM: Artificial Sequence
<220> FEATURE:
<223> OTHER INFORMATION: Primer: mIL10 Forward

<400> SEQUENCE: 13
gaccagctgg acaacatac                                                19
```

<210> SEQ ID NO 14
<211> LENGTH: 18
<212> TYPE: DNA
<213> ORGANISM: Artificial Sequence
<220> FEATURE:
<223> OTHER INFORMATION: Primer: mIL10 Reverse

<400> SEQUENCE: 14
ctggagtcca gcagactc                                           18

<210> SEQ ID NO 15
<211> LENGTH: 20
<212> TYPE: DNA
<213> ORGANISM: Artificial Sequence
<220> FEATURE:
<223> OTHER INFORMATION: Primer: mIL12B Forward

<400> SEQUENCE: 15
gaacacatgc ccacttgctg                                         20

<210> SEQ ID NO 16
<211> LENGTH: 22
<212> TYPE: DNA
<213> ORGANISM: Artificial Sequence
<220> FEATURE:
<223> OTHER INFORMATION: Primer: mIL12B Reverse

<400> SEQUENCE: 16
cgtgctcatg gctggtgcaa ag                                      22

<210> SEQ ID NO 17
<211> LENGTH: 20
<212> TYPE: DNA
<213> ORGANISM: Artificial Sequence
<220> FEATURE:
<223> OTHER INFORMATION: Primer: mTGFb Forward

<400> SEQUENCE: 17
gcaacaacgc catctatgag                                         20

<210> SEQ ID NO 18
<211> LENGTH: 19
<212> TYPE: DNA
<213> ORGANISM: Artificial Sequence
<220> FEATURE:
<223> OTHER INFORMATION: Primer: mTGFb Reverse

<400> SEQUENCE: 18
tctttgctgt cacaagagc                                          19

<210> SEQ ID NO 19
<211> LENGTH: 20
<212> TYPE: DNA
<213> ORGANISM: Artificial Sequence
<220> FEATURE:
<223> OTHER INFORMATION: Primer: mPFK Forward

<400> SEQUENCE: 19
ggaggcgaga acatcaagcc                                         20

<210> SEQ ID NO 20
<211> LENGTH: 19
<212> TYPE: DNA
<213> ORGANISM: Artificial Sequence
<220> FEATURE:
<223> OTHER INFORMATION: Primer: mPFK Reverse

```
<400> SEQUENCE: 20
cggccttccc tcgtagtga                                             19

<210> SEQ ID NO 21
<211> LENGTH: 19
<212> TYPE: DNA
<213> ORGANISM: Artificial Sequence
<220> FEATURE:
<223> OTHER INFORMATION: Primer: mHK3 Forward

<400> SEQUENCE: 21
tgctgcccac atacgtgag                                             19

<210> SEQ ID NO 22
<211> LENGTH: 20
<212> TYPE: DNA
<213> ORGANISM: Artificial Sequence
<220> FEATURE:
<223> OTHER INFORMATION: Primer: mHK3 Reverse

<400> SEQUENCE: 22
cctgtcagtg ttacccacaa                                            20

<210> SEQ ID NO 23
<211> LENGTH: 20
<212> TYPE: DNA
<213> ORGANISM: Artificial Sequence
<220> FEATURE:
<223> OTHER INFORMATION: Primer: mCTNNB Forward

<400> SEQUENCE: 23
tcccatccac gcagtttgac                                            20

<210> SEQ ID NO 24
<211> LENGTH: 23
<212> TYPE: DNA
<213> ORGANISM: Artificial Sequence
<220> FEATURE:
<223> OTHER INFORMATION: Primer: mCTNNB Reverse

<400> SEQUENCE: 24
tcctcatcgt ttagcagttt tgt                                        23

<210> SEQ ID NO 25
<211> LENGTH: 23
<212> TYPE: DNA
<213> ORGANISM: Artificial Sequence
<220> FEATURE:
<223> OTHER INFORMATION: Primer: mALAS1 Forward

<400> SEQUENCE: 25
gatgccaggc tgtgaaattt act                                        23

<210> SEQ ID NO 26
<211> LENGTH: 20
<212> TYPE: DNA
<213> ORGANISM: Artificial Sequence
<220> FEATURE:
<223> OTHER INFORMATION: Primer: mALAS1 Reverse

<400> SEQUENCE: 26
ctgttgcgaa tcccttggat                                            20

<210> SEQ ID NO 27
```

```
<211> LENGTH: 24
<212> TYPE: DNA
<213> ORGANISM: Artificial Sequence
<220> FEATURE:
<223> OTHER INFORMATION: Primer: mGAPDH Forward

<400> SEQUENCE: 27
gtctacatgt tccagtatga ctcc                                          24

<210> SEQ ID NO 28
<211> LENGTH: 25
<212> TYPE: DNA
<213> ORGANISM: Artificial Sequence
<220> FEATURE:
<223> OTHER INFORMATION: Primer: mGAPDH Reverse

<400> SEQUENCE: 28
agtgagttgt catatttctc gtggt                                         25
```

PREDICTIVE BIOMARKERS FOR CANCER IMMUNOTHERAPY AND METHODS OF USING SAME

CROSS-REFERENCE TO RELATED APPLICATIONS

This application claims priority to U.S. Provisional Application No. 62/657,132 filed on Apr. 13, 2018, the contents of which are incorporated by reference in its entirety.

STATEMENT REGARDING FEDERALLY SPONSORED RESEARCH

N/A

BACKGROUND OF THE INVENTION

The field of the invention is related to methods of detecting biomarkers of resistance to cancer therapy and providing compositions and methods for treating the resistant cancers.

While immunotherapy has resulted in significant responses in some cancer patients, the majority of patients with advanced cancer fail to respond to this general treatment approach. In even the most immunogenic cancer like melanoma, the response rate remains below 40%. There are currently no biomarkers that reliably predict which cancer patients will respond or be resistant to checkpoint inhibitor immunotherapy. Clinically useful biomarkers capable of predicting which patients may respond to immunotherapy strategies would streamline treatment plans, thereby assigning more effective therapies to patients sooner while avoiding the use of costly therapies that will ultimately fail in the clinic. This would optimize clinical outcomes for patients while lowering health care costs.

SUMMARY OF THE INVENTION

The present disclosure is based, in part, on the findings from the inventors that tumor-mediated paracrine wnt-β-catenin signaling plays an important role in promoting local immune tolerance and driving adaptive resistance to anti-PD-1 antibody immunotherapy. Further, studies have shown that the inhibition of Wnt ligand signaling is capable promoting immune-mediated responses to cancer in vivo and suppressing their progression when administered in combination with anti-PD-1 antibody therapy.

Accordingly, one aspect of the present disclosure provides a method of determining and detecting the presence of a wnt-β-catenin-mediated cancer in a subject comprising, consisting of, or consisting essentially of quantifying the amount of at least one biomarker present in a biological sample derived from the subject, wherein the biomarker is associated with wnt-β-catenin-mediated cancer.

Another aspect of the present disclosure provides a method of diagnosing a wnt-β-catenin-mediated cancer in a subject comprising, consisting of, or consisting essentially of quantifying the amount of at least one biomarker present in a biological sample derived from the subject, wherein the biomarker is associated with a wnt-β-catenin-mediated cancer.

Another aspect of the present disclosure provides a method of determining the presence of an immunotherapy-resistant wnt-β-catenin-mediated cancer in a subject comprising, consisting of, or consisting essentially of quantifying the amount of at least one biomarker present in a biological sample derived from the subject, wherein the biomarker is associated with an immunotherapy-resistant wnt-β-catenin-mediated cancer.

Another aspect of the present disclosure provides a method of determining the presence of a wnt-β-catenin-mediated cancer in a subject comprising, consisting of, or consisting essentially of: (a) obtaining a biological sample from a subject; (b) determining the expression level of one or more biomarkers that are associated with a wnt-β-catenin-mediated cancer in the biological sample; (c) comparing the expression level of the biomarkers in the biological sample with that of a control, wherein the presence of one or more of the biomarkers in the sample that is in an amount greater than that of the control indicates the presence of a wnt-β-catenin-mediated cancer; and (d) administering appropriate anti-wnt-β-catenin-mediated cancer therapy if one or more of the biomarkers are expressed.

Another aspect of the present disclosure provides a method of diagnosing a wnt-β-catenin-mediated cancer in a subject comprising, consisting of, or consisting essentially of: (a) obtaining a biological sample from a subject; (b) determining the expression level of one or more biomarkers that are associated with a wnt-β-catenin-mediated cancer in the biological sample; (c) comparing the expression level of the biomarkers in the biological sample with that of a control, wherein the presence of one or more of the biomarkers in the sample that is in an amount greater than that of the control indicates a wnt-β-catenin-mediated cancer; and (d) administering appropriate anti-wnt-β-catenin-mediated cancer therapy if one or more of the biomarkers are expressed.

Another aspect of the present disclosure provides a method of determining the presence of an immunotherapy-resistant wnt-β-catenin-mediated cancer in a subject comprising, consisting of, or consisting essentially of: (a) obtaining a biological sample from a subject; (b) determining the expression level of one or more biomarkers that are associated with an immunotherapy-resistant wnt-β-catenin-mediated cancer in the biological sample; (c) comparing the expression level of the biomarkers in the biological sample with that of a control, wherein the presence of one or more of the biomarkers in the sample that is in an amount greater than that of the control indicates the presence of an immunotherapy-resistant wnt-β-catenin-mediated cancer; (d) administering an appropriate anti-wnt-β-catenin signaling pathway inhibitor and an anti-wnt-β-catenin-mediated cancer immunotherapy if one or more of the biomarkers are expressed.

In some embodiments, the biomarker is selected from the group consisting of wnt5a, CXCL2, CXCL5, CXCR2, HSP70, YAP1, NPRP3 and combinations thereof. In one embodiment, the detecting one or more biomarkers in a sample from a subject, selected from the group consisting of wnt5a, CXCL2, CXCL5, CXCR2, HSP70, and combinations thereof.

In another embodiment, the immunotherapy comprises an anti-PD1 antibody immunotherapy.

In some embodiments, the subject is a mammal. In other embodiments, the subject is a human.

In other embodiments, the biological sample is selected from the group consisting of tissues, cells, biopsies, blood, lymph, serum, plasma, urine, saliva, mucus, and tears. In certain embodiments, the sample comprises a biopsy, preferably a tumor biopsy.

In other embodiments, wnt-β-catenin-mediated cancer comprises melanoma.

In another embodiment, the disclosure provides a method of detecting the presence of a wnt-β-catenin-mediated cancer in a subject comprising detecting in a biological sample derived from the subject at least one biomarker associated with wnt-β-catenin-mediated cancer selected from the group consisting of wnt5a, CXCL2, CXCL5, CXCR2, HSP70, S100A8, S100A9, YAP1, NPRP3 and combinations thereof. In some embodiments, the method comprises the steps of: (a) obtaining a biological sample from the subject; (b) determining the expression level of one or more biomarkers that are associated with a wnt-β-catenin-mediated cancer selected from the group consisting of wnt5a, CXCL2, CXCL5, CXCR2, HSP70, S100A8, S100A9 and combinations thereof in the biological sample; (c) comparing the expression level of the one or more biomarker in the biological sample with that of a control, wherein the presence of one or more of the biomarkers in the sample that is in an amount greater than that of the control indicates the presence of a wnt-β-catenin-mediated cancer.

In another embodiment, the present disclosure provides a method of determining the presence of an immunotherapy-resistant wnt-β-catenin-mediated cancer in a subject comprising detecting at least one biomarker selected from the group consisting of wnt5a, CXCL2, CXCL5, CXCR2, HSP70 and combinations thereof present in a biological sample derived from the subject, wherein the biomarker is associated with an immunotherapy-resistant wnt-β-catenin-mediated cancer. In some embodiments, the method comprises the steps of (a) obtaining a biological sample from a subject; (b) determining the expression level of one or more biomarkers that are associated with an immunotherapy-resistant wnt-β-catenin-mediated cancer in the biological sample; and (c) comparing the expression level of the biomarkers in the biological sample with that of a control, wherein the presence of one or more of the biomarkers in the sample that is in an amount greater than that of the control indicates the presence of an immunotherapy-resistant wnt-β-catenin-mediated cancer.

In another embodiment, the disclosure provides a method of treating a subject having or suspected of having an immunotherapy resistant tumor, the method comprising: (a) detecting the presence of a wnt-β-catenin-mediated cancer in a subject comprising detecting in a biological sample derived from the subject at least one biomarker associated with wnt-β-catenin-mediated cancer selected from the group consisting of wnt5a, CXCL2, CXCL5, CXCR2, HSP70, S100A8, S100A9, YAP1, NPRP3 and combinations thereof, wherein detection of the one or more biomarkers indicated an immunotherapy resistant tumor, and (b) administering a therapeutically effective amount of one or more anti-wnt-β-catenin-mediated cancer immunotherapy to the subject having an immunotherapy resistant tumor.

Another aspect of the present disclosure provides all that is described and illustrated herein.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows a bar graph of levels of lactate in bone-marrow-derived dendritic cell (BMDC) culture media from 0 to 48 hr following rWnt5a treatment. n=6. FIG. 1B shows a set of bar graphs of Hk (left) and PJk1 (right) mRNA levels in dendritic cells (DCs) following rWnt5a treatment based on qRT-PCR analysis. n=3. FIG. 1C shows a scatterplot of the measured extracellular acidification rate (ECAR, milli pH units/minute, normalized to 0 min) of DCs treated with rWnt5a, LPS, or both reagents and of untreated (UT) control cells. The black arrow indicates the time of LPS injection. n=6. FIG. 1D shows a scatterplot of the measured oxygen consumption rate (OCR, picomoles/minute) of DCs pre-treated with rWnt5a or rWnt3a. n=6. The time at which oligomycin (Oligo), uncoupling agent (FCCP), and rotenone (Rot/AntiA) were applied are indicated with dashed lines. FIG. 1E shows a scatterplot of the measured ECAR of DCs pre-treated with rWnt5a or rWnt3a. n=6. The times at which glucose, Oligo, and 2-deoxyglucose (2DG) were applied are indicated with dashed lines. FIG. 1F shows a scatterplot of the measured OCR of DCs injected with media alone or with concentrated conditioned media (CM) from $Braf^{V600E}Pten^{-/-}$-NTC or -Wnt5a knockdown (KD) cell cultures, in the presence and absence of rWnt5a. n=6. FIG. 1G shows a scatterplot of the measured OCR of tumor-infiltrating DCs isolated from $Braf^{V600E}Pten^{-/-}$-NTC and -Wnt5aKD mice. n=3/group. The times at which Oligo, FCCP, and Rot/AntiA were applied are indicated with dashed lines. FIG. 1H shows a bar graph of the ORC measurements presented in FIG. 1G. n=3/group. All data are mean±SEM. *P<0.05, **P<0.005.

FIG. 21H shows a scatterplot of the simultaneous OCR collected with the data presented in FIG. 1G.

FIG. 5A shows two bar graphs. The left graph shows DC uptake of the fluorescent dodecanoic acid fatty acid substrate TF2-C12, measured by flow cytometry after treatment with rWnt5a or vehicle control (UT). n=3. The right graph shows DC intracellular lipid content following rWnt5a treatment, measured by quantification of the fluorescent lipid probe BODIPY. n=3. FIG. 5B shows a bar graph of the fatty acid uptake of DC2.4-β-cat$^{KD}$ and DC2.4-NTC cell lines. n=3. The right panel contains two microscopic immunofluorescence images in which lipids were detected in DC2.4-β-cat$^{KD}$ and DC2.4-NTC cell lines stained with BODIPY (green, scale bar, 1 cm). n=3. FIG. 5C shows a scatterplot of the measured OCR of BMDCs pre-treated with rWnt5a, ETO or both reagents. FIG. 5D shows a bar graph quantifying the OCR measurements presented in FIG. 3C. n=6. FIG. 5E shows a bar graph of the percent of DC-induced $CD4^+FoxP3^+$ Treg cells measured by in vitro Treg cell assay after DCs were treated with Wnt5a, ETO, or both reagents. n=3. The panel below shows representative flow cytometry plots based on three independent experiments.

FIG. 7A shows a bar graph of the mRNA levels of three CPT1A isoforms in primary DCs based on qRT-PCR analysis. FIG. 7B shows a bar graph of the levels of Cpt1a mRNA in two DC2.4 cell lines in which this gene has been knocked down (KD). FIG. 7C shows a western blot probing for CPT1A in DC2.4-NTC control cells and the DC2.4-CPT1A$^{KD}$ cell lines.

FIG. 8F shows a bar graph of β-catenin expression levels in the DC2.4-NTC control and DC2.4-β-catenin$^{KD}$ cell lines based on qRT-PCR analysis. FIG. 8G shows a bar graph of extracellular and intracellular lactate levels in DC2.4-NTC and DC2.4-β-catenin$^{KD}$ cell lines. FIG. 8H shows a bar graph of densitometry measurements taken from the western blot presented in FIG. 9D, normalized to housekeeping gene β-actin. FIG. 8I shows a bar graph of densitometry measurements taken from the western blot presented in FIG. 9G, normalized to housekeeping gene β-actin. FIG. 8J shows a bar graph of the ATP levels in DCs treated with Wnt5a. n=3. All data is mean±SEM. *P<0.05.

n=3. FIG. 4H-4I show qRT-PCR (FIG. 9H) and western blot (FIG. 9I) analysis of Ctnnb1; β-catenin and Ido1; IDO in BMDCs isolated from wild-type (WT) and β-cat$^{ΔDC}$ mice.

FIG. 11A shows a bar graph of the levels of Kynurenine measured by HPLC analysis of conditioned media harvested from DCs treated with rWnt5a, ETO, or both reagents. n=3. FIG. 11B shows a bar graph of the levels of Kynurenine measured by HPLC analysis of conditioned media harvested from tumor-infiltrating DCs (TIDC) isolated from Braf$^{V600E}$Pten$^{-/-}$-NTC and Braf$^{V600E}$Pten$^{-/-}$-Wnt5a$^{KD}$ melanomas in the presence and absence of ETO. n=3/group. FIG. 11C shows a bar graph of the levels of normalized PpIX intensity as measured by flow cytometry analysis of DCs treated with rWnt5a, ETO, or both reagents following a δ-aminolevulinic acid (ALA) pre-incubation. n=3. The right panel shows a representative flow histogram of PpIX expression based on three independent experiments. FIG. 11D shows a bar graph of the normalized Hemin levels measured by colorimetric assay of DCs treated with increasing concentrations of rWnt5a, with and without ETO. n=3. FIG. 11E shows a bar graph of Alas1 mRNA levels in DCs treated with the indicated reagents based on qRT-PCR analysis. n=3.

FIG. 12A shows a bar graph of the percent of DC-induced CD4$^+$FoxP3$^+$ Treg cells measured by in vitro Treg cell assay in either wild-type or Ido1$^{-/-}$ DCs pre-treated with the indicated combination of reagents, including rWnt5a, ETO, and the antagonistic antibodies anti-IL-6 and anti-IL-12. n=3. FIG. 12B shows bar graphs of Il6 (left) and Il12b (right) mRNA levels in DC2.4-NTC (NTC) and DC2.4-CPT1A$^{KD}$ (CPT1A$^{KD}$) cells based on qRT-PCR analysis. n=3. FIG. 12C shows bar graphs of the concentrations of IL-6 (left) and IL-12p40 (right) in the conditioned media of DC2.4-NTC (NTC) and DC2.4-CPT1A$^{KD}$ (CPT1A$^{KD}$) cells based on ELISA analysis. n=3. FIG. 12D shows bar graphs of Il6 (left) and Il12b (right) mRNA levels in ETO-treated BMDCs based on qRT-PCR analysis. n=3.

FIG. 13E shows a bar graph of IFNγ ELISPOT analysis of TRP2-specific tumor-infiltrating T cells isolated from each treatment group described in FIG. 13C. n=4/group. The right panel shows images of representative IFN-γ ELISPOT plates. FIG. 13F shows a scatterplot of tumor volume over time, representing Braf$^{V600E}$Pten$^{-/-}$ melanoma growth after anti-CD8 antibody-mediated T cell depletion or IgG control followed by ETO treatment. n=6/group. FIG. 13G shows a schematic of the experiment designed to investigate the impact of DC-specific FAO on primary melanoma progression. Pre-treated DCs are transferred into the footpad of syngeneic Braf$^{V600E}$Pten$^{-/-}$ mice 3 days prior to tumor induction with 4-HT (4-hydroxytamoxifen) and every 3 days thereafter for 4 weeks (dashed arrows). FIG. 13H shows a scatterplot of tumor volume over time, representing autochthonous melanoma growth in Braf$^{V600E}$Pten$^{-/-}$ mice undergoing treatment with rWnt5a- treated DCs, with and without ETO, following induction of primary melanoma development using 4-HT. n=5/group. FIG. 13I shows bar graphs of the percent of CD4$^+$FoxP3$^+$ Treg cell (right) and CD8$^+$ T cell (left) populations measured by flow cytometry in tumor-draining lymph node tissue (TDLN) and tumor-infiltrating lymphocytes (TILs), respectively. n=4. All data are mean±SEM. *P<0.05.

DETAILED DESCRIPTION OF THE INVENTION

Figure 2A:
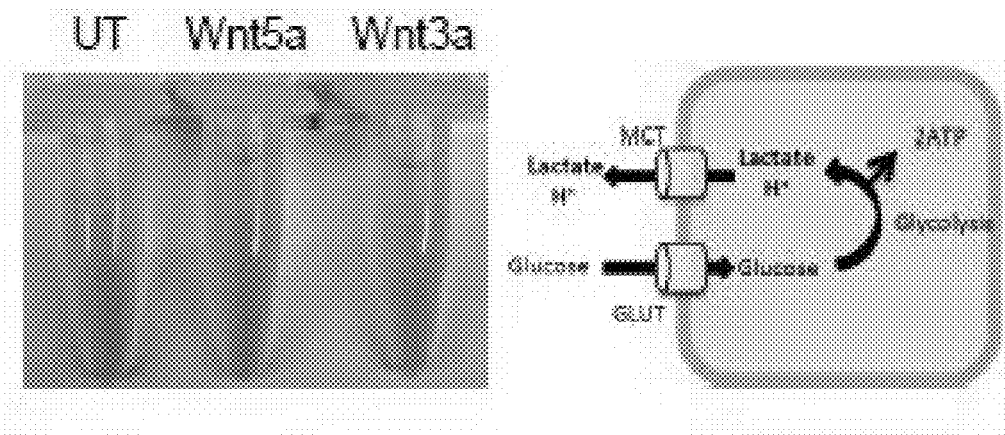
FIG. 2A shows a photograph of microcentrifuge tubes containing BMDCs treated with Wnt5a (200 ng/ml) or Wnt3a (100 ng/ml) for 48 hours in normal growth media containing phenol red. Yellow indicates an acidic pH while red indicates a more neutral pH. The schematic on the right depicts lactate production by BMDCs, including a lactic acid transporter (monocarboxylate transporter, MCT) and a glucose transporter (GLUT).
Figure 2B:
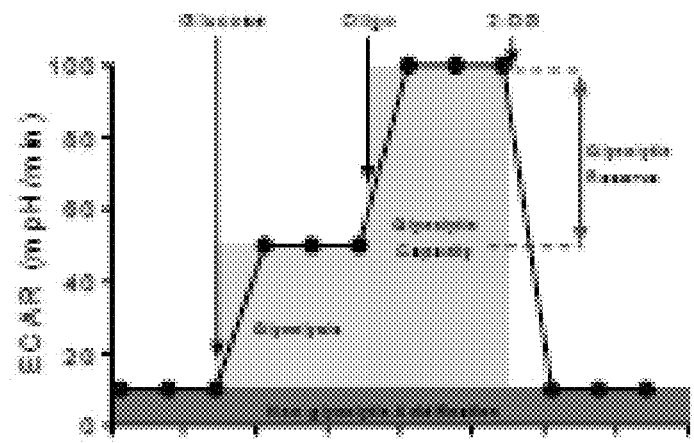
FIG. 2B shows a scatterplot representing the Seahorse XF glycolytic function profile of rWnt5a treated DCs.
Figure 2C:
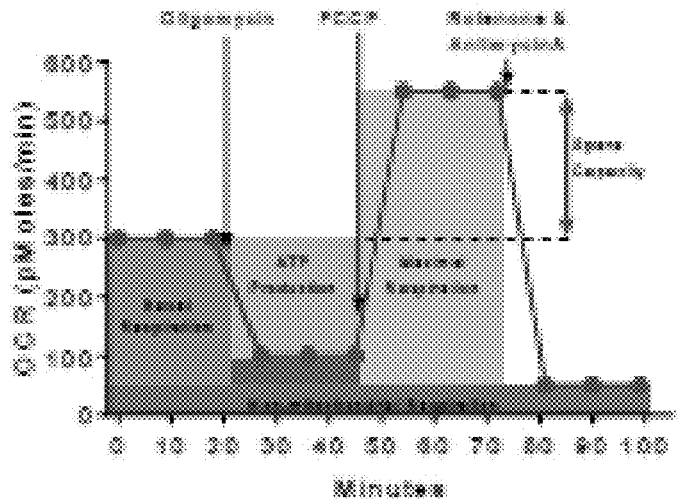
FIG. 2C shows a scatterplot representing the Seahorse XF mitochondrial respiration profile of rWnt5a treated DCs.

The present invention has been described in terms of one or more preferred embodiments, and it should be appreciated that many equivalents, alternatives, variations, and modifications, aside from those expressly stated, are possible and within the scope of the invention. Before the present invention is described, it is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result. The term about as used herein refers to a range of +/−10% of the numerical value listed.

The use herein of the terms "including," "comprising," or "having," and variations thereof, is meant to encompass the elements listed thereafter and equivalents thereof as well as additional elements. Embodiments recited as "including," "comprising/*" or "having" certain elements are also contemplated as "consisting essentially of and "consisting of those certain elements.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Definitions

As used herein, the term "biomarker" refers to a naturally occurring biological molecule present in a subject at varying concentrations useful in predicting the risk or incidence of a disease or a condition, such as cancer. For example, the biomarker can be a protein present in higher or lower amounts in a subject at risk for cancer. The biomarker can include nucleic acids, ribonucleic acids, or a polypeptide used as an indicator or marker for cancer in the subject. In some embodiments, the biomarker is a protein. A biomarker may also comprise any naturally or nonnaturally occurring polymorphism (e.g., single-nucleotide polymorphism [SNP]) present in a subject that is useful in predicting the risk or incidence of wnt-β-catenin-mediated cancer. Specifically, in the present invention, the biomarker is a marker for detecting immunotherapy (e.g., anti-PD-1 immunotherapy)-resistant cancers.

In certain embodiments, the biomarker is selected from the group consisting of wnt5a, CXCL2, CXCL5, CXCR2, HSP70, S100A8, S100A9 and combinations thereof.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results. In some instances, an effective amount is enough to reduce or inhibit tumor cell growth and proliferation.

As used herein, the term "subject" and "patient" are used interchangeably herein and refer to both human and nonhuman animals. In a preferred embodiment, the subject or patient is a human. The term "nonhuman animals" of the disclosure includes all vertebrates, e.g., mammals and non-mammals, such as nonhuman primates, sheep, dog, cat, horse, cow, chickens, amphibians, reptiles, and the like.

The term "biological sample" as used herein includes, but is not limited to, a sample containing tissues, cells, and/or biological fluids isolated from a subject. Examples of biological samples include, but are not limited to, tissues, cells, biopsies, blood, lymph, serum, plasma, urine, saliva, mucus and tears. In one embodiment, the biological sample is a biopsy (such as a tumor biopsy). A biological sample may be obtained directly from a subject (e.g., by blood or tissue sampling) or from a third party (e.g., received from an intermediary, such as a healthcare provider or lab technician).

As is known in the art, a cancer is generally considered as uncontrolled cell growth. The methods of the present invention can be used to treat any cancer, and any metastases thereof, including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulvar cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma. In some embodiments, the cancer comprises a wnt-β-catenin-mediated cancer. In some embodiments, the cancer comprises an immunotherapy-resistant wnt-β-catenin-mediated cancer. In some embodiments, the cancer is resistant to an anti-PD-1 immunotherapy or anti-PDL-1 immunotherapy. In some embodiments, the cancer is resistant to the combination of anti-PD-1 immunotherapy and anti-CTLA-4 immunotherapy. In certain embodiments, the cancer comprises melanoma. Suitable immunotherapy-resistant wnt-β-catenin-mediated cancer include, but are not limited to, for example, melanoma, metastatic melanoma, non-small cell lung cancer, renal cell carcinoma, Hodgkin Lymphoma, squamous cell carcinoma of the head and neck, urothelial carcinoma, colorectal cancer, pancreatic cancer or hepatocellular carcinoma. In a preferred embodiment, the cancer is melanoma.

Methods

The present disclosure is based, in part, of the discovery that tumor-mediated paracrine Wnt-beta-catenin signaling plays an important role in promoting local immune tolerance and driving adaptive resistance to anti-PD-1 antibody immunotherapy. Inventors have shown that the inhibition of Wnt ligand signaling is capable of promoting immune-mediated responses to cancer in vivo and suppressing their progression when administered in combination with anti-PD-1 antibody therapy. Based on these data, we hypothesize that differential expression of various components of the paracrine Wnt-3-catenin signaling pathway that promote downstream signaling in the tumor microenvironment may predict for favorable immunologic responses to Wnt inhibitor therapy. This may include upregulated expression of various Wnt ligands and Fzd receptors as well as the downregulated expression of various negative regulators of this pathway such as WIF1, sFRPs, RNF43 and ZNRF43. The present Examples demonstrate melanomas exhibit elevated Wnt5a expression are associated with resistance to checkpoint inhibitor therapy (anti-PD-1 therapy) which is consistent with a recent outside RNAseq-based study showing that Wnt5a is associated with poor responses to anti-PD-1 antibody immunotherapy. In addition to being a potential marker of general immunotherapy responses, our data indicate that this pathway is likely to be a particularly promising marker for immunotherapies that specifically target the Wnt and IDO pathways, both of which are currently being targeted in clinical trials.

Accordingly, one aspect of the present disclosure provides a method of detecting and determining the presence of a wnt-β-catenin-mediated cancer in a subject comprising, consisting of, or consisting essentially of detecting the amount of at least one biomarker present in a biological sample derived from the subject, wherein the biomarker is associated with wnt-β-catenin-mediated cancer. In a preferred embodiment, the at least one biomarker is selected from the group consisting of wnt5a, CXCL2, CXCL5, CXCR2, HSP70, S100A8, S100A9, YAP1, NPRP3 and combinations thereof. In a preferred embodiment, the marker is HSP70.

In some embodiments, the method comprises comparing the level of the at least one biomarker in a sample before initiation of treatment and then following initiation of treatment with an anti-PD-1 immunotherapy. In a preferred embodiment, the change in level of the marker is determined in peripheral biological sample, for example, blood. In some examples, the change in the level of the biomarker following initiation of treatment is a marker showing the subjects response to the anti-PD-1 therapy.

In one embodiment, the biological sample is a peripheral blood sample. In one example, the biological sample is peripheral blood sample, and the at least one biomarker is HSP70. In some embodiments, the baseline level of the marker in the peripheral sample can be used to as a marker for response to anti-PD-1 antibody therapy.

In another embodiment, the samples is a tumor tissue or tumor biopsy. In one example, the biological sample is tumor tissues and the at least one marker is determined at a baseline level. The baseline level of the marker determined from a tumor sample can be used to determine if a tumor is responsive to the anti-PD-1 immunotherapy or if the tumor is resistant to the anti-PD-1 therapy.

In one embodiment, the detecting comprises quantifying the expression level of at least one biomarker as compared to a control, wherein the increased expression level of the at least one biomarker relative to the control indicates a wnt-β-catenin-mediated cancer.

Another aspect of the present disclosure provides a method of diagnosing a wnt-β-catenin-mediated cancer in a subject comprising, consisting of, or consisting essentially of quantifying the amount of at least one biomarker present in a biological sample derived from the subject, wherein the biomarker is associated with a wnt-β-catenin-mediated cancer.

Another aspect of the present disclosure provides a method of determining the presence of an immunotherapy-resistant wnt-β-catenin-mediated cancer in a subject comprising, consisting of, or consisting essentially of quantifying the amount of at least one biomarker present in a biological sample derived from the subject, wherein the biomarker is associated with an immunotherapy-resistant wnt-β-catenin-mediated cancer.

Another aspect of the present disclosure provides a method of determining the presence of a wnt-β-catenin-mediated cancer in a subject comprising, consisting of, or consisting essentially of: (a) obtaining a biological sample from a subject; (b) determining the expression level of one or more biomarkers that are associated with a wnt-β-catenin-mediated cancer in the biological sample; and (c) comparing the expression level of the biomarkers in the biological sample with that of a control, wherein the presence of one or more of the biomarkers in the sample that is in an amount greater than that of the control indicates the presence of a wnt-β-catenin-mediated cancer. In some further embodiments, the method further comprises (d) administering appropriate anti-wnt-β-catenin-mediated cancer therapy if one or more of the biomarkers are expressed indicating the presence of a wnt-β-catenin mediated cancer.

Another aspect of the present disclosure provides a method of detecting or diagnosing a wnt-β-catenin-mediated cancer in a subject comprising, consisting of, or consisting essentially of: (a) obtaining a biological sample from a subject; (b) determining the expression level of one or more biomarkers that are associated with a wnt-β-catenin-mediated cancer in the biological sample; and (c) comparing the expression level of the biomarkers in the biological sample with that of a control, wherein the presence of one or more of the biomarkers in the sample that is in an amount greater than that of the control indicates a wnt-β-catenin-mediated cancer. In some embodiments, the method further comprises (d) administering appropriate anti-wnt-β-catenin-mediated cancer therapy if one or more of the biomarkers are expressed indicating the presence of wnt-β-catenin-mediated cancer.

Another aspect of the present disclosure provides a method of detecting or determining the presence of an immunotherapy-resistant wnt-β-catenin-mediated cancer in a subject comprising, consisting of, or consisting essentially of (a) determining the expression level of one or more biomarkers that are associated with a wnt-β-catenin-mediated cancer in the biological sample; and (b) comparing the expression level of the biomarkers in the biological sample with that of a control, wherein the presence of one or more of the biomarkers in the sample in an amount greater than that of the control indicates a wnt-β-catenin-mediated cancer. In some embodiments, the method further comprises (c) administering appropriate anti-wnt-β-catenin-mediated cancer therapy if one or more of the biomarkers are expressed indicating the presence of wnt-β-catenin-mediated cancer.

Another aspect of the present disclosure provides a method of detecting or determining the presence of an immunotherapy-resistant wnt-β-catenin-mediated cancer in a subject comprising, consisting of, or consisting essentially of: (a) obtaining a biological sample from a subject; (b) determining the expression level of one or more biomarkers that are associated with an immunotherapy-resistant wnt-β-catenin-mediated cancer in the biological sample; and (c) comparing the expression level of the biomarkers in the biological sample with that of a control, wherein the presence of one or more of the biomarkers in the sample that is in an amount greater than that of the control indicates the presence of an immunotherapy-resistant wnt-β-catenin-mediated cancer. In some embodiments, the method further comprises (d) administering an appropriate anti-wnt-β-catenin signaling pathway inhibitor and an anti-wnt-β-catenin-mediated cancer immunotherapy if an immunotherapy-resistant wnt-β-catenin mediated cancer is detected. In a preferred embodiment, the anti-wnt-β-catenin-mediated cancer immunotherapy is an anti-PD-1 immunotherapy, for example, an anti-PD1 antibody. In another embodiment, the anti-PD-L1 immunotherapy, for example, an anti-PD-L1 antibody that blocks PD-1:PD-L1 interaction. Suitable anti-PD-1 antibodies include antibodies that are capable of blocking PD-1:PD-L1 interaction.

In some embodiments, the anti-PD1 immunotherapy and anti-wnt-β-catenin signaling pathway inhibitor are administered concurrently. In other embodiments, the anti-wnt-β-catenin signaling pathway inhibitor is administered prior to the administration of the anti-PD1 immunotherapy. In yet other embodiments, the anti-wnt-β-catenin signaling pathway inhibitor is administered after the administration of the anti-PD1 immunotherapy.

In some embodiments, the biomarker is selected from the group consisting of wnt5a, CXCL2, CXCL5, CXCR2, HSP70, S100A8, S100A9, YAP1, NPRP3 and combinations thereof.

In another embodiment, the immunotherapy comprises an anti-PD1 immunotherapy, including, for example, an anti-PD-1 antibody.

Suitable PD-1 immunotherapies are known in the art. Suitable anti-PD-1 antibodies include antibodies that are capable of blocking PD-1 binding to a cell. Suitable PD-1 inhibitors include small molecule inhibitors or monoclonal antibodies that bind PD-1 and blocks PD-1 activity. Suitable monoclonal antibodies to PD-1 are known in the art and include, but are not limited to, nivolumab (available commercially as Opdivo® from Bristol Myers Squibb, New York, N.Y.), pembrolizumab (also known as MK-3475 and lambrolizumab; available commercially as Keytruda® from Merck & Co., Kenilworth, N.J.), pidilizumab (also known as CT-011; available commercially from Medivation, Inc., San Francisco, Calif.), BMS 936559 (available commercially from Bristol Myers Squibb, New York, N.Y.), MPDL328OA (available commercially from Roche Holding AG, Basel, Switzerland), REGN2810 (SAR439684, commercially available from Regeneron Pharmaceuticals), AMP-224 (recombinant B7-DC Fc-fusion protein composed of the extracellular domain of the PD-1 ligand programmed cell death ligand 2 (PD-L2, B7-DC) and the Fc region of human immunoglobulin (Ig) G1, commercially available from Amplimmune), MEDI0680 (AstraZeneca), PDR001 (anti-PD-1 antibody available from Novartis), among others. Suitable PD-1 inhibitors and antibodies for immunotherapy can be found, for example, in Alsaab et al., "PD-1 and PD-L1 Checkpoint Signaling Inhibition for Cancer Immunotherapy: Mechanism, Combinations, and Clinical Outcome", Frontiers in Pharmacology, vol. 8, p. 561 (2017), doi: 10.3389/fphar.2017.00561 (ISSN=1663-9812), the contents of which are incorporated by reference in its entirety.

Suitable anti-wnt-β-catenin signaling pathway inhibitors are known in the art that can be used in the practice of the present invention. For example, suitable anti-wnt-β-catenin signaling pathway inhibitors include, but are not limited to, Fzd receptor antagonistic antibodies (e.g, OMP-18R5 (vantictumab, commercially available from OncoMed, see U.S. Pat. Nos. 9,573,998; 8,975,044; 8,507,442; 7,982,013), Wnt ligand traps (Fzd-Ig fusion, e.g., OMP-54R28, see U.S. Pat. Nos. 8,324,361; 7,723,477), PORCN inhibitors (e.g., ETC-159, WNT-C59, CGX-1321, WNT974 (LGK-974), RXC004), dishevelled:Fzd interaction inhibitors (e.g., FJ9), tankyrase inhibitors (e.g., XAV939), Beta-catenin:Bcl9 interaction inhibitors (e.g., SAH-BCL9, 1,4-Dibenzoylpiperazines), endogenous inhibitors (e.g., sFrp, WIF1 (recombinant protein could be delivered; the expression of these endogenous inhibitors could also be induced)), microRNAs (e.g., MircroRNA-374a (Chen X, Jia C, Jia C, Jin X, Gu X: MicroRNA-374a Inhibits Aggressive Tumor Biological Behavior in Bladder Carcinoma by Suppressing Wnt/β-Catenin Signaling. Cell Physiol Biochem 2018; 48:815-826. doi: 10.1159/000491911, incorporated by reference in its entirety), among others.

Figure 22:
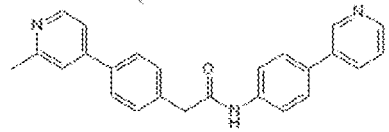
FIG. 22 depicts suitable PORCN inhibitors known in the art.
Figure 22:
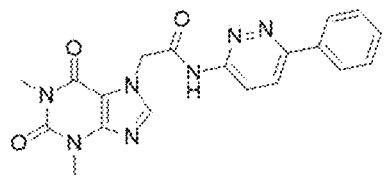
Figure 22:
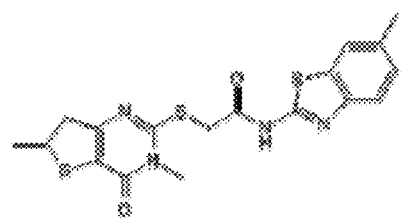
Figure 22:
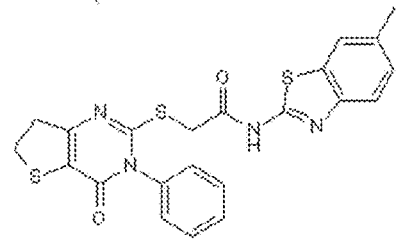
Figure 22:
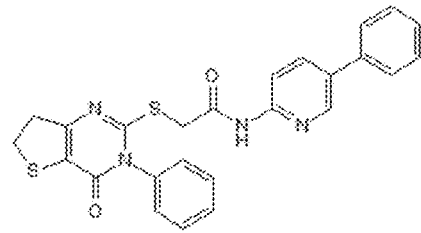
Figure 22:
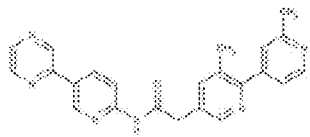
Figure 22:
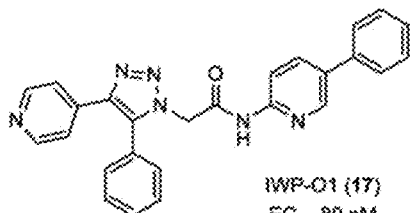
Figure 22:
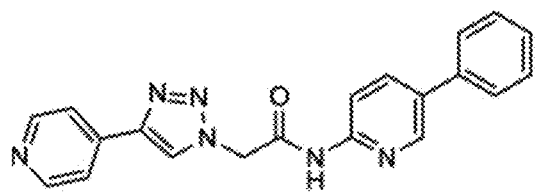

In one embodiment, the anti-wnt-β-catenin signaling pathway inhibitor is a PORCN inhibitor. PORCN inhibitors are known in the art and can inhibit PORCN enzyme activity that effectively suppresses secretion of all Wnt protein ligands. Suitable PORCN inhibitors include, but are not limited to, for example, those demonstrated in FIG. 22, including, LGK974 (available commercially from Novartis, Basel, Switzerland, Liu et al., 2013), ETC-159 (Madan et al., 2016), Wnt-C59 (Proffitt et al., 2013), IWP-2 (Zito et al., 2014), RXC400 (Novel porcupine (PORCN) inhibitor RXC004: Evaluation in models of RNF43 loss of function cancers. Inder Bhamra et al., Journal of Clinical Oncology 2017 35:15_suppl, e14094-e14094, incorporated by reference), CGX-1321 (Curegenix) among others.

In one embodiment, the anti-wnt-β-catenin signaling pathway inhibitor is a Wnt5a inhibitors, for example, antagonistic antibodies that bind to Wnt5a (pAb5a-5), a hexapeptide derived from Wnt5a that can inhibit Wnt5a signaling (commercially available (Wnt Antagonist III, Box 5) from Millipore Sigma), inhibitors of ROR1 and ROR2 (receptors that mediate much of Wnt5a signaling), for example, ROR1/2 antagonistic antibodies (e.g., humanized anti-ROR1 mAb cirmtuzumab (UC-961)), ROR2 tyrosine kinase inhibitors, among others.

Suitable wnt-β-catenin inhibitors include, but are not limited to, for example, ipafricept (also known as OMP-54F28, available commercially from OncoMed Pharmaceuticals, Redwood City, Calif.). which is a fusion protein having a cysteine-rich domain of FZD8 and a human immunoglobulin Fc domain, and vantictumab (also known at OMP-18R5, available commercially from OncoMed Pharmaceuticals, Redwood City, Calif.), a Fzd receptor monoclonal antibody, Xav939 (Huang et al., 2009, Arques et al., 2016), ICG-001 (Emami et al., 2004), PRI-724 (e.g., Zhang et al., Am J Cancer Res. 2015: 5(8): 2344-2360), FJ9 (Fujii et al. Cancer Res. 2007 Jan. 15: 67(2):573-9), SAH-BCL9 (Takada et al., 2012 Sci Transl Med 4(148):148r117) 1,4-Dibenzoylpiperazines (Wisniewski et al., 2016), PAK4 inhibitors, including but not limited to, for example, KPT-9274, KPT-7189, among others.

In some embodiments, the subject is a mammal. In other embodiments, the subject is a human.

In other embodiments, the biological sample is selected from the group consisting of tissues, cells, biopsies, blood, lymph, serum, plasma, urine, saliva, mucus, and tears. In certain embodiments, the sample comprises a biopsy.

In other embodiments, wnt-β-catenin-mediated cancer comprises melanoma.

The present disclosure also provides methods of treating an immunotherapy resistant cancer in a subject, the method comprising: (a) detecting one or more biomarkers in a sample from a subject, selected from the group consisting of wnt5a, CXCL2, CXCL5, CXCR2, HSP70, S100A8, S100A9, YAP1, and NPRP3 and combinations thereof; and (b) if the biomarker is detected, administering a therapeutically effective amount of one or more wnt-p-catenin inhibitors. In a preferred embodiment, the subject is a subject suspected of having a immunotherapy resistant cancer or a subject with cancer previously treated with an immunotherapy In some embodiments, step (a) comprises, detecting one or more biomarkers in a sample and comparing the detection level of the one or more biomarker in the sample with a control, wherein higher expression of the one or more biomarker in the sample as compared to the control indicates the presence of the immunotherapy resistant cancer. In some embodiments, the detecting one or more biomarkers in a sample from a subject, selected from the group consisting of wnt5a, CXCL2, CXCL5, CXCR2, HSP70, and combinations thereof. In some embodiments, the one or more biomarker is detected and the level of expression is quantified. In some embodiments, the immunotherapy resistant cancer is a cancer resistant to anti-PD-1 therapy or anti-PD-L1 therapy. In some embodiments, the cancer is resistant to anti-PD-1 antibody therapy or anti-PD-L1 antibody therapy.

Suitable methods of detecting a biomarker within a sample are known in the art and include, but are not limited to, for example, PCR, q-PCR, qRT-PCR, RT-qPCR, qPCR array, immunoassays, immunohistochemical analysis, ELISpot, enzyme-linked immunosorbent assay (ELISA), gel electrophoresis, surface plasmon resonance (SPR), Mass-sensing BioCD protein array, surface enhanced Raman spectroscopy (SERS), colorimetric assay, electrochemical assay, and fluorescence methods, including, but not limited to, flow cytometry, nanoparticle based detection (e.g., gold nanoparticle bassed detection), protein microarray, quantum dot technology, 9G DNA technology, DNA directed immobilization (DDI), among others.

The present disclosure further provides methods of enhancing an immunotherapy within the subject, the method comprising: (a) detecting one or more biomarkers in a sample from a subject being treated or proposed to be treated with an immunotherapy, wherein the one or more biomarker is selected from the group consisting of wnt5a, CXCL2, CXCL5, CXCR2, HSP70, S100A8, S100A9, YAP1, and NPRP3 and combinations thereof; and (b) if the biomarker is detected, administering a therapeutically effective amount of one or more wnt-β-catenin inhibitors in combination with the immunotherapy. In a preferred embodiment, the subject is a subject undergoing immunotherapy, preferably anti-PD-1 therapy or anti-PD-L1 therapy, for example, anti-PD-1 antibody therapy.

In one embodiment, the detecting one or more biomarkers in a sample from a subject, selected from the group consisting of wnt5a, CXCL2, CXCL5, CXCR2, HSP70, and combinations thereof.

In another aspect, the present disclosure provides methods of enhancing the anti-tumor response to a tumor within a subject, (a) detecting one or more biomarkers in a sample from a subject having a tumor, wherein the one or more biomarker is selected from the group consisting of wnt5a, CXCL2, CXCL5, CXCR2, HSP70, S100A8, S100A9, YAP1, and NPRP3 and combinations thereof; and (b) if the biomarker is detected, administering a therapeutically effective amount of one or more wnt-β-catenin inhibitors in combination with the immunotherapy. In a preferred embodiment, the subject is currently being treated with an immunotherapy. In another embodiment, the subject is proposed to be treated with an immunotherapy. In another embodiment, the subject has a wnt-β-catenin mediated cancer. In some embodiments, the anti-tumor response is a CD8+ T cell response. In one embodiment, the detecting one or more biomarkers in a sample from a subject, selected from the group consisting of wnt5a, CXCL2, CXCL5, CXCR2, HSP70, and combinations thereof.

In another aspect, the present disclosure provides methods of suppressing Gr-MDSC Recruitment in a tumor, the method comprising (a) detecting one or more biomarkers in a sample from a subject having a tumor, wherein the one or more biomarker is selected from the group consisting of wnt5a, CXCL2, CXCL5, CXCR2, HSP70, S100A8, S100A9, YAP1, and NPRP3 and combinations thereof; and (b) if the biomarker is detected, administering a therapeutically effective amount of one or more wnt-β-catenin inhibitors alone or in combination with the immunotherapy. In one embodiment, the detecting one or more biomarkers in a sample from a subject, selected from the group consisting of wnt5a, CXCL2, CXCL5, CXCR2, HSP70, and combinations thereof.

In some embodiments, kits for carrying out the methods described herein are provided. The kits provided may contain the necessary components with which to carry out one or more of the above-noted methods.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The present invention has been described in terms of one or more preferred embodiments, and it should be appreciated that many equivalents, alternatives, variations, and modifications, aside from those expressly stated, are possible and within the scope of the invention.

All publications, patent applications, patents, and other references mentioned herein are incorporated by reference in their entirety. In the case of conflict, the present specification, including definitions, will control. In addition, the materials, methods, and examples are illustrative only and not intended to be limiting.

The invention will be more fully understood upon consideration of the following non-limiting examples.

EXAMPLES

Example 1: Paracrine Wnt5a-β-Catenin Signaling Triggers a Metabolic Program that Drives Dendritic Cell Tolerization Despite recent advances, many cancers remain refractory to available immunotherapeutic strategies. Emerging evidence indicates that the tolerization of local dendritic cells (DCs) within the tumor microenvironment promotes immune evasion. Here, we have described a mechanism by which melanomas establish a site of immune privilege via a paracrine Wnt5a-β-catenin-peroxisome proliferator-activated receptor-γ (PPAR-γ) signaling pathway that drives fatty acid oxidation (FAO) in DCs by upregulating the expression of the carnitine palmitoyltransferase-1A (CPT1A) fatty acid transporter. This FAO shift increased the protoporphyrin IX prosthetic group of indoleamine 2,3-dioxgenase-1 (IDO) while suppressing interleukin(IL)-6 and IL-12 cytokine expression, culminating in enhanced IDO activity and the generation of regulatory T cells. We demonstrated that blockade of this pathway augmented anti-melanoma immunity, enhanced the activity of anti-PD-1 antibody immunotherapy, and suppressed disease progression in a transgenic melanoma model. This work implicates a role for tumor-mediated metabolic reprogramming of local DCs in immune evasion and immunotherapy resistance.

Materials and Methods:

In vivo Animal Studies: C57BL/6J (C57, H-2b), BALB/cJ (H-2d), B6.Cg-Braftm1Mmcm Ptentm1Hwu Tg(Tyr-cre/ERT2)13Bos/BosJ (BrafV600EPten-/-, H-2b), C57BL/6-Tg(TcraTcrb)1100Mjb/J (OT-1, H-2b), and B6.129-Ido1tm1Alm/J (IDO-/-, H-2b) mice were purchased from Jackson Labs. C57BL/6-Foxp3tm1Flv/J (Foxp3-mRFP, H-2b) mice were a gift from H. K. Lyerly (Duke University Medical Center, USA). The CD11c-βcat-/- (βcatΔDC, H-2b) strain was a gift from Santhakumar Manicassamy (Georgia Cancer Center, USA). All experimental groups included randomly chosen littermates of both sexes, ages 6-8 weeks, and of the same strain. Experiments were performed based on a protocol approved by the Institutional Animal Care and Use Committee at Duke University Medical Center.

Figure 6A:
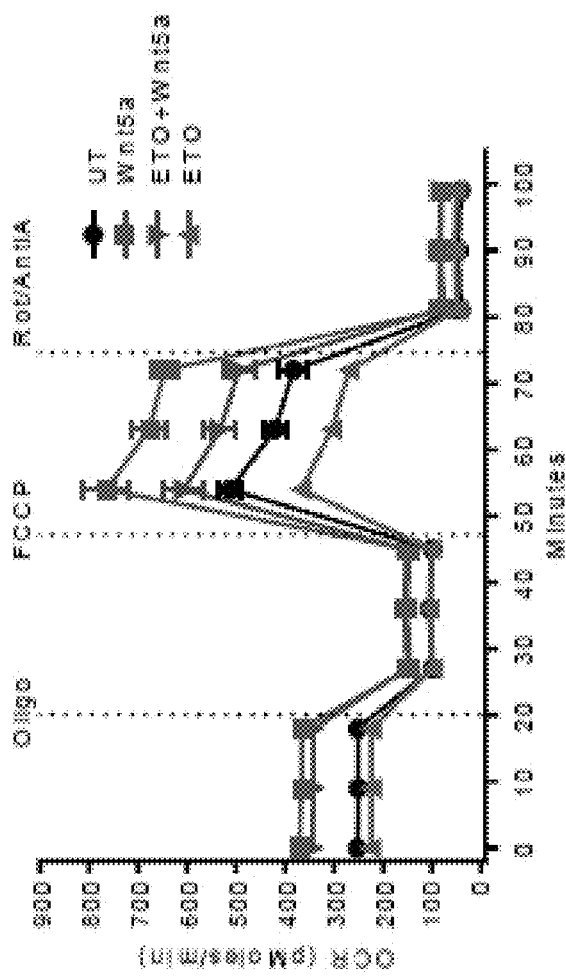
FIG. 6A shows a scatterplot of the measured OCR of human DCs differentiated from harvested peripheral blood mononuclear cells and pre-treated with Wnt5a 48 hours prior to analysis. A short-term incubation with ETO was performed prior to analysis.
Figure 6B:
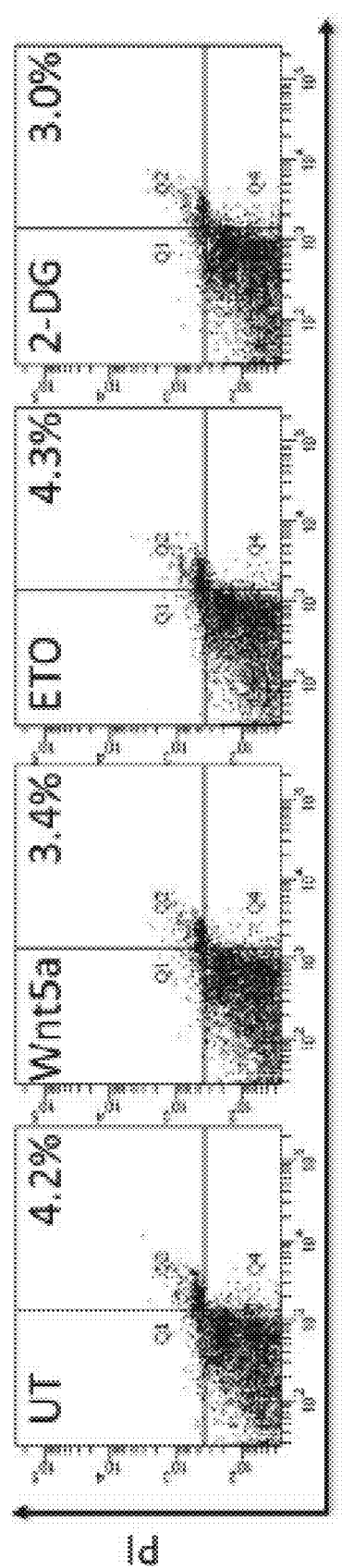
FIG. 6B shows flow cytometry plots of BMDCs treated with the indicated condition for 48 hours, washed, and stained with Annexin V/PI for analysis. These data are representative of 2 independent experiments.
Figure 6C:
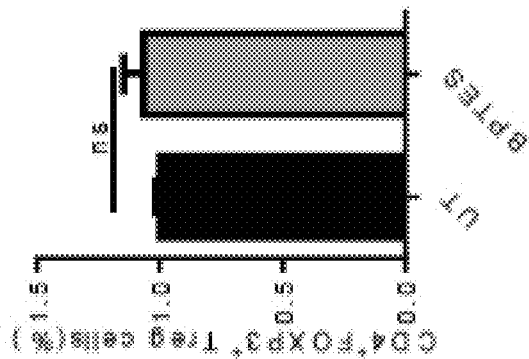
FIG. 6C shows a bar graph of the percent of $CD4^+FoxP3^+$ Treg cells measured after BMDCs were treated with the glutaminase inhibitor BPTES. n=3.
Figure 6D:
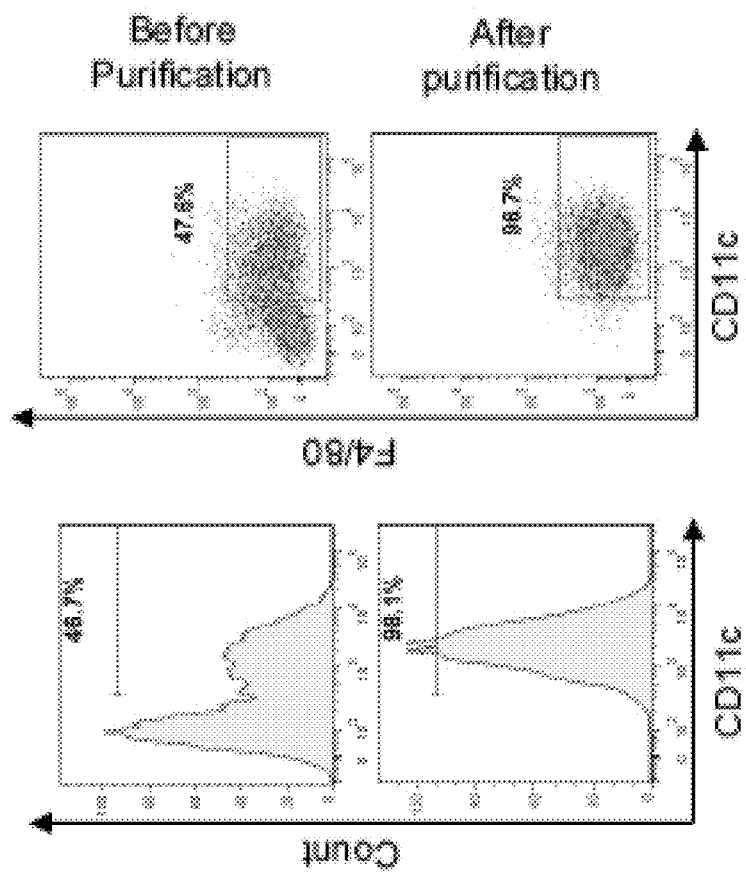
FIG. 6D shows flow cytometry plots used for the purification analysis of DCs isolated using CD1 c microbeads. These data are representative of 6 independent experiments.

Cell Lines: Murine bone marrow-derived dendritic cells (BMDCs) were harvested and differentiated using IL-4 and GM-CSF as previously described (Inaba et al., 1992) and purified using CD11c microbeads (Miltenyi Biotec) according to manufacturer's protocol. DC purity was examined by flow cytometry and consistently found to be >95% CD11c+ F4/80- (FIG. 6D). BrafV600EPten-/-(male), BrafV600EPten-/--Wnt5a-silenced (male), and BrafV600EPten-/--NTC (male) cell lines were generated and cultured as previously described (Holtzhausen et al., 2015). DC2.4, a murine DC line was kindly provided by Dr. Kenneth L. Rock (University of Massachusetts Medical School), and cultured as previously described (Shen et al., 1997). DC2.4-β-catenin-silenced, DC2.4-CPT1A-silenced, and DC2.4-NTC stable cell lines were generated using a β-catenin-targeted, CPT1A-targeted, or control shRNA-expressing lentivirus (Sigma) followed by 3 µg/ml puromycin selection. All cell lines used in this study were tested mycoplasma free by Duke University Cell Culture Facility shared services.

Dendritic Cell Conditioning: DCs were treated with Wnt3a (100 ng/mL), Wnt5a (200 ng/mL), LPS (1 µg/mL), 1-MT (1 mM), 2DG (1 mM), or ETO (100 µM), 2-DG(2-deoxy-d-glucose, 1 mM), Oligomycin (1 µM), succinylacetone (250 µM), or vehicle control either for 24 or 48 hrs prior to their use in both in vitro and in vivo experiments.

Antibodies, Immunoprecipitation, and Immunoblot Analysis: Primary antibodies including CPT1A (Cell signaling), PPAR-γ (Santa Cruz Biotechnology), β-catenin, β-actin (Millipore), p-AMPK(T172)/AMPK (Cell signaling), p-AKT(T308)/Akt (Cell Signaling) were used at 1:1000. Secondary antibodies including goat anti-rabbit IgG-HRP (Millipore) and goat anti-mouse IgG-HRP (Millipore) were used at 1:5000. Cells were lysed in Laemmli sample buffer after treatment and subjected to SDS-polyacrylamide gel electrophoresis and immunoblot analysis. For immunoprecipitation, cells were lysed in radio immunoprecipitation assay (RIPA) buffer [10 mM sodium phosphate (pH 8.0), 150 mM NaCl, 1% Triton X-100, 1% sodium deoxycholate, and 0.1% SDS in the presence of 1 mM DTT, 1 mM phenylmethylsulfonylfluoride, and a protease inhibitor cocktail (Sigma)], precleared with protein A beads, and then incubated with 1 µg of antibody against β-catenin or isotype control IgG with protein A-agarose beads on a rotator overnight at 4° C. After 3 washes with RIPA buffer, immunoprecipitated complexes were eluted in sample buffer by boiling and subjected to immunoblot analysis. Immunoblots were visualized by chemiluminescence substrate (ThermoFisher) and imaged by a ChemiDoc XRSplus system (BioRad).

Flow Cytometry: One million cells were stained with 1 µg per million cells of each fluorochrome conjugated antibodies or commercially available dyes according to the standard protocols and analyzed using a FACSCanto II or LSRII (Becton Dickinson).

RNA Isolation, RT-qPCR, qPCR Array: Total RNA was isolated by RNeasy Plus Mini Kit(Qiagen). RNA(500 ng) were used in cDNA Synthesis (iScript, BioRad). Quantification of mRNA for genes involved in PPARγ signaling was performed using Mouse PrimePCR PPAR Array according to the manufacturer's protocol (BioRad). Real-time PCR was performed using an ABI7500 Real-Time PCR system (Life Technologies). Data analysis utilized the PrimePCR Analysis Software (BioRad). Conventional qPCR was performed using validated primers, and SsoAdvanced Universal SYBR Green Super mix (BioRad) or Taqman probes (Applied Biosystems) for heme synthesis enzymes.

Murine Cell Isolation: Spleens were diced into 1 mm3 pieces and digested with spleen dissociation buffer (Stemcell Technologies) for 30 minutes at room temperature. Tumors were resected and mechanically disaggregated by gentleMACS (Miltenyi) and digested with RPMI containing collagenase IV (1 mg/ml), hyaluronidase (0.1 mg/ml), and deoxyribonuclease (20 U/ml, Sigma) at 37° C. for 1 hour. A 40-micron filter was used to obtain a single cell suspension for downstream applications. DCs were purified using CD11c microbeads and naive CD4 T cells were obtained using a naive T cell isolation kit (Stemcell Technologies). All cell populations were verified for purity by flow cytometry based on a CD45+CD11c+F4/80-IAb/d+ and a CD3+CD4+CD62L+ profile, respectively.

Human Monocyte-derived Dendritic Cells: Human monocyte-derived DCs were generated as previously described (Nair et al., 2012).

ELISPOT: Single cell suspension of tumors were plated at 500,000/well on ELISPOT plate and incubated for 48 hours. Mouse IFNγ ELISPOTPLUS (MABTECH) was performed according to manufacture guidelines. Imaging was conducted using a CTL Immunospot S5 core (Immunospot) and quantified using ImmunoCapture and ImmunoSpot software (Immunospot).

ELISA: Murine IL-6 (eBioscience) and IL-12p40 (Becton Dickinson) ELISAs were performed according to manufacturer's protocol.

Immunohistochemistry/Immunofluorescence: Paraffin-embedded tissues were processed and stained following standard protocols and imaged with a Zeiss CLSM 700 confocal microscope. CD8 (BioLegend) and PD-L1 (Abcam) primary antibodies were utilized where indicated. Warp Red chromogen detection system (BioCare) was used for antigen visualization.

T Cell Proliferation Assay: Splenocytes of OT-1 mice (H-2b) were isolated and stained with CellTrace Violet (ThermoFisher). Preconditioned DCs were loaded with ovalbumin peptide SIINFEKL, and co-cultured at a DC:splenocyte ratio of 40,000:120,000 cells for 72 hrs. CD8+ T cell proliferation was measured by the dilution of Cell Trace Violet dye by flow cytometry.

Treg Cell Assays: For in vivo Treg cell assays, DCs (C57, H-2b) were pre-treated for 48 hours and delivered by intradermal injection into the footpad of Foxp3-mRFP mice. Draining inguinal and popliteal lymph nodes were resected 5 days later and analyzed for CD4+Foxp3+ Treg cells. For in vitro Treg cell assays, DCs (Balb/c, H-2d) were pretreated for either 24 or 48 hrs, and re-plated at a 1:3 DC:T-cell ratio with purified allogeneic naive Foxp3-mRFP (H-2b) CD44loCD62LhiCD4+ Tcells. These co-cultures were incubated for 6 days and quantitated for CD4+FoxP3+ Treg cells by flow cytometry.

BODIPY and Fatty Acid Uptake Assay: DCs were stained in 0.5 µg/ml BODIPY 493/503 in PBS for 15 min to determine neutral lipid content (Herber et al., 2010). Fatty acid uptake measurement in DCs were performed using a dodecanoic acid fluorescent TF2-C12 fatty acid (Sigma) according to the manufacturer's protocol.

Lactate measurement: L-Lactate was measured by lactate dehydrogenase conversion of L-lactate+NAD+ to pyruvate+ NADH following treatment with hydralazine (Pesce et al., 1975). Lactate standards and samples were read at NADH specific absorbance 340 nm. For lactate measurement in Wnt5a time course, BMDCs were seeded in a 48-well plate at 1 million cell per well. BMDCs were treated with 100 ng/ml of recombinant Wnt5a from 0 to 48 hours. For extracellular lactate determination, 0.5 ml of supernatant media was collected directly from the culture, deproteinized by polyethylene glycol precipitation (25% w/v PEG-8000, sigma), and clarified by centrifugation at 20,000 g for 5 min. For intracellular lactate determination, Cells were washed with ice cold PBS, scraped off in 100 µl Milli-Q water (4° C.), freeze (−80° C.) thawed repeatedly 3 times for efficient cell lysis, and then deproteinized as described above. L-lactate was measured by lactate dehydrogenase (LDH, final 2 U/ml, Sigma) conversion of L-lactate+NAD+(β-Nicotinamide adenine dinucleotide, Sigma) to pyruvate+NADH in Glycine Buffer solution (final concentration Glycine 0.2M, Hydrazine 0.17M to destroy pyruvate allowing reaction to run to complete oxidation of lactate, Chloroform 0.0125%, Sigma). Reaction was incubated at 37° C. for 30 minute (without CO2), L-lactate standards and samples were read at NADH specific absorbance 340 nm (Infinite 200 PRO, Tecan).

Cellular Energy Metabolism Analysis: DC energy metabolism was measured using the XFe24 extracellular flux analyzer (Seahorse Bioscience), with the glycolysis stress test kit and the mitochondrial stress test kit as previously described (Everts et al., 2014, Zhao and Klimecki, 2015). For experiments involving LPS injection, DCs were plated in XFe24 plates (200,000/well in 500p1) and treated with LPS for 48 hours prior to XF analysis. DCs were washed and analyzed in XF media (RPMI without sodium bicarbonate, 10 mM glucose, 1% FBS, 2 mM L-glutamine). ECAR was analyzed in real-time with or without LPS stimulation. For experiments involving BrafV600EPten−/− cell line-derived conditioned media (CM), collected CM was concentrated and desalted with an Amicon Ultra 30K filter according to manufacturer's recommendations (Milipore). Final concentrate was further washed with XF media 3 times, added to DCs immediately prior to OCR analysis. For standard ECAR analysis, XF media (without glucose) was used to wash cells prior to the assay. A final concentration of 10 mM glucose, 1 µM oligomycin, 50 mM 2-DG(sigma) were injected through XFe24 port A-C. For standard OCR analysis, XF media (with 10 mM glucose) was used to wash cells, a final concentration of 1 µM oligomycin, 1.5 µM FCCP (fluoro-carbonyl cyanide phenylhydrazone), 100 nM rotenone, and 1 µM of antimycin-A (Sigma) were injected through XFe24 port A-C.

IDO enzymatic assay and Hemin assay: DC IDO enzyme activity was measured by the conversion of L-tryptophan to L-kynurenine in conditioned media by HPLC (Pallotta et al., 2011). Intracellular hemin was measured using a colorimetric assay kit (BioVision).

PpIX Analysis: DCs were terminally incubated in the presence of 1 mM δ-aminolevulinic acid (ALA) for 4 hrs. Intracellular PpIX was analyzed by flow cytometry as previously described (Hryhorenko et al., 1998).

Metabolomics: Metabolites were extracted from 5×106 BMDCs and subjected to LC-MS analysis according to a previously published protocol (Liu et al., 2014a, Liu et al., 2014b). Metabolites were extracted from 5×106 BMDCs from each experimental group (3 mice per group), washed with ice cold PBS, and lysed in 80% (v/v) methanol on dry ice. Cell lysates were frozen at −80° C. for 15 minutes to disrupt cell membrane and quench enzymatic activity. Samples were then thawed on ice, vortexed rigorously to extract metabolites, and then centrifuged at 20,000 g at 4° C. to precipitate proteins and cell debris. Metabolite extracts were then dried using a speed vacuum and subjected to LC-MS analysis (Liu et al., 2014a, Liu et al., 2014b). Data collected from LC-Q exactive MS is processed on Sieve 2.0 (Thermo). For metabolite analysis, theoretical m/z and retention time of 263 known metabolites were used for positive mode, and 197 metabolites were used for negative mode. Data containing detected m/z and relative intensity of different samples were obtained.

Soft Agar Colony Formation Assay: Complete growth media—0.7% agar was overlaid with complete growth media—3.5% agar containing 10,000 cells and additional complete growth media. After 2 weeks, colonies were stained with MTT (Sigma) to identify viable colonies and imaged by a ChemiDoc XRSplus system as previously described (Zhao et al., 2014). Images were analyzed with NIH ImageJ to enumerate colony number.

Figure 14A:
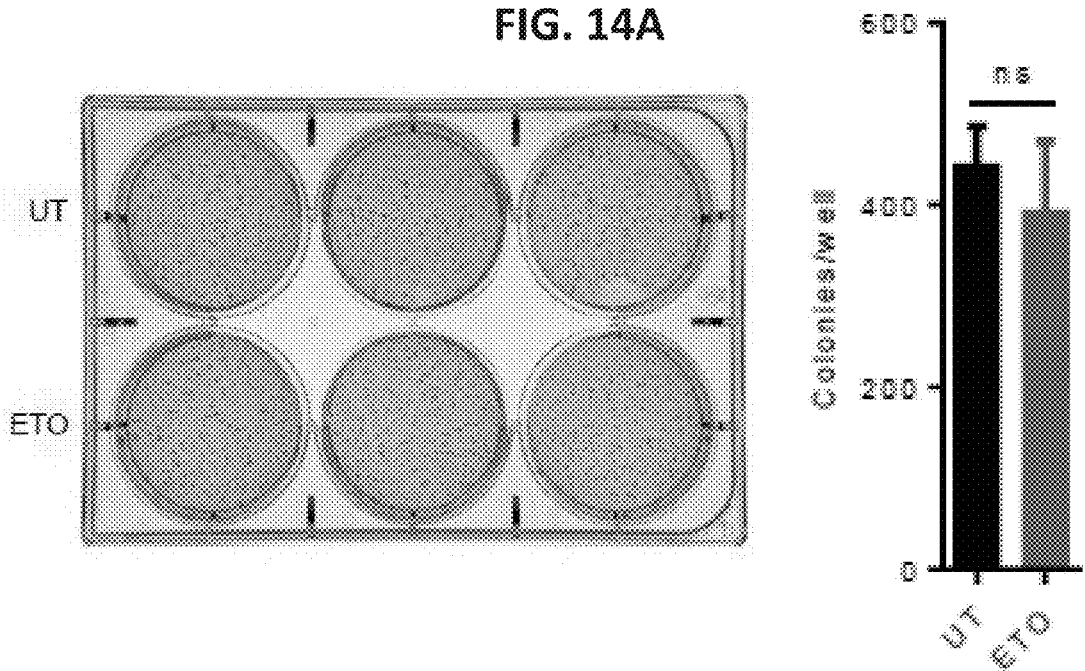
FIG. 14A shows a photograph of a 6-well plate in which BRAF$^{V600E}$PTEN$^{-/-}$ cells were allowed to form colonies in soft agar for 15 days in the absence (UT, untreated) or presence of ETO and then stained with MTT. The right panel shows a bar graph of the quantitation of viable colonies based on ImageJ analysis.
Figure 14B:
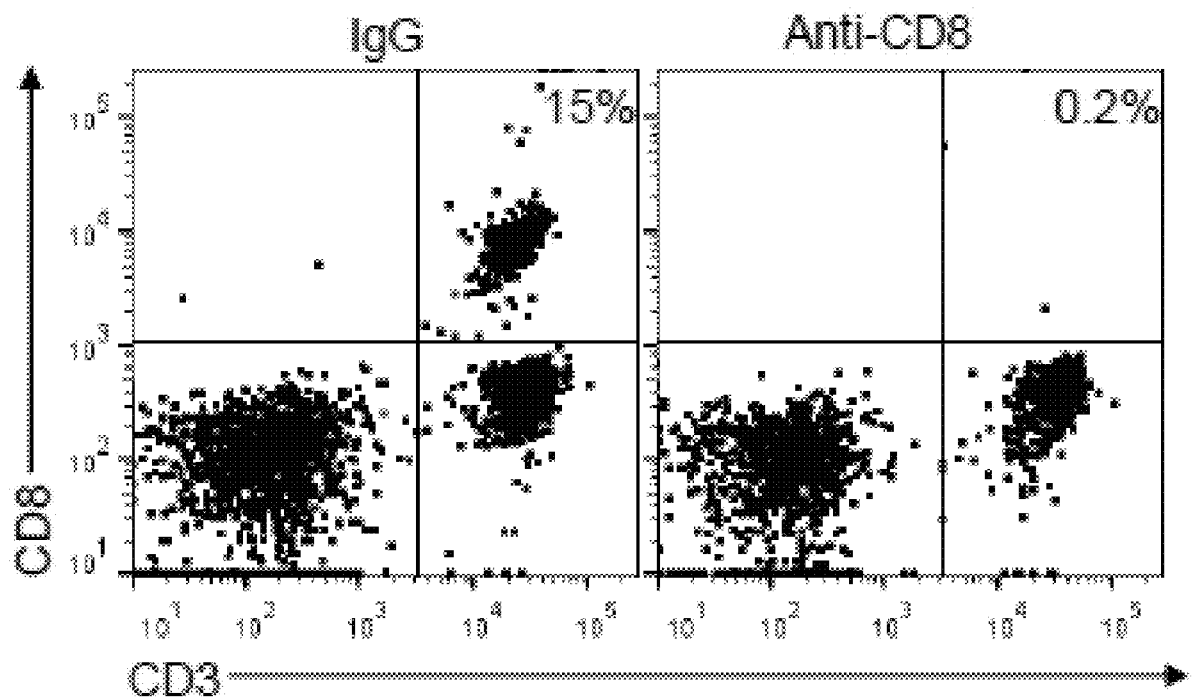
FIG. 14B shows flow cytometry plots quantifying CD8$^+$ T cell depletion. C57BL/6J mice were injected intraperitoneally with anti-CD8 antibody and blood was collected after seven days for analysis.

In vivo CD8 Depletion: Hybridoma clone 53-6.7 was expanded at the Duke Cell Culture Facility in hollow fiber cartridges; 10 ml of serum free supernatant was harvested every 2 days. Anti-mouse CD8 antibody was purified by Pierce Gentle Ag/Ab Binding and Elution Buffer Kit according to manufacturer protocols (ThermoFisher). Antibody concentration was determined by BCA protein assay. Anti-CD8 mAb or IgG isotype control was delivered daily for the first three days then every 7 days thereafter by intraperitoneal injection (500 µg/mouse/dose). CD8 depletion was verified by flow cytometry (FIG. 14B).

Syngeneic Transplant Tumor Studies: BrafV600EPten−/− cells line were established as previously described (Holtzhausen et al., 2015). 5×105 cells were implanted by subcutaneous injection into syngeneic C57BL/6 mice. Tumor growth was monitored by caliper measurement. Etomoxir (Sigma, ETO) was administered daily by oral gavage (25 mg/kg/day) (Collier et al., 1993). Anti-PD-1 rat mAb or rat IgG2a isotype control (BioXCell) was delivered every 3 days by intraperitoneal injection (250 µg/dose).

Autochthonous Tumor Studies: B6.Cg-Braftm1Mmcm Ptentm1Hwu Tg(Tyr-cre/ERT2 H-2b)13Bos/BosJ (BrafV600EPten−/−, H-2b), transgenic mice were subdermally injected with 4-HT (Sigma, 38.75 μg/mouse) to induce primary melanoma development. Three days prior to 4-HT injection, 1×106 cells DCs pretreated with Wnt5a+/− ETO were washed and delivered by intra-dermal injection into the hind leg foot pad every 3-4 days until the conclusion of the experiment. Melanoma growth was monitored by orthogonal caliper measurements every 3-4 days between day 15 to day 32.

Specific statistical tests are reported in the Brief Description of the Drawings. GraphPad Prism 7 Windows version was used for all statistical analyses. Unpaired t-test were used to compare mean differences between control and treatment groups. Univariate ANOVA followed by Tukey's post hoc test were performed to analyze data containing three or more groups. For time lapse extracellular flux analysis repeated measures ANOVA analysis was performed.

Results:

Melanoma-Derived Wnt5a Reprograms DC Energy Metabolism

Figure 2D:
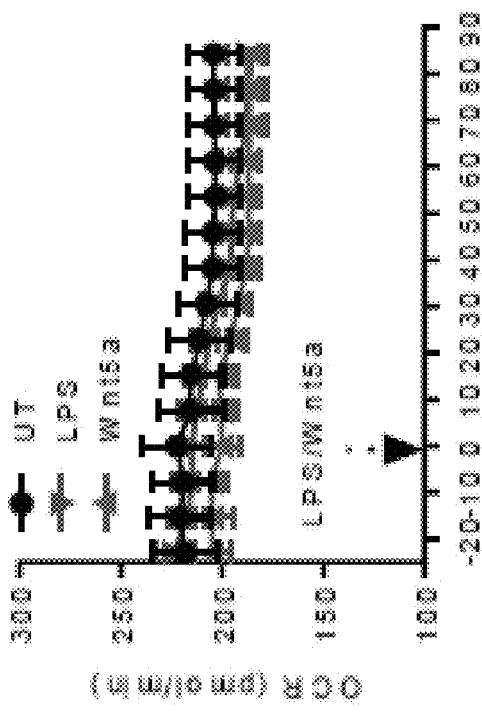
FIG. 2D shows a scatterplot of the measured ECAR of DCs pre-treated with LPS or Wnt5a. A black arrow indicates the injection of LPS (final 1 g/ml) or Wnt5a (final 200 ng/ml). n=3.
Figure 2E:
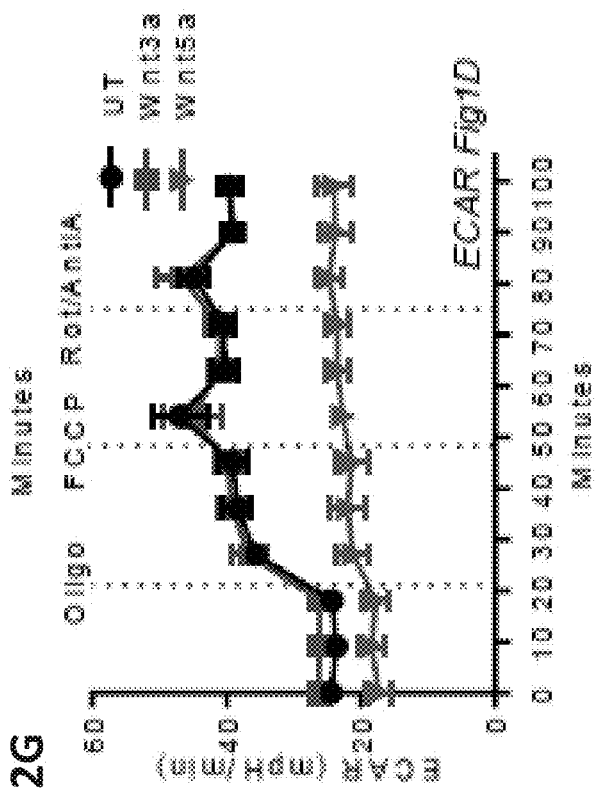
FIG. 2E shows a scatterplot of the simultaneous OCR collected with the data presented in FIG. 2D.
Figure 2F:
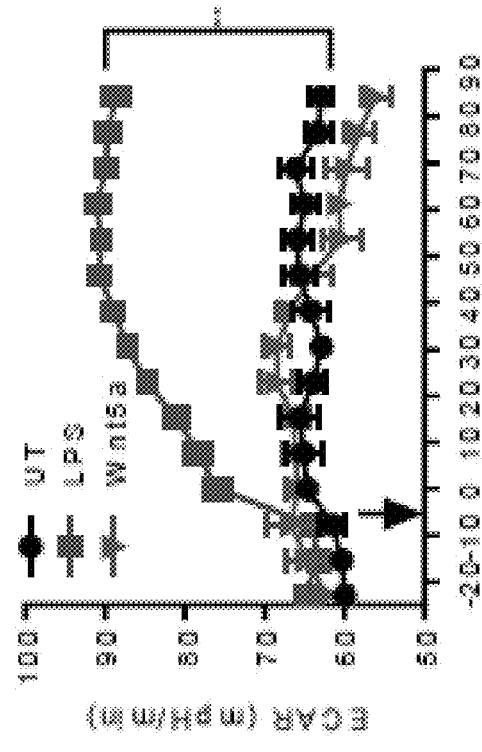
FIG. 2F shows a scatterplot of the simultaneous OCR collected with the data presented in of FIG. 1C.
Figure 2G:
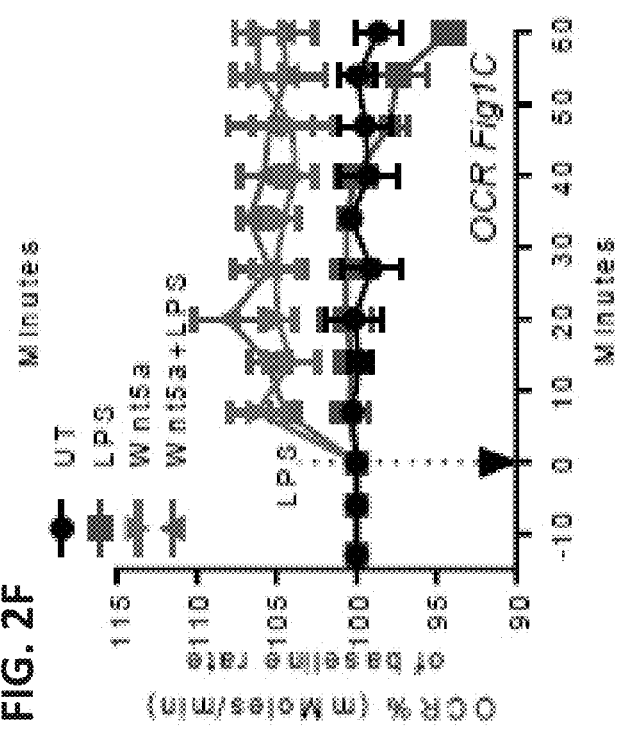
FIG. 2G shows a scatterplot of the simultaneous ECAR collected with the data presented in FIG. 1D.
Figure 2H:
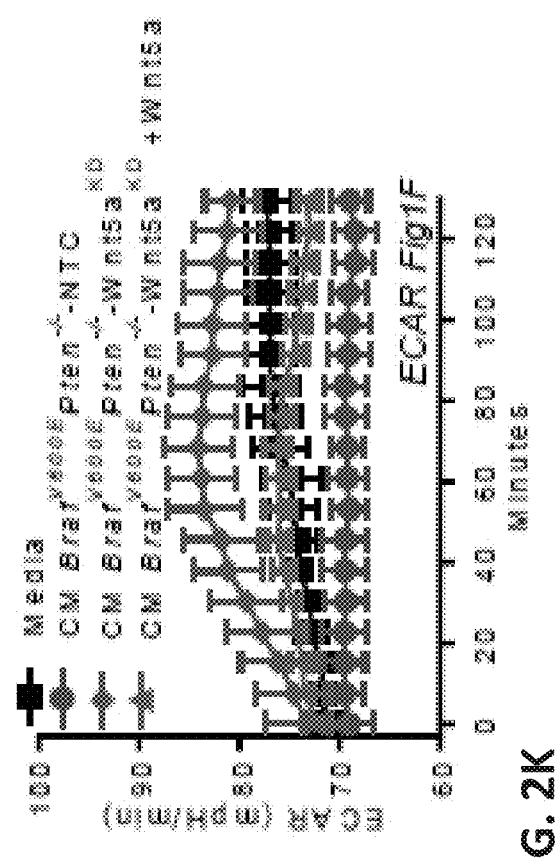
FIG. 2I shows a scatterplot of the simultaneous ECAR collected with the data presented in FIG. 1F.
FIG. 2J shows two bar graphs depicting qRT-PCR quantification of Hk and Pfk1 expression in DCs treated with Wn5a or Wnt3a. n=3.
FIG. 2K shows a scatterplot of the simultaneous ECAR collected with the data presented in FIG. 1G. All data is mean+/−SEM. *P<0.05.
Figure 2J:
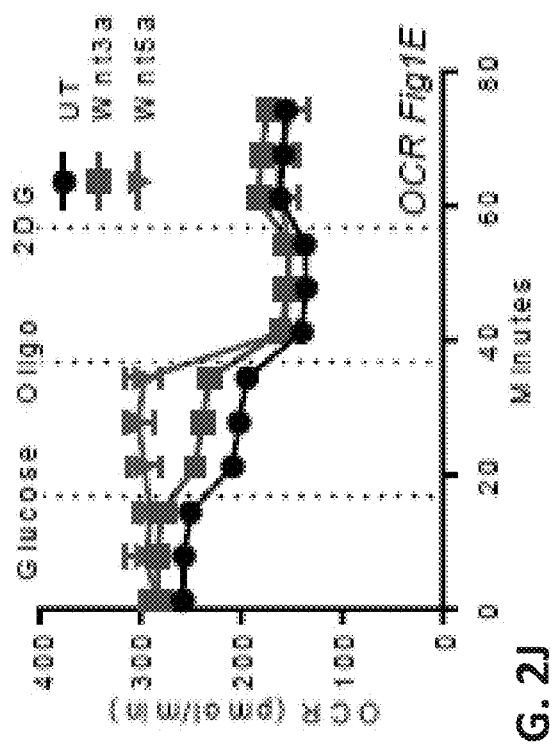
Figure 2I:
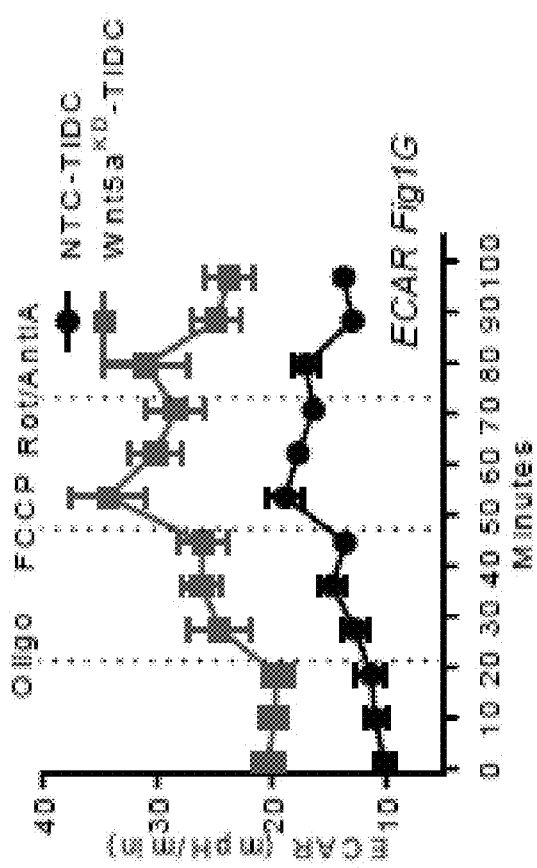
Figure 2K:
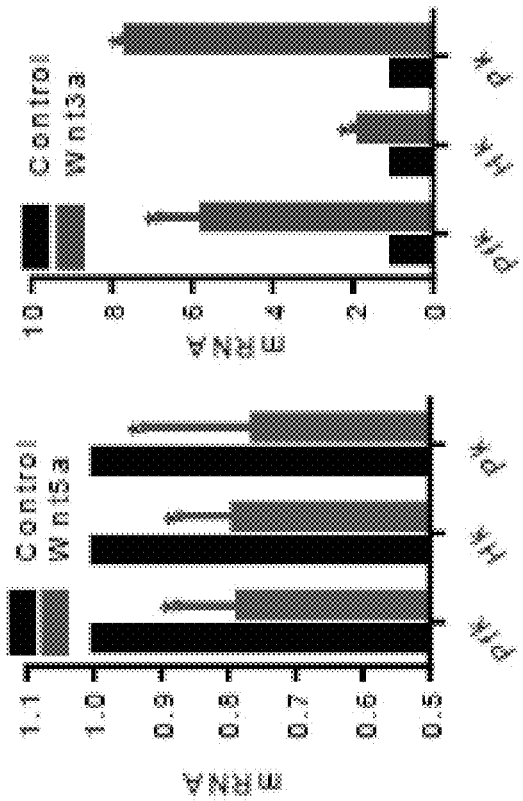

Toll-like receptor (TLR)-induced DC maturation involves the induction of glycolysis (Krawczyk et al., 2010). We have shown that melanoma-expressed soluble Wnt5a signals via the β-catenin signaling pathway to drive DC tolerization (Holtzhausen et al., 2015). Others have also shown Wnt5a regulates cellular metabolism (Sherwood et al., 2014). Based on these findings, we sought to investigate whether Wnt5a alters the metabolism of DCs and whether this may contribute to DC tolerization. Using a biochemical extracellular lactate assay as a surrogate for glycolysis, we found that Wnt5a suppresses lactate production by bone-marrow-derived DCs (BMDCs) (FIG. 1A and FIG. 2A). Further monitoring of the extracellular acidification rate (ECAR) demonstrated that Wnt5a failed to impact glycolysis within 90 min of stimulation, suggesting that Wnt5a may regulate the glycolysis of DCs via a transcriptional mechanism (FIG. 2D-2E). Indeed, qRT-PCR studies revealed that Wnt5a downregulated the expression of the rate-limiting glycolytic enzymes, hexokinase (Hk) and phosphofructokinase-1 (Pfk1), in DCs after 4-8 hr of stimulation (FIG. 1B). Additional ECAR studies demonstrated that Wnt5a pretreatment suppressed the lipopolysaccharide (LPS)-induced glycolytic surge typically observed during the DC maturation program, indicating that Wnt5a elicits a dominant metabolic effect on DCs (FIG. 1C and FIG. 2F). Given the observed effect on glycolysis in DCs, we investigated the impact of Wnt5a on DC oxidative phosphorylation (OXPHOS). These studies demonstrated that recombinant Wnt5a (rWnt5a) effectively promoted OXPHOS in DCs (FIGS. 1D-1E, FIGS. 2B-2C, and FIGS. 2G-2H). To determine whether melanoma-derived Wnt5a was capable of influencing DC metabolism, we analyzed the oxygen consumption rate (OCR) and ECAR of purified DCs stimulated with conditioned media harvested either from a control BrafV600E-Pten−/− melanoma cell line (BrafV600E-Pten−/−-NTC) or a BrafV600E-Pten−/− melanoma cell line genetically silenced for Wnt5a expression (BrafV600E-Pten−/−-Wnt5a-silenced) (Holtzhausen et al., 2015). These studies showed that genetic silencing of Wnt5a diminished the ability of melanomas to promote OXPHOS in DCs, an effect that was partially reversed with the addition of rWnt5a (FIG. 1F and FIG. 2I). These data suggest that melanoma-derived Wnt5a promotes OXPHOS in DCs in vitro. However, no changes in either OXPHOS or glycolysis in DCs were observed following Wnt3a treatment (FIGS. 1D-1E, FIGS. 2G-2H, and FIG. 2J). To verify that melanoma-derived Wnt5a can modulate DC metabolism in vivo, we purified tumor-infiltrating DCs from both BrafV600E-Pten−/−-NTC and BrafV600E-Pten−/−-Wnt5a-silenced tumors resected from syngeneic mice and measured their real-time OCR. Consistent with our previous findings, this study demonstrates that melanoma-derived Wnt5a promotes DC mitochondrial respiration in situ (FIGS. 1G-1H and FIG. 2K). Together, these data reveal that melanoma tissues shift the metabolism of local DC populations from a glycolytic state toward OXPHOS in a Wnt5a-dependent manner.

Wnt5a-Mediated Metabolic Reprogramming Alters DC Function

Figure 3A:
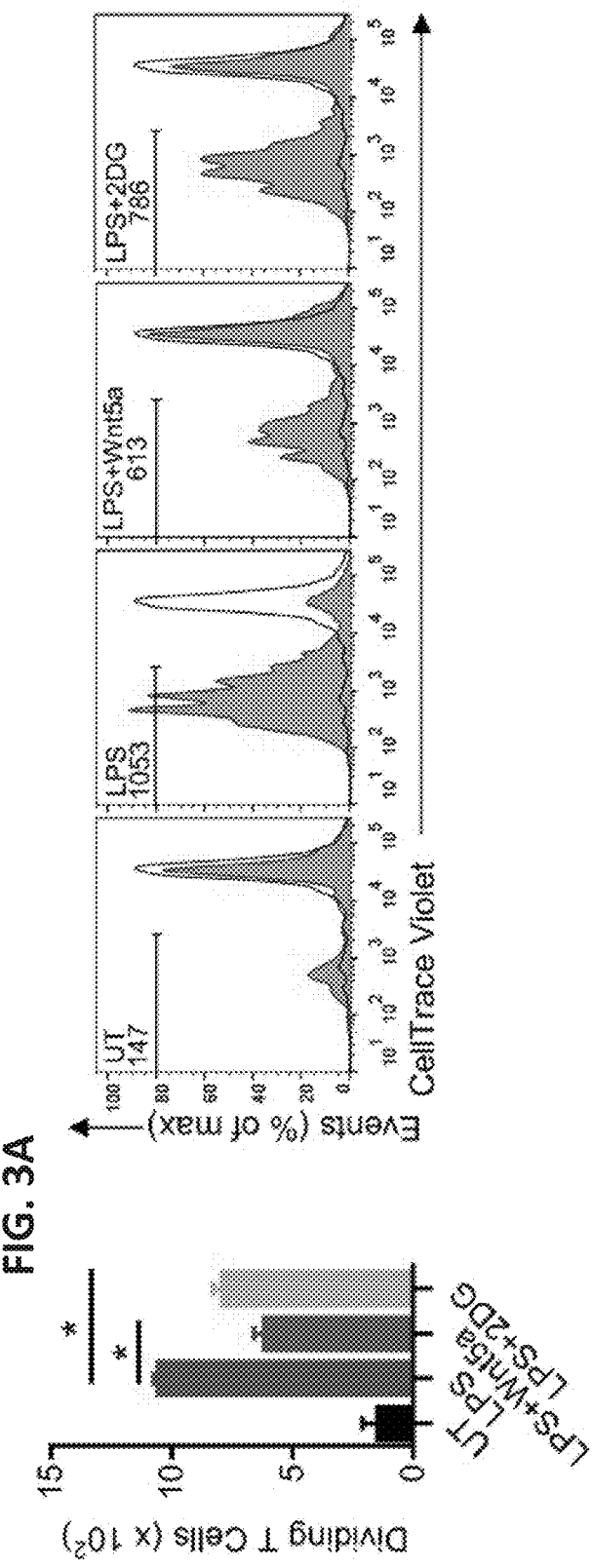
FIG. 3A shows a bar graph of the number of dividing $CD3^+CD^+$ T cells as measured by CellTrace Violet (CTV) dilution. DCs were loaded with OVA257-264 peptide, pre-treated with rWnt5a or 2DG, stimulated with LPS, and co-incubated with OT-I splenocytes. Untreated (UT) cells serve as a control. n=3. The right panel shows representative flow cytometry CTV dilution assay profiles based on three independent experiments, gated on $CD^{3+}CD^{8+}$ T cells.
Figure 3B:
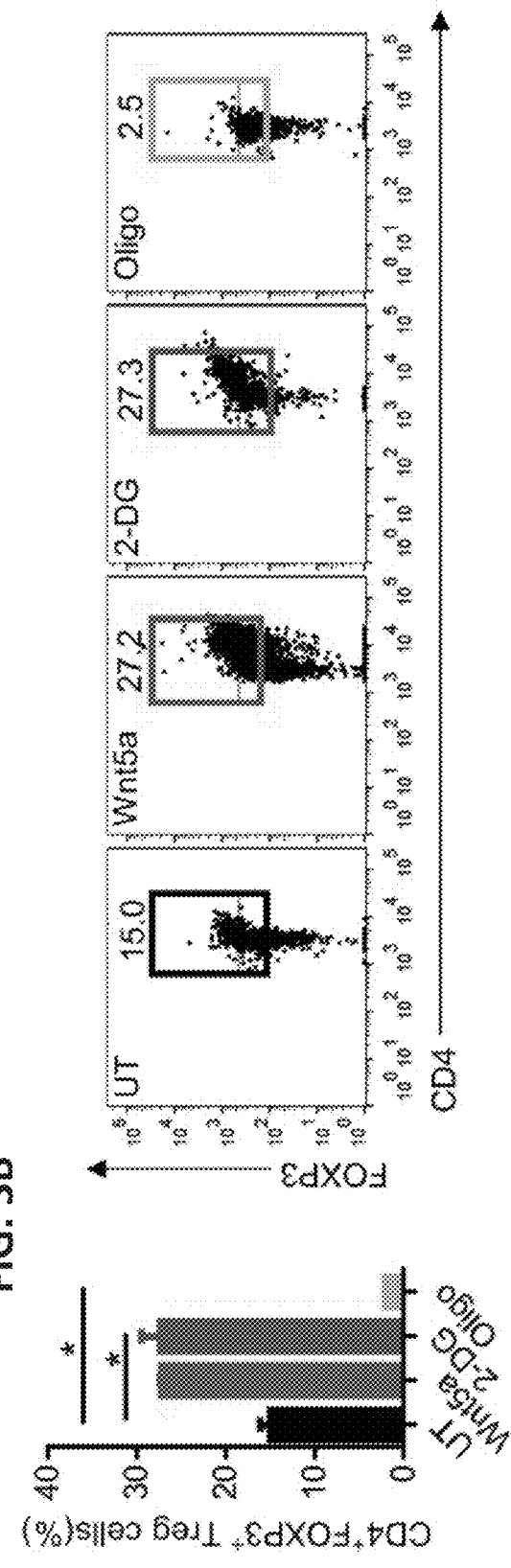
FIG. 3B shows a bar graph of the percent of DC-induced $CD4^+FoxP3^+$ Treg cells as measured by in vitro Treg cell assay after DCs were treated with Wnt5a, 2-DG, or Oligo. n=3. The right panel shows representative flow cytometry plots based on three independent experiments.
Figure 3C:
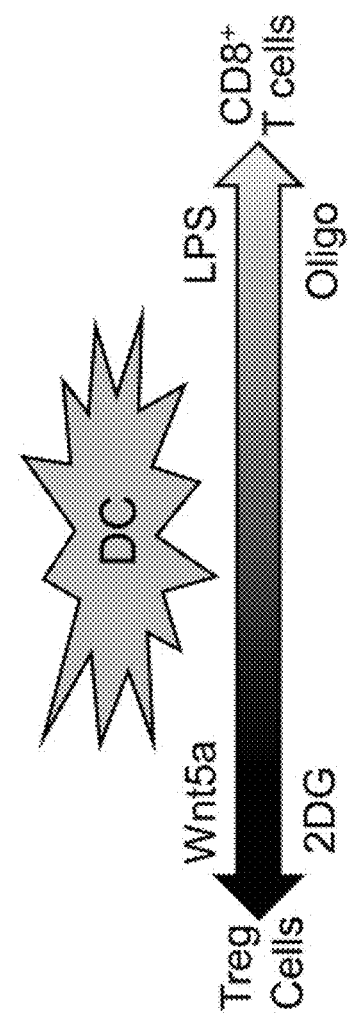
FIG. 3C shows a flow cytometry plot and a bar graph indicating the percent of DC-induced $CD4^+FoxP3^+$ Treg cells detected in inguinal lymph nodes. This analysis was based on three independent experiments with four mice/group.
Figure 3D:
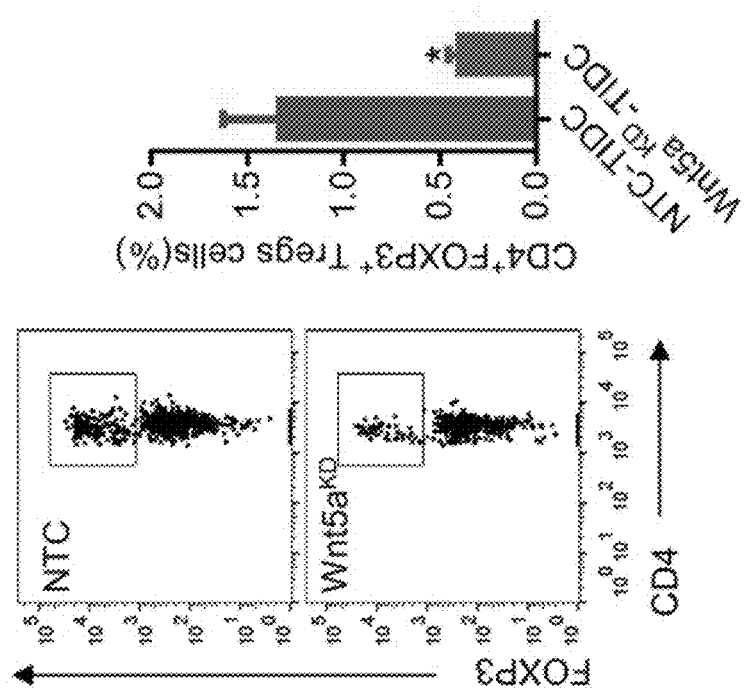
FIG. 3D shows a schematic illustrating the dynamic spectrum of DC-induced T cell responses based on their metabolic alteration. All data are mean±SEM. *P<0.05.
Figure 4:
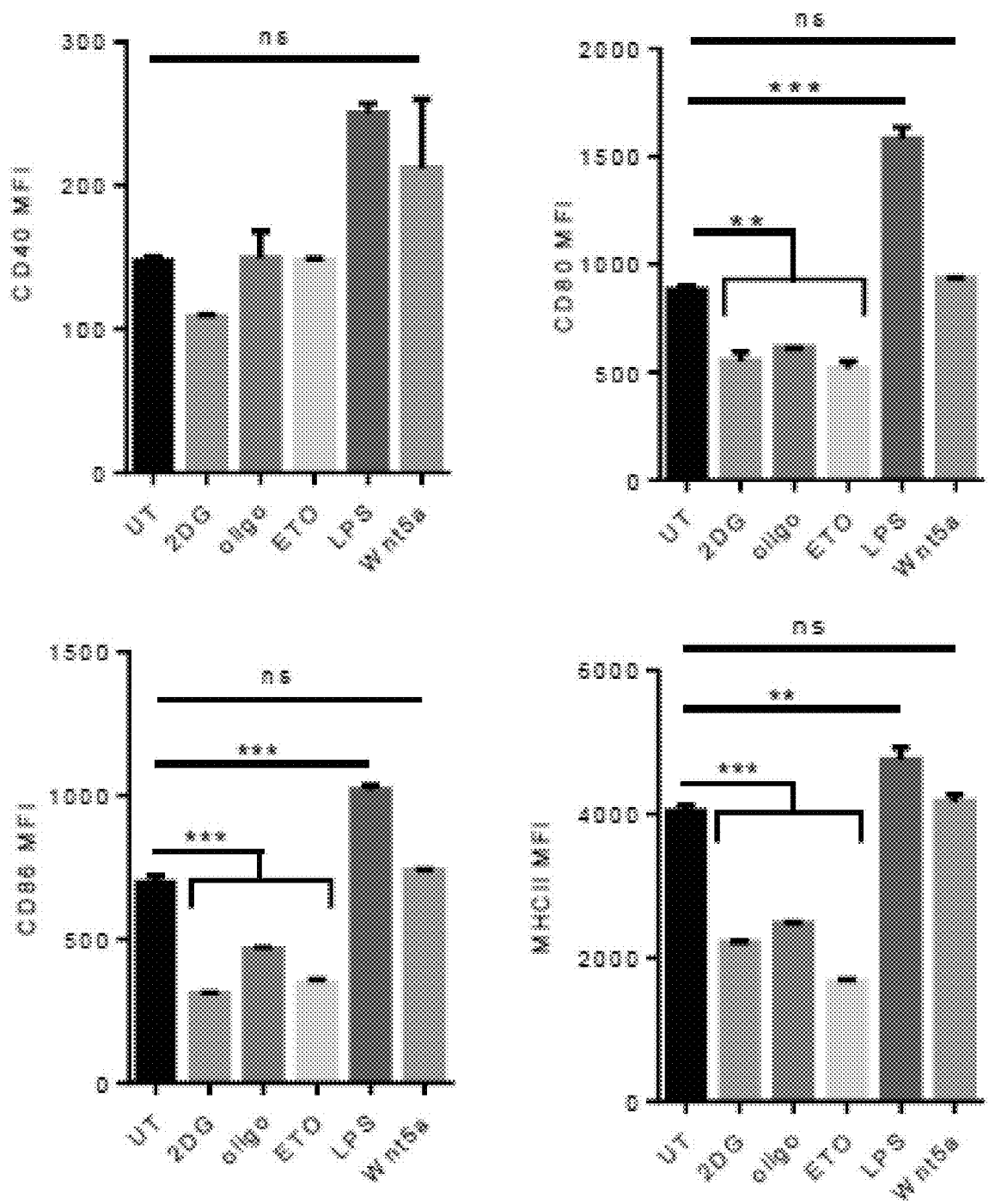
FIG. 4 shows four bar graphs with the expression levels (mean fluorescence intensity, MFI) of the indicated surface marker in DCs treated with 2DG, oligomycin, ETO, or LPS for 24 hours or with Wnt5a for 48 hours, as indicated. n=3. *P<0.05, P<0.005, *P<0.0005.

Previous studies have demonstrated that inhibition of hexokinase, the initial enzyme in the glycolytic pathway, suppresses DC-induced T cell proliferation, while others have found tolerized DCs to exhibit enhanced OXPHOS (Everts et al., 2014, Malinarich et al., 2015). Consistent with these findings and our data showing that Wnt5a blocks LPS-induced DC glycolysis, we determined that Wnt5a suppresses LPS-induced DC-mediated antigen-specific T cell proliferation in a manner similar to 2-deoxyglucose (2-DG) (FIG. 3A). Notably, this effect was observed in the absence of any alterations in DC surface maturation markers (FIG. 4). We have previously shown that Wnt5a promotes DC-mediated Treg cell differentiation both in vitro and in vivo (Holtzhausen et al., 2015). Altogether, these data indicate that inhibition of DC glycolysis and inhibition of DC OXPHOS would have reciprocal effects on Treg cell development. Indeed, co-culturing 2-DG-treated or Wnt5a-treated DCs with naive CD4+ T cells generated enhanced Treg cell differentiation in vitro, while inhibition of DC OXPHOS with oligomycin (oligo) eliminated these Treg cell populations (FIG. 3B). Together, these findings imply that Wnt5a drives Treg cell differentiation in the melanoma microenvironment by promoting DC OXPHOS. This is consistent with previous data showing that Wnt3a neither regulates DC metabolism nor promotes DC-mediated Treg cell generation (FIG. 1D-1E) (Holtzhausen et al., 2015). To examine this question more directly, we purified tumor-infiltrating DCs from BrafV600E-Pte−/−-NTC and BrafV600E-Pten−/−-Wnt5a-silenced tumors and delivered them by intradermal footpad injection into syngeneic FoxP3-mRFP transgenic reporter mice, followed by ipsilateral popliteal and inguinal lymph node isolation and Treg cell quantitation by flow cytometry. This confirmed that the BrafV600E-Pten−/−-Wnt5a-silenced tumor-derived DC population previously shown to exhibit diminished OXPHOS (FIG. 1G-1H) also exhibits suppressed Treg cell differentation in vivo (FIG. 3C). In summary, metabolic reprogramming plays a central role in Wnt5a regulation of DC functionality and determines whether a DC drives effector T cell expansion versus Treg cell differentiation (FIG. 3D).

Wnt5a Induction of DC Fatty Acid Oxidation Promotes Treg Cell Development and Suppresses Effector T Cell Activation Cancer-associated DCs exhibit higher cytoplasmic lipid content via increased lipid uptake, and these elevated lipid stores impair DC antigen processing and presentation (Herber et al., 2010). However, the mechanisms underlying these DC alterations in the tumor microenvironment are unknown. Since our data indicate that melanoma-derived Wnt5a altered DC function, we investigated the impact of Wnt5a and 3-catenin on DC lipid content and found this pathway to enhance DC fatty acid uptake and lipid stores (FIG. 5A-5B).

Figure 5F:
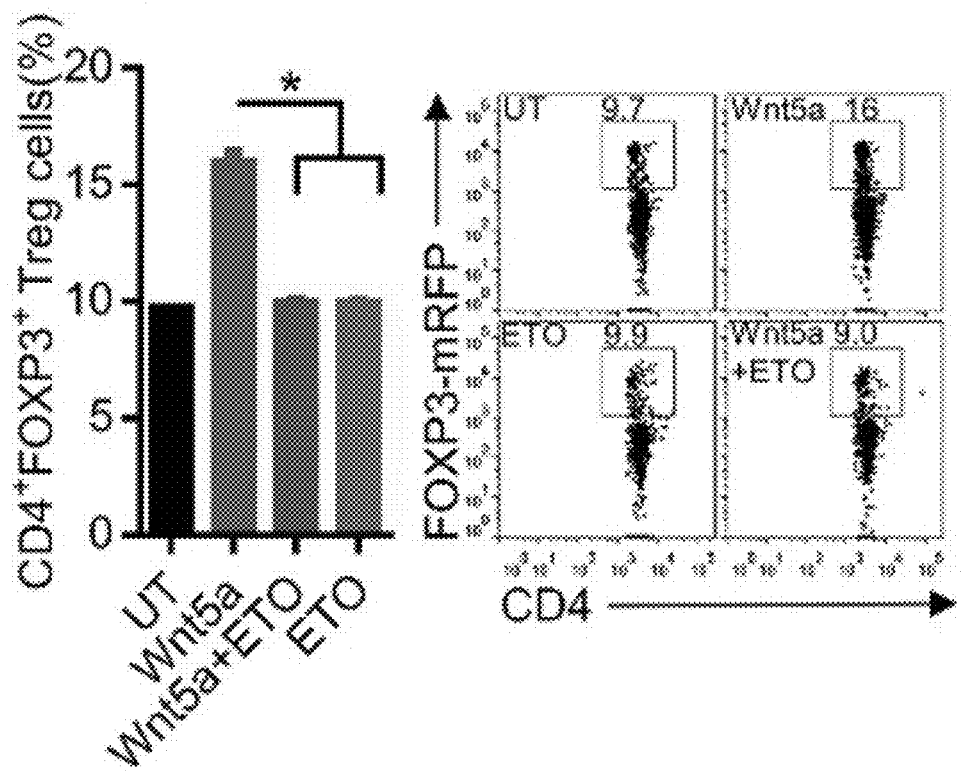
FIG. 5F shows a bar graph of the percent of DC-induced $CD4^+FoxP3^+$ Treg cells measured by in vivo Treg cell assay after DCs were treated with Wnt5a, ETO, or both reagents. n=4/group. The right panel shows representative FoxP3-RFPxCD4-FITC flow cytometry plots based on three independent experiments.
Figure 5G:
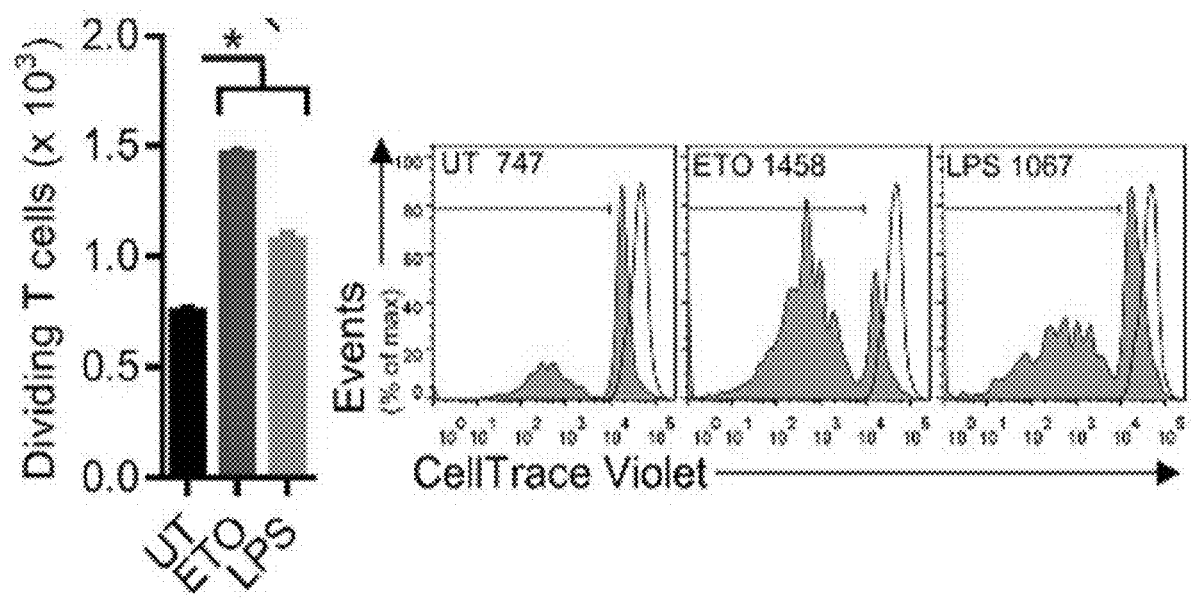
FIG. 5G shows a bar graph of the number of dividing $CD^{3+}CD^{8+}$ T cells as measured by CTV dilution. BMDCs were pulsed with OVA257-264 peptide, treated with ETO or stimulated with LPS, and co-incubated with OT-I splenocytes. n=3. The right panel shows representative flow cytometry CTV dilution assay profiles based on three independent experiments, gated on $CD^{3+}CD^{8+}$ T cells.
Figure 5H:
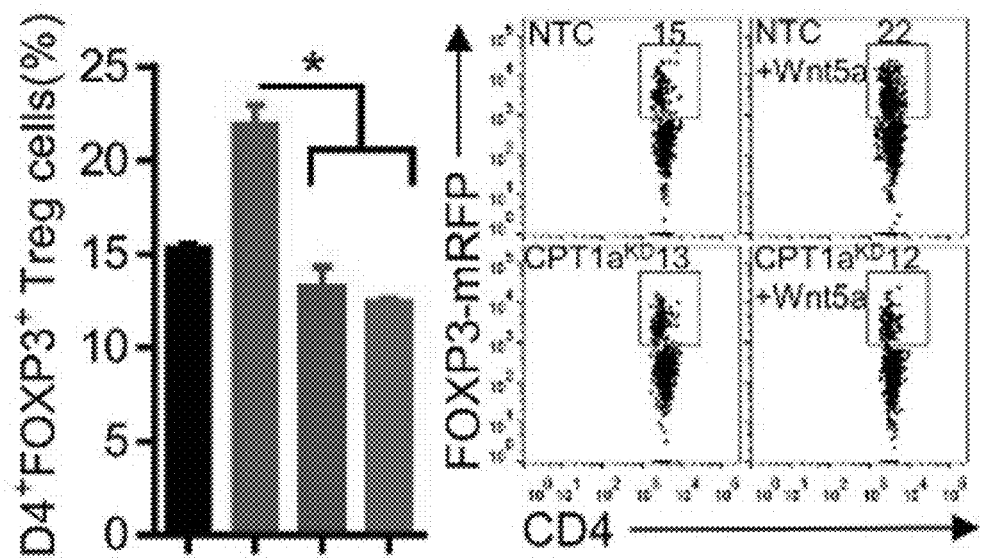
FIG. 5H shows a bar graph of the percent of $CD4^+FoxP3^+$ Treg cells measured after DC2.4-NTC or DC2.4-CPT1A$^{KD}$ DC lines were treated with rWnt5a and injected into footpads of Foxp3-mRFP mice. Inguinal lymph nodes were isolated and analyzed by flow cytometry. n=3/group. The right panel shows representative flow cytometry plots based on three independent experiments.
Figure 5I:
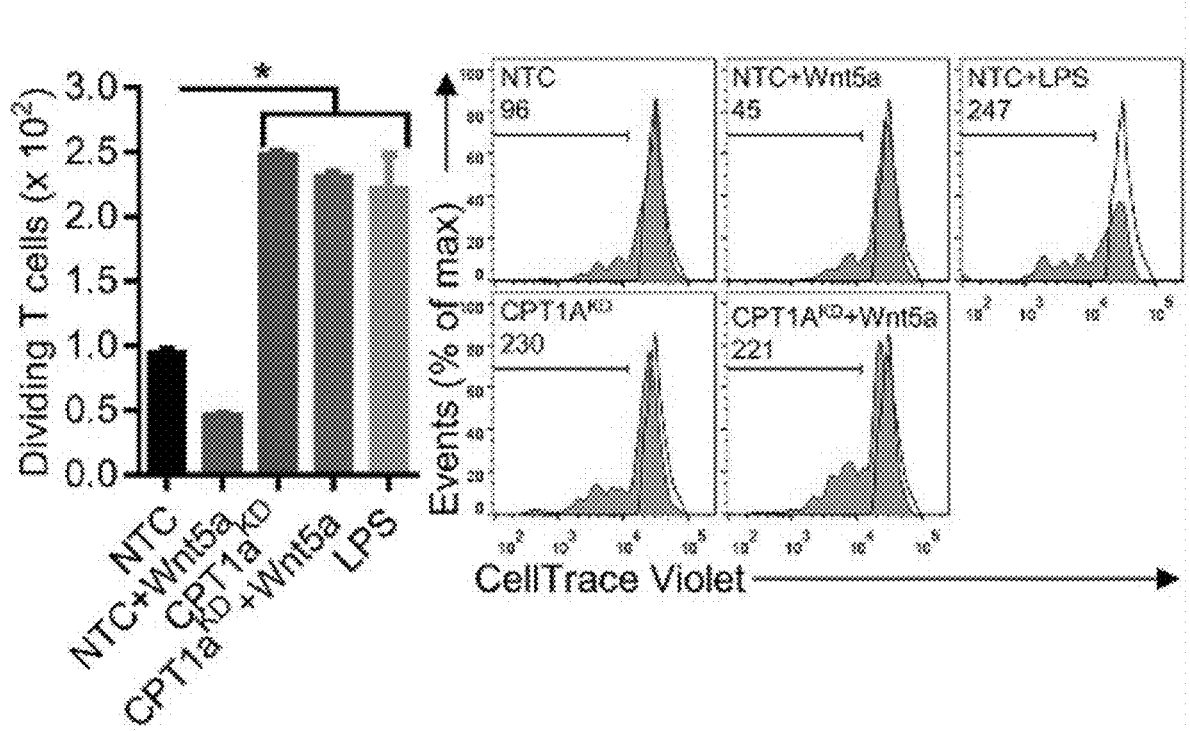
FIG. 5I shows a bar graph of the number of dividing $CD8^+$ T cells as measured by CTV dilution. DC2.4-NTC or DC2.4-CPT1AKD DC lines were loaded with OVA257-264 peptide, treated with rWnt5a or stimulated with LPS, and co-incubated with OT-I splenocytes. n=3. The right panel shows representative flow cytometry CTV dilution assay plots based on three independent experiments.
Figure 5J:
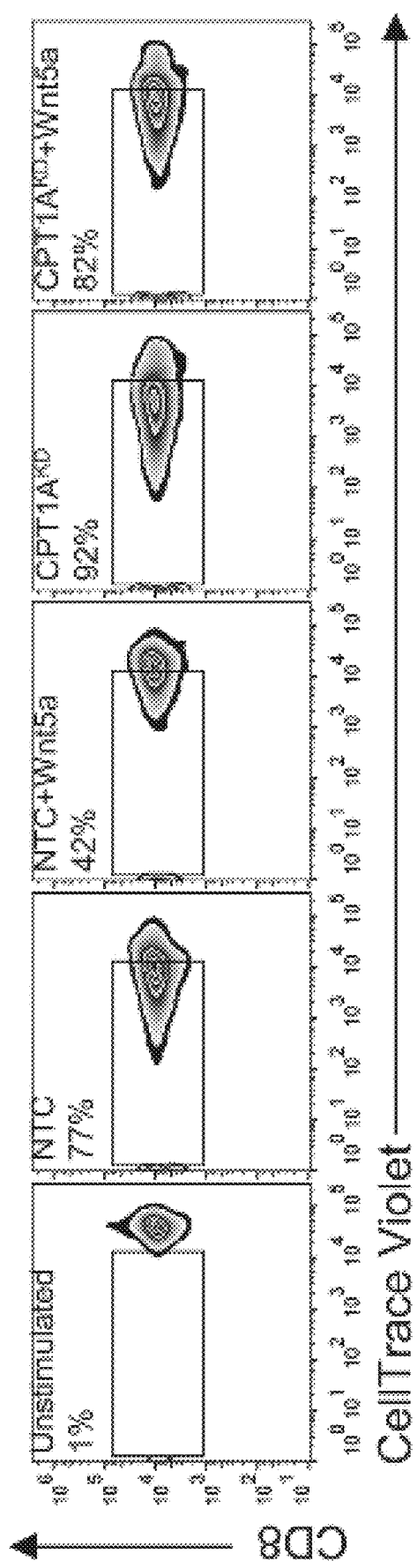
FIG. 5J shows representative flow cytometry CTV dilution assay plots based on three independent experiments in which BMDCs were transduced with a CPT1A-targeted shRNA-expressing or non-targeting control (NTC) lentivirus, treated with or without rWnt5a, pulsed with OVA257-264 peptide, and co-incubated with OT-I splenocytes. All data are mean±SEM. *P<0.05.
Figure 6E:
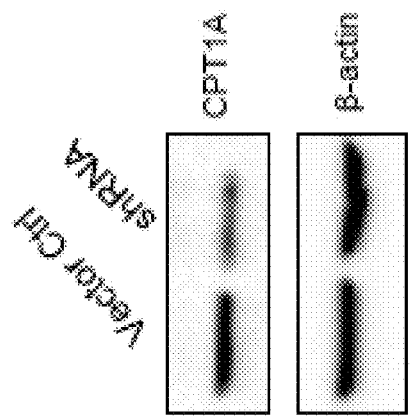
FIG. 6E shows a western blot probing for CPT1A following transduction of BMDCs with a CPT1A-targeted shRNA-expressing lentivirus.
Figure 7D:
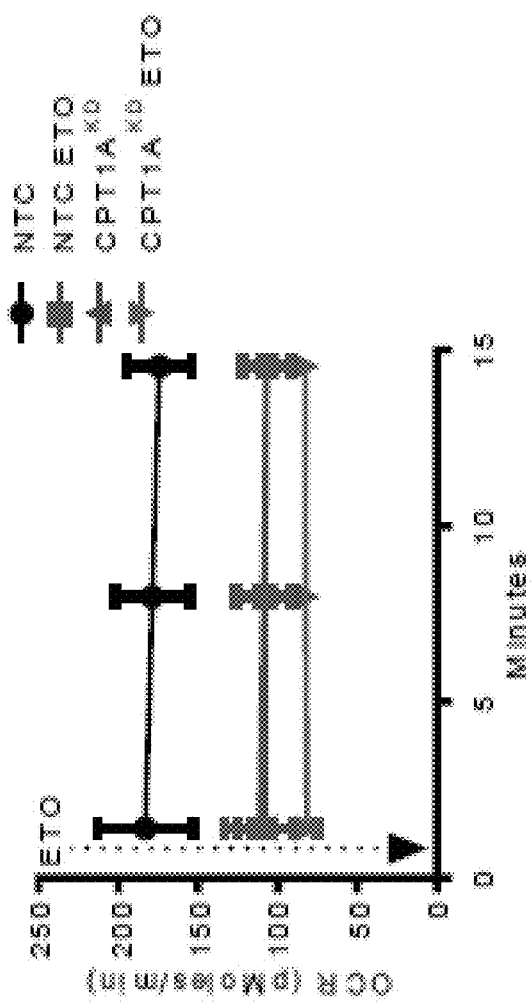
FIG. 7D shows a scatterplot of the OCR measured in DC2.4-NTC and DC2.4-CPT1A$^{KD}$ cell lines in the presence and absence of ETO over a period of 15 minutes.
Figure 7E:
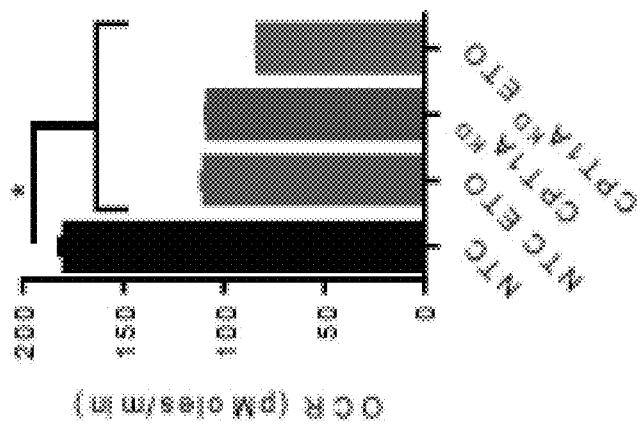
FIG. 7E shows a bar graph of the mean (±SEM) OCR for each set of data collected in FIG. 7D. *P<0.05.

We, therefore, reasoned that Wnt5a may enhance OXPHOS in DCs by promoting fatty acid oxidation (FAO). To determine whether Wnt5a regulated FAO in DCs, we analyzed the real-time OCR of DCs treated with rWnt5a in the presence and absence of the carnitine palmitoyl transferase-1 (CPT1) mitochondrial fatty acid transporter inhibitor, etomoxir (ETO). These experiments showed that ETO completely ablated Wnt5a induction of both murine and human DC mitochondrial respiration while not impacting DC viability (FIGS. 5C-5D and FIGS. 6A-6B). Since our prior data suggested that OXPHOS in DCs played an important role in DC-mediated Treg cell generation and studies indicated that DC glutaminolysis was not involved in this process (FIG. 6C), we investigated the role of FAO in DC-dependent Treg cell generation. This demonstrated that ETO treatment potently suppresses the ability of Wnt5a-conditioned DCs to drive Treg cell differentiation in vitro and in vivo following the adoptive transfer of conditioned DCs into FoxP3-mRFP reporter mice (FIGS. 5E-5F). In line with our previous data indicating that inhibition of OXPHOS in DCs promotes antigen-specific T cell proliferation, we found ETO treatment potently induced DC-mediated T cell activation despite a downregulation in DC co-stimulatory receptors based on flow cytometry (FIG. 5G and FIG. 4). To confirm that off-target effects of ETO did not contribute to this process, we genetically silenced Cpt1a expression in the DC2.4 myeloid DC line and determined the ability of the resulting DC2.4-CPT1A-silenced cell line to induce Treg cell differentiation in vivo and to promote effector T cell proliferation in vitro relative to the DC2.4-NTC control cell line (FIGS. 7A-7E). This revealed that genetically targeting CPT1A in the DC2.4 line effectively made these DCs resistant to Wnt5a-induced Treg cell development while promoting their ability to stimulate CD8+ T cell proliferation (FIGS. 5H-5I). To demonstrate that genetic silencing of CPT1A can have similar effects in primary DCs, we engineered a CPT1A-specific shRNA-expressing lentiviral vector and transduced BMDCs before performing OT-I CD8+ T cell proliferation assays (FIG. 6D-6E). These experiments indeed demonstrated that primary CPT1A-silenced DCs induce potent CD8+ T cell proliferation while maintaining resistance to Wnt5a-induced tolerization (FIG. 5J).

Overall, these data provide a potential mechanistic explanation for the increased lipid stores previously observed in cancer-associated DCs. In addition, this work implies that Wnt5a shifts DCs from glycolysis towards FAO in the melanoma microenvironment, and this metabolic program effectively inhibits effector T cell activation while driving Treg cell differentiation.

Figure 8A:
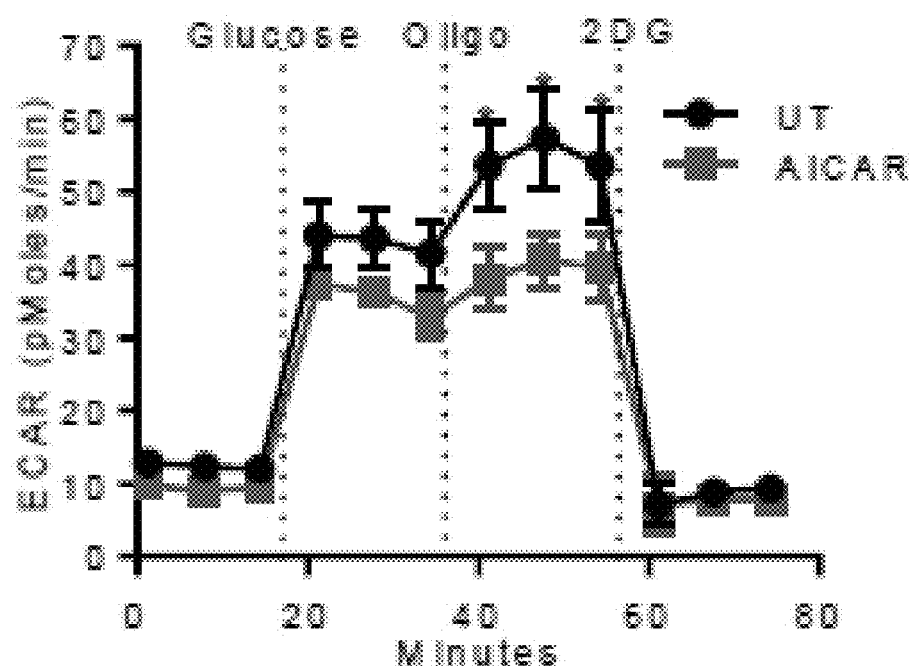
FIG. 8A shows a scatterplot of the measured ECAR of untreated (UT) DCs and DCs pre-treated with the AMP analog and AMPK agonist AICAR for 24 hrs.
Figure 8B:
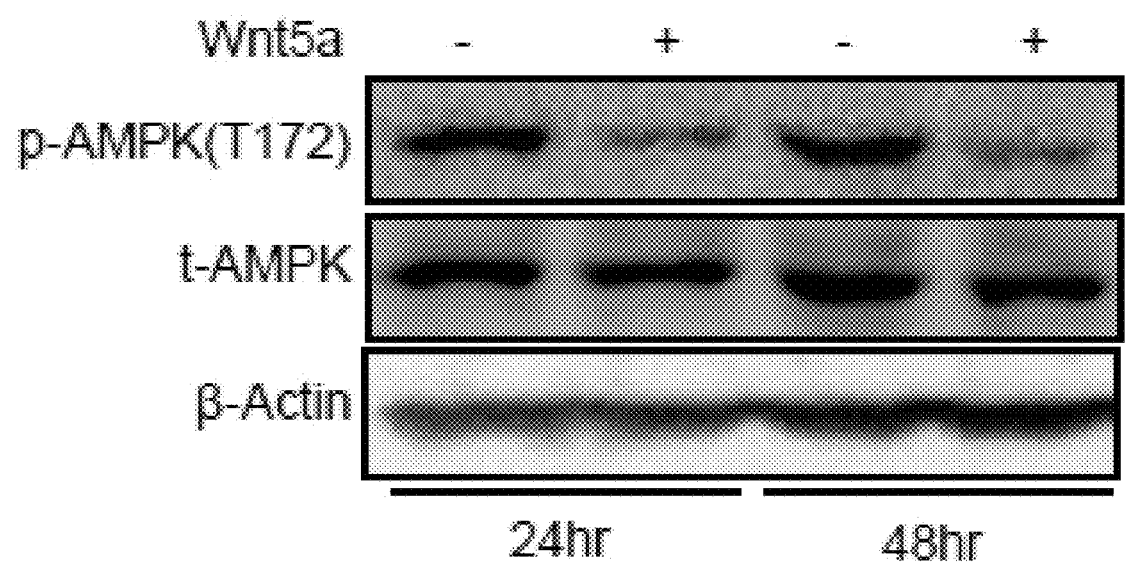
FIG. 8B shows a western blot probing for p-AMPK(T172) and t-AMPK in DCs 24 hrs and 48 hrs after Wnt5a (200 ng/mL) stimulation. Data is representative of 3 independent experiments.
Figure 8E:
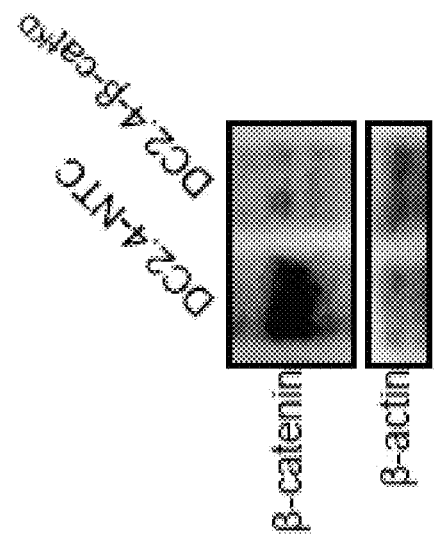
FIG. 8E shows a western blot probing for Ctnnb1 (β-catenin) in DC2.4-NTC control and DC2.4-β-catenin$^{KD}$ (DC2.4-β-cat$^{KD}$) cell lines.
Figure 8D:
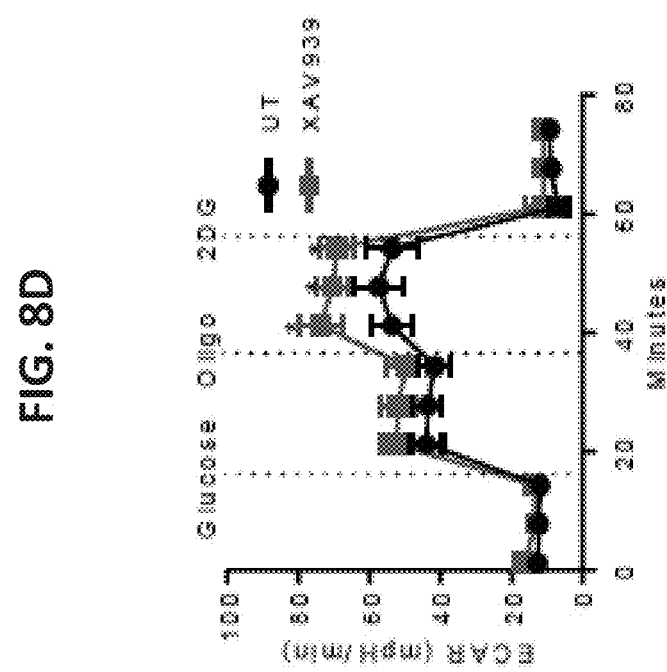
FIG. 8D shows a scatterplot of the ECAR measured in DCs treated with the selective Wnt/p-catenin inhibitor XAV939.
Figure 8C:
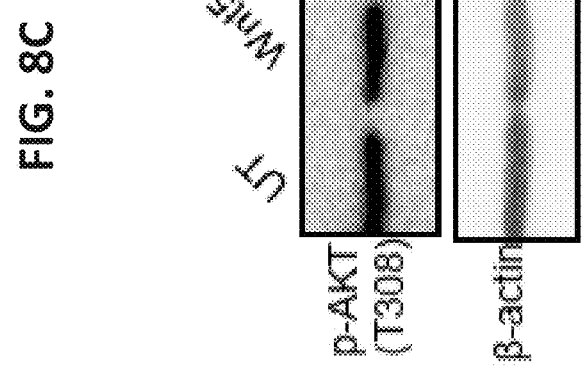
FIG. 8C shows a western blot probing for p-AKT (T308) in BMDCs 48 hrs after Wnt5a (200 ng/mL) stimulation. Data is representative of 3 independent experiments.

The Wnt5a-β-Catenin Signaling Pathway Regulates DC Fatty Acid Oxidation Via the PPAR-γ-CPT1A Axis Previous investigators have proposed that activation of AMP-activated protein kinase (AMPK) by the AMP analog, AICAR, would antagonize the glycolytic surge required for DC maturation (Krawczyk et al., 2010). Our findings are consistent with this work (FIG. 8A). As a result, we hypothesized that Wnt5a shifts DC metabolism from glycolysis to FAO by activating AMPK. However, we found Wnt5a suppressed AMPK activation based on Thr-172 phospho-AMPK immunoblot analysis (FIG. 8B). In addition, we detected no impact of Wnt5a on DC Akt Thr-308 phosphorylation, a well-characterized promoter of glycolysis in DCs (FIG. 8C) (Krawczyk et al., 2010). These results suggest that the Wnt5a-mediated metabolic shift from glycolysis to FAO is independent of AMPK and Akt signaling.

Figure 9A:
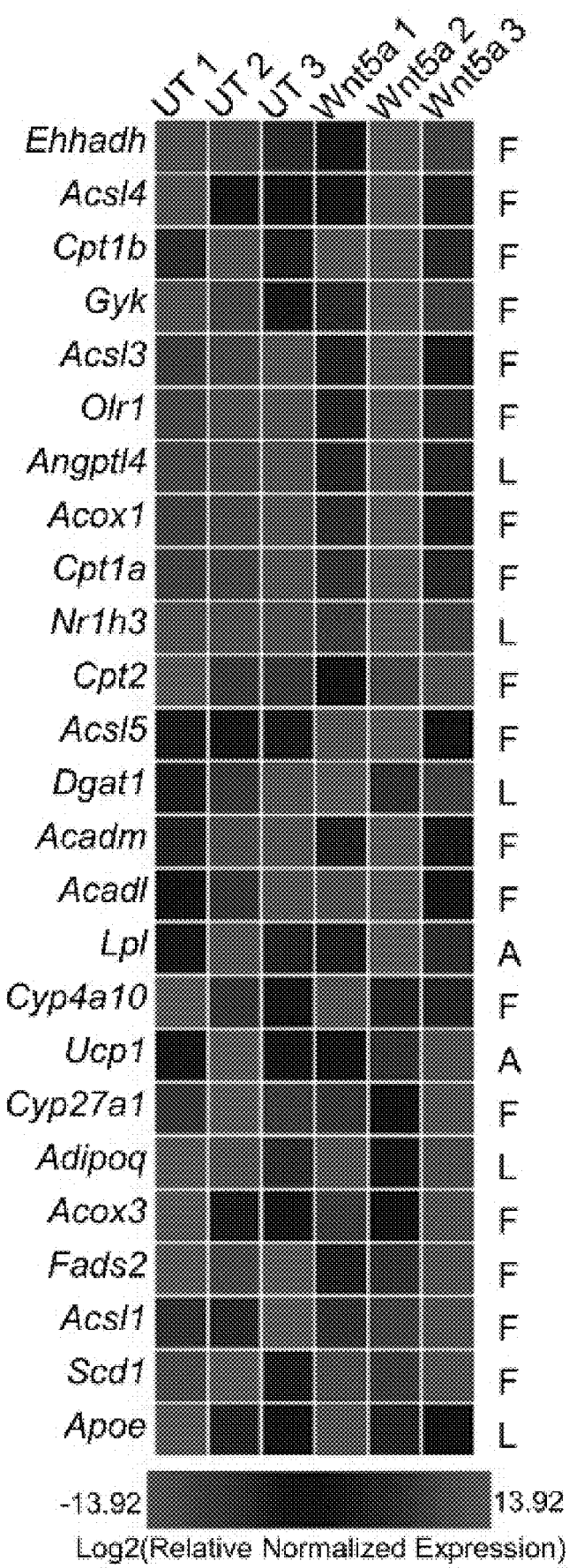
FIG. 9A shows a heatmap of gene expression based on PCR analysis of BMDCs treated with rWnt5a for 48 hr. "F" marks fatty acid metabolism genes, "L" marks lipid transport genes, and "A" marks adipogenesis genes. Red indicates high expression, and blue indicates low expression. n=3.
Figure 10A:
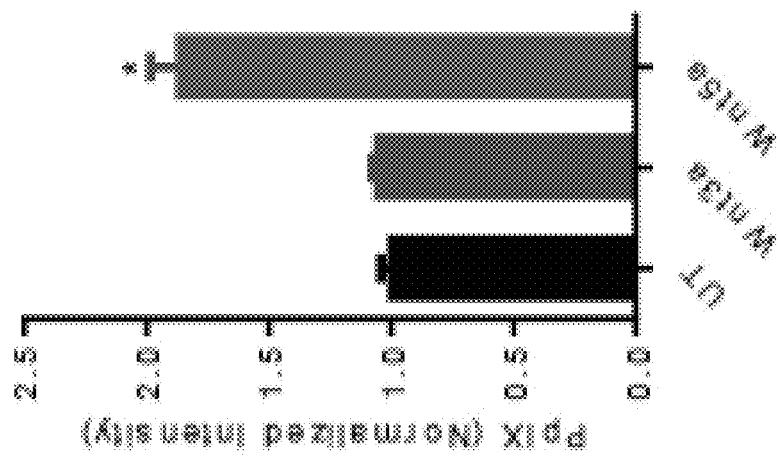
FIG. 10A shows bar graphs of Pparγ (left) and Cp11a (right) mRNA levels in untreated (UT) and Wnt3a-stimulated DCs based on qRT-PCR analysis.

The peroxisome proliferator-activated receptor (PPAR) family of transcription factors regulate the expression of several key factors involved in FAO. Treatment of primary DCs with the β-catenin inhibitor, XAV939, and genetic silencing of β-catenin in the DC2.4 cell line (DC2.4-β-catenin-silenced) promoted glycolysis in DCs, confirming that β-catenin regulates DC metabolism (FIG. 8D-8G). β-catenin induction of PPAR-γ expression has been previously described (Jansson et al., 2005). Consistent with these data, we found rWnt5a stimulation of primary DCs induced expression of several genes downstream of the PPAR-γ transcription factor previously identified to promote FAO, including CPT1A, using a quantitative polymerase chain reaction (qPCR) array (FIG. 9A). We subsequently verified that rWnt5a induces upregulation of Pparg and Cpt1a using real-time qPCR and immunoblot analysis in both murine and human DCs (FIGS. 9B-9D and FIG. 8H). To confirm that β-catenin regulates CPT1A expression, we found reduced expression of CPT1A in the DC2.4-β-catenin-silenced cell line, while β-catenin activation of primary DCs via inhibition of the GSK3β enzyme promoted both PPAR-γ and CPT1A expression (FIGS. 9E-9F and FIGS. 8E-8F). Consistent with its inability to alter DC metabolism, Wnt3a also failed to induce expression of both PPAR-γ and CPT1A in DCs (FIG. 10A).

PPAR-γ is a transcriptional co-activator complexing with β-catenin to induce genes that drive FAO (Jansson et al., 2005). We therefore performed endogenous co-immunoprecipitation experiments in primary DCs and found PPAR-γ to bind to β-catenin upon Wnt5a stimulation (FIG. 9G and FIG. 8I). All together, these findings support a mechanism by which Wnt5a signaling promotes PPAR-γ-dependent induction of CPT1A to activate FAO in DCs.

Figure 9I:
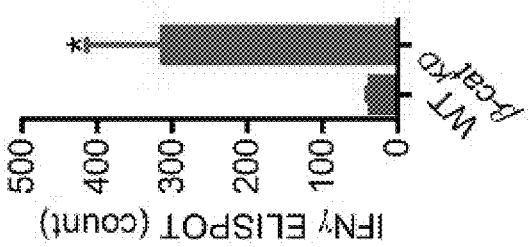
FIG. 9B shows a bar graph of Pparg1 mRNA levels in BMDCs treated with rWnt5a based on qRT-PCR analysis. n=3.
FIG. 9C shows a bar graph of Cpt1a mRNA levels in BMDCs treated with rWnt5a based on qRT-PCR analysis.
FIG. 9D shows a western blot probing for PPARγ and CPT1A in human monocyte-derived DCs treated with rWnt5a. n=3.
FIG. 9E shows a bar graph of Cpt1a mRNA levels in DC2.4-NTC and DC2.4-β-cat$^{KD}$ cell lines based on qRT-PCR analysis. n=3.
FIG. 9F shows bar graphs of Pparg1 (left) and Cpt1a (right) mRNA levels in BMDCs treated with either the GSK3β inhibitor BIO or its control, MeBIO, based on qRT-PCR analysis. n=3.
FIG. 9G shows a western blot probing for PPARγ following β-catenin immunoprecipitation from Wnt5a-treated BMDCs. n=3.
FIG. 9J shows a scatterplot of tumor volume over time, representing primary Braf$^{V600E}$-Pten$^{-/-}$ melanoma progression in WT and β-cat$^{ΔDC}$ hosts. n=6/group.
FIG. 9K shows a photograph of an ELISPOT plate (left) and a bar graph (right) depicting IFN-γ ELISPOT analysis of tumor-infiltrating, TRP2-specific T cells derived from Braf$^{V600E}$-Pten$^{-/-}$ melanomas resected from either WT or β-cat$^{ΔDC}$ mice. n=3/group. Data is representative of two independent experiments. All data are mean±SEM. *P<0.05.
Figure 9H:
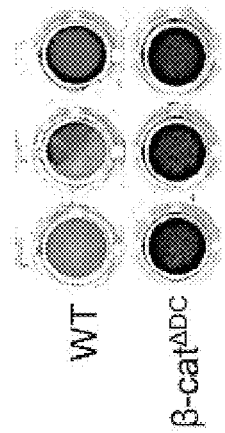
Figure 9K:
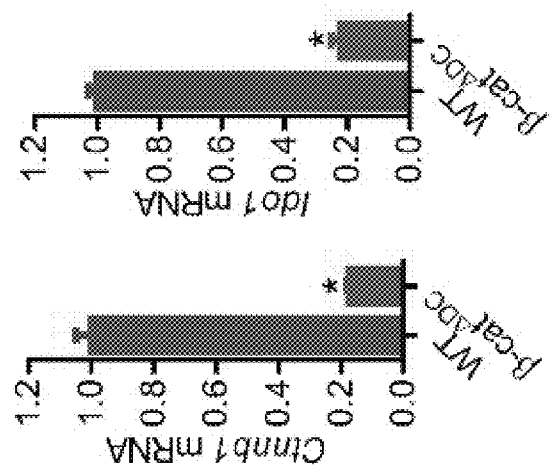
Figure 9J:
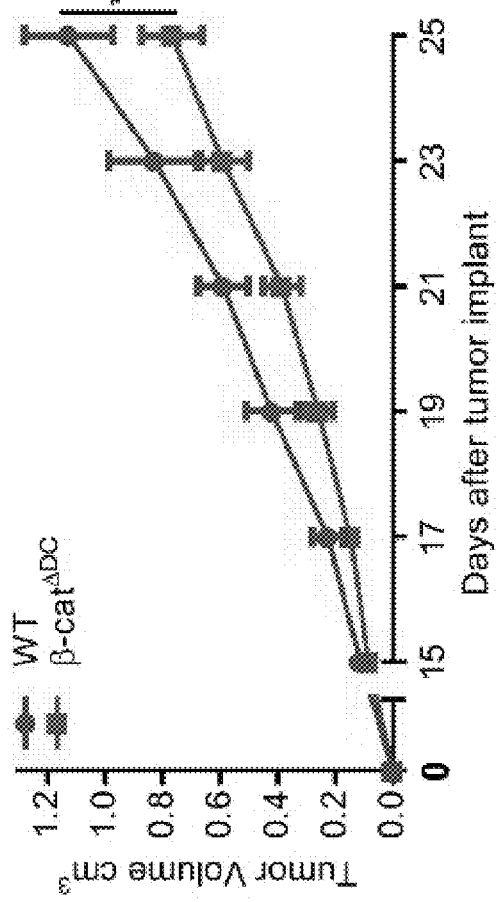

Based on these findings, we directly investigated the impact of this DC signaling pathway on the generation of anti-tumor immunity in vivo. After implanting the BrafV600E-Pten−/− melanoma cell line into syngeneic wild-type mice or mice with β-catenin-deleted DCs (β-catΔDC; FIG. 9H-9I), we monitored primary tumor growth and demonstrated BrafV600E-Pten−/− melanoma growth restriction in β-catΔDC hosts in association with a significant enhancement in melanoma tyrosinase-related protein 2 (TRP2) antigen-specific T cell responses based on interferon (IFN)-γ ELISPOT (FIG. 9J-9K). Altogether, these findings suggest that the DC β-catenin-PPAR-γ signaling pathway suppresses the development of T cell-mediated immunity in melanoma.

Wnt5a-Induced Fatty Acid Oxidation Regulates the Enzymatic Activity of DC Indoleamine 2,3-Dioxygenase IDO plays a critical role in driving Treg cell development in the tumor microenvironment (Hanks et al., 2013, Holtzhausen et al., 2015, Munn et al., 2004). Despite inducing DC IDO expression, Wnt3a stimulation, we noted, failed to condition DCs to promote Treg cell differentiation. In light of the potent impact of FAO on DC-mediated Treg cell generation, we hypothesized that Wnt5a-mediated regulation of FAO was directly modulating the enzymatic activity of IDO. In order to test this hypothesis, we measured production of the IDO byproduct kynurenine in purified DC cultures using high-performance liquid chromatography (HPLC). These studies confirmed that rWnt5a promoted DC IDO enzymatic activity and that inhibition of FAO in DCs completely eliminated this effect, suggesting that FAO in DCs regulated the enzymatic activity of IDO (FIG. 11A). To demonstrate that this occurs within the melanoma microenvironment, we purified tumor-infiltrating DCs from resected BrafV600E-Pten−/−-NTC and BrafV600E-Pten−/−-Wnt5a-silenced tumors and analyzed kynurenine generation as a surrogate for IDO enzymatic activity. This demonstrated that tumor-infiltrating DCs derived from melanomas lacking Wnt5a expression exhibit lower IDO enzyme activity similar to ETO-treated tumor-infiltrating DCs purified from BrafV600E-Pten-/--NTC control tumors (FIG. 11B). These findings show that Wnt5a-induced FAO plays a critical role in regulating DC IDO enzyme activity within developing melanomas.

Figure 10B:
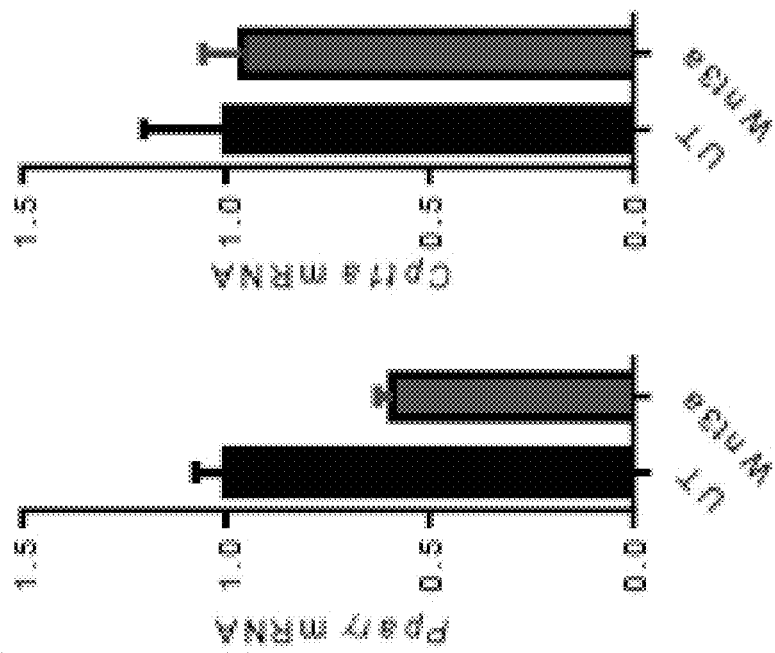
FIG. 10B shows a bar graph of PpIX levels in Wnt3a- and Wnt5a-stimulated DCs based on flow cytometry analysis. Cells were treated with either Wnt5a or Wnt3a for 48 hours followed by a 4-hour incubation with 1 mM δ-ALA before being subjected to flow cytometry analysis of intracellular PpIX.

Since the IDO apoenzyme requires the heme-derived PpIX prosthetic group for full enzymatic activity and the tricarboxylic acid (TCA) cycle intermediate, succinyl CoA, serves as the primary substrate for heme synthesis, we conjectured that increased PpIX concentrations may partially explain why FAO in DCs drives IDO function. Thus, we studied the impact of rWnt5a on DC concentrations of PpIX and hemin, the heme breakdown product, using a modified flow cytometry technique and a colorimetric assay, respectively (Hryhorenko et al., 1998). Indeed, this demonstrated that rWnt5a enhanced DC concentrations of the PpIX prosthetic group and its downstream degradation product, hemin, in a FAO-dependent manner (FIG. 11C-11D). Notably, consistent with its inability to modulate DC metabolism, Wnt3a also failed to enhance PpIX synthesis in DCs (FIG. 10B).

Figure 10C:
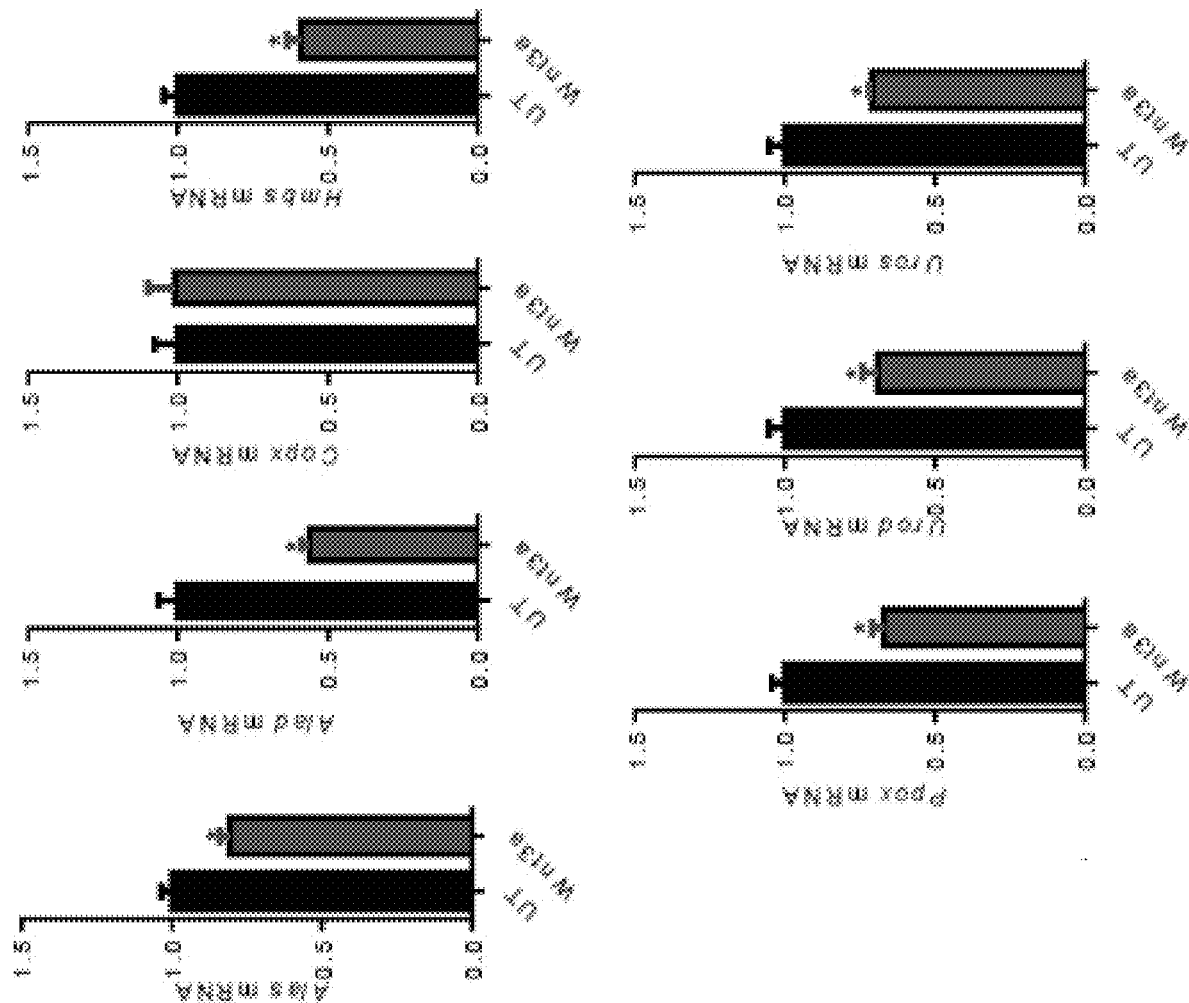
FIG. 10C shows a bar graph of the levels of heme synthesis enzymes in Wnt3a-stimulated DCs based on qRT-PCR analysis. All data is mean±SEM. n=3. *P<0.05.
Figure 11F:
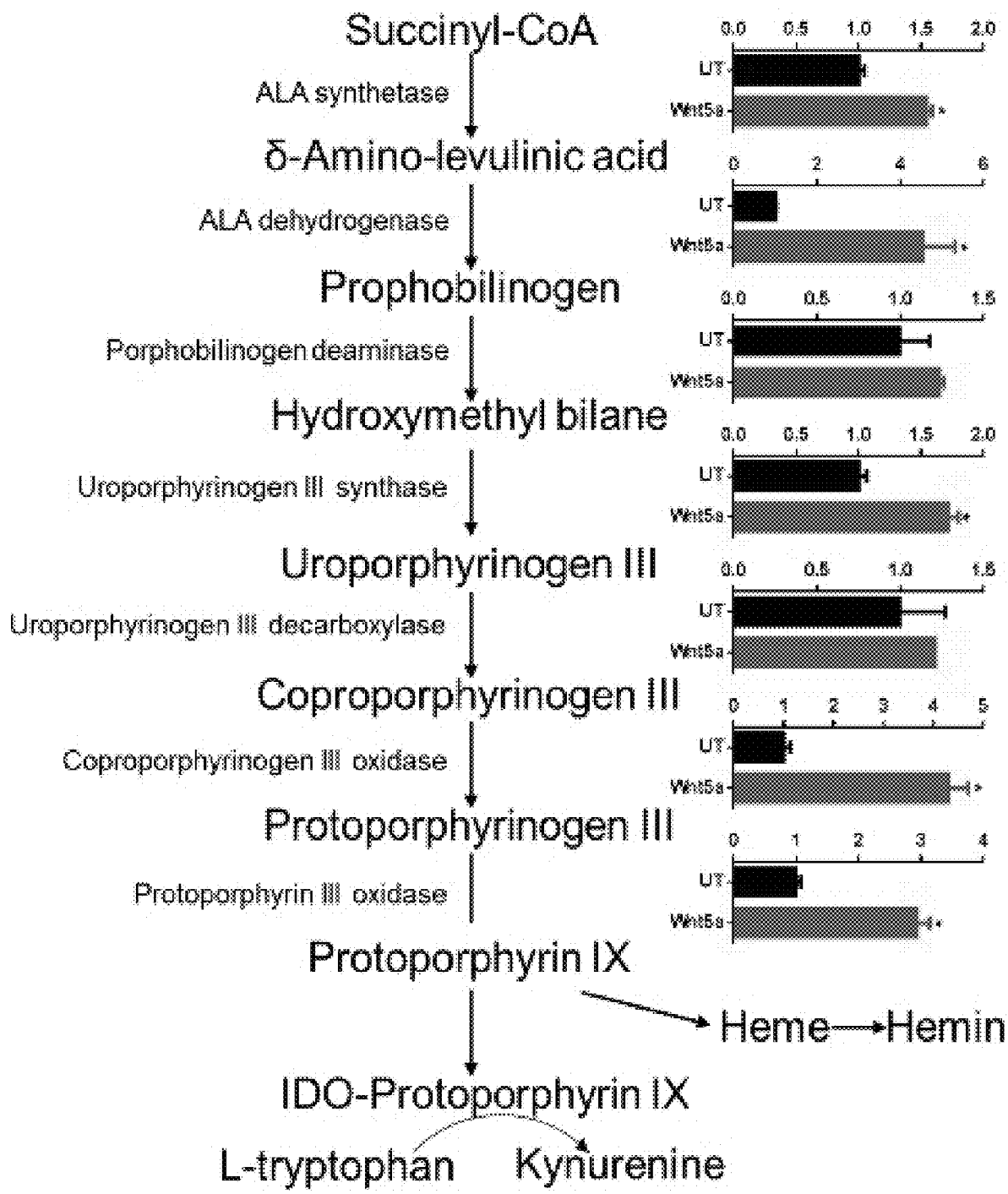
FIG. 11F shows bar graphs of the levels of heme biosynthetic enzymes in DCs treated with rWnt5a based on qRT-PCR analysis. n=3.

Additional studies have determined that the PPAR-γ co-activator-1α-dependent and rate-limiting enzyme of heme biosynthesis, aminolevulinic acid synthase-1 (ALAS1), is upregulated in Wnt5a-stimulated DCs (FIG. 11E) (Handschin et al., 2005). Indeed, further analysis showed rWnt5a, but not rWnt3a, upregulated expression of Alas1 and several additional enzymes involved in PpIX synthesis, including ALA dehydratase (ALAD), uroporphyrinogen III synthetase, coprophyrinogen III oxidase, and protoporphyrin III oxidase (FIG. 11F and FIG. 10C).

Figure 11G:
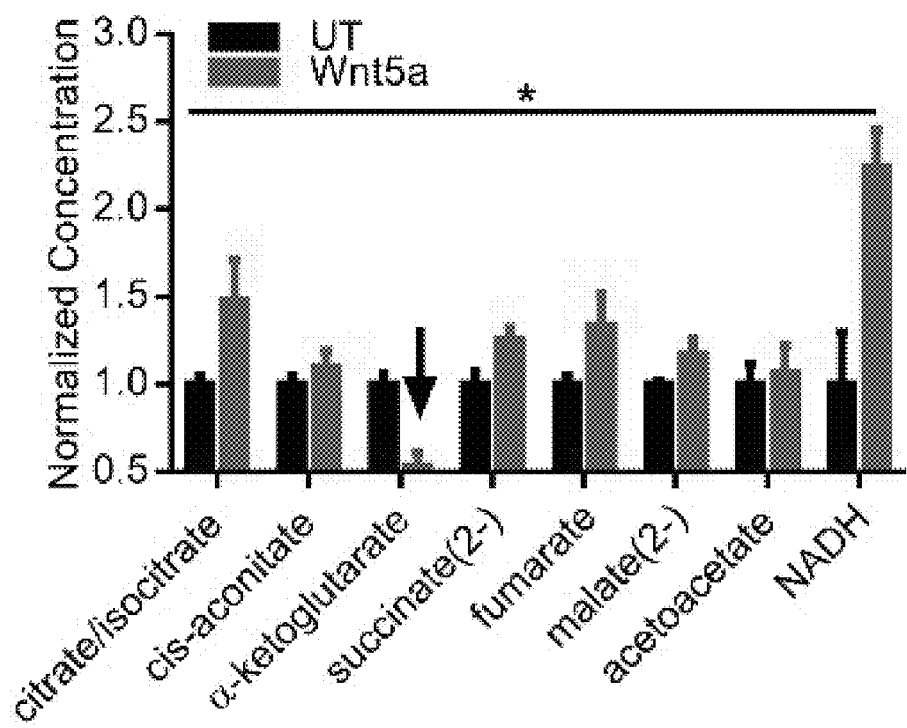
FIG. 11G shows a bar graph of the normalized concentrations of TCA metabolic intermediates derived from DCs treated with rWnt5a based on LC-MS analysis. The arrow highlights downregulation of α-ketoglutarate.
Figure 11H:
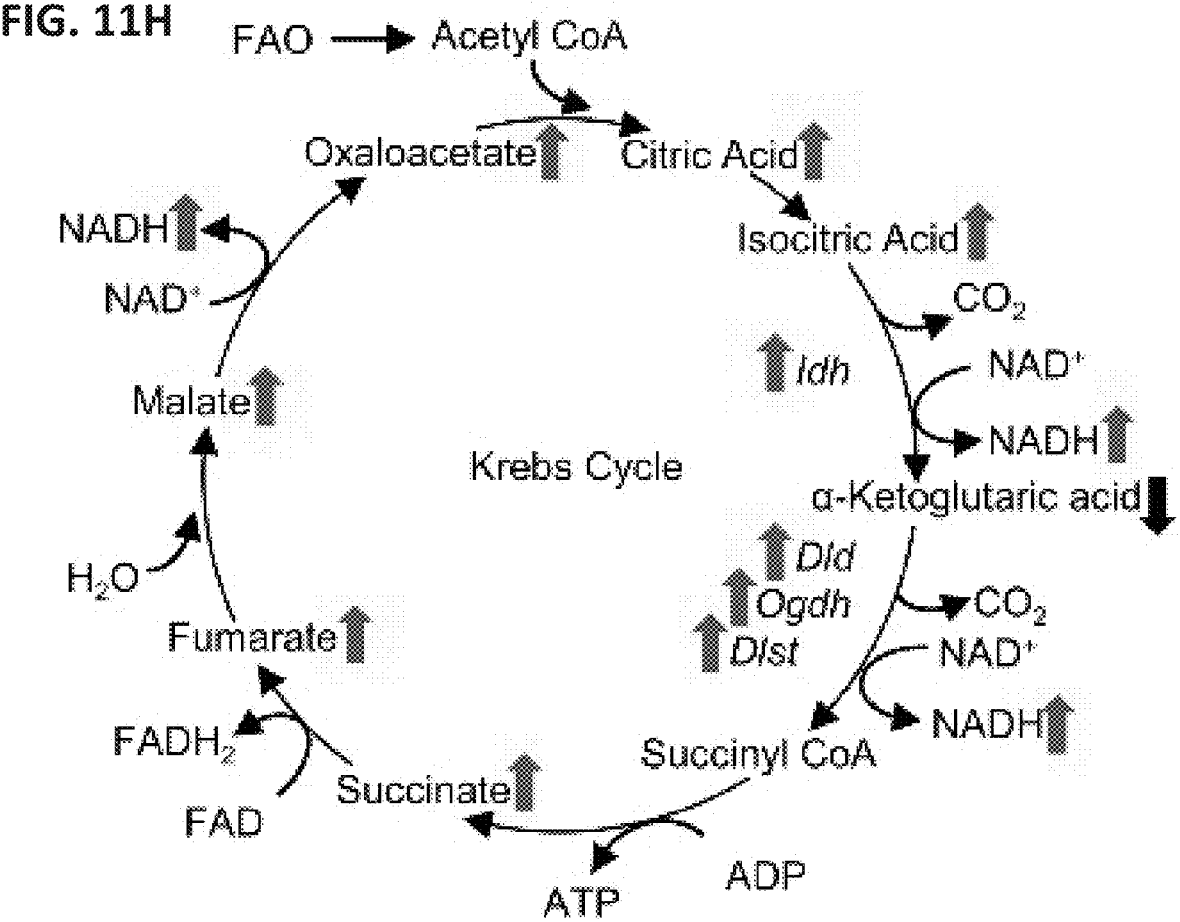
FIG. 11H shows a schematic of the TCA cycle, highlighting intermediates (red arrows) and enzymes (blue arrows). Changes in response to Wnt5a are indicated.
Figure 11I:
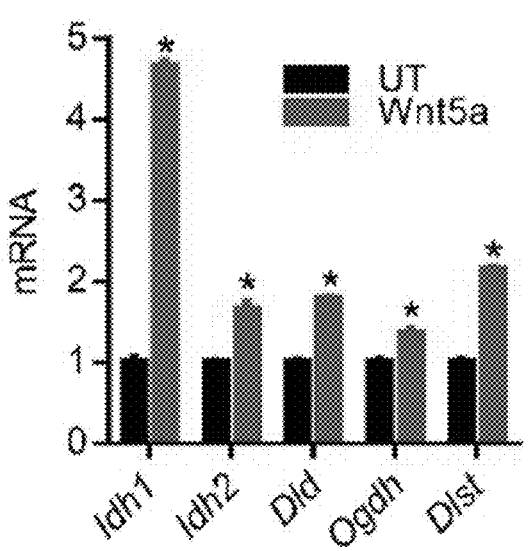
FIG. 11I shows a bar graph of levels of select TCA cycle enzymes in DCs based on qRT-PCR analysis. n=3. The enzymes include: isocitrate dehydrogenases (Idh), an oxoglutarate dyhydrogenase complex: dihydrolipoyl dehydrogenase (Dld), dihydrolipoyl succinyltransferase (Dlst), and oxoglutarate decarboxylase (Oghd).
Figure 11J:
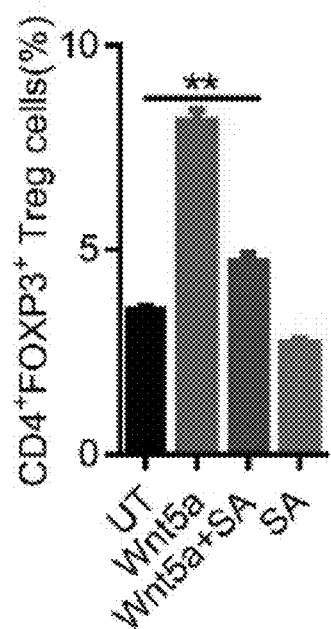
FIG. 11J shows a bar graph of the percent of DC-induced CD4$^+$FoxP3$^+$ Treg cells measured by in vitro Treg cell assay following treatment with rWnt5a, succinylacetone (SA), or both reagents. n=3. All data are mean±SEM. *P<0.05.

These data indicate that Wnt5a promotes DC IDO enzymatic activity by enhancing flux through the heme biosynthetic pathway and promoting the synthesis of the PpIX prosthetic group. To elucidate how Wnt5a induction of FAO in DCs results in the increased concentrations of PpIX described above, we utilized high-resolution liquid chromatography-mass spectrometry to measure intermediate TCA metabolites in response to rWnt5a stimulation (Liu et al., 2014b). We observed increased quantities of many TCA intermediates but a decrease in α-ketoglutarate (FIG. 11G-11H). Further qRT-PCR studies showed rWnt5a stimulated the expression of isocitrate dehydrogenase (Idh1, Idh2) as well as all three components of the downstream α-ketoglutarate dehydrogenase complex (Oghd, Dld, Dlst), which converts α-ketoglutarate to succinyl CoA (FIG. 11H-11I). Altogether, these alterations suggest that Wnt5a promotes heme biosynthesis by affecting the TCA cycle, and this process contributes to increased quantities of PpIX in DCs (FIG. 11H). Finally, we found that inhibition of the enzyme ALAD with succinylacetone also significantly abrogated the ability of Wnt5a-stimulated DCs to promote Treg cell generation, demonstrating that modulation of the heme biosynthetic pathway ultimately impacts Treg cell differentiation (FIG. 11J).

This work describes a link between cellular metabolism and regulation of immune tolerance via modulation of DC IDO activity and further demonstrates that melanomas manipulate this pathway in a Wnt5a-dependent manner.

Wnt5a-β-Catenin-Induced Fatty Acid Oxidation is a Key Regulatory Pathway Underlying DC Tolerization We further demonstrated that FAO inhibition in DCs not only eliminated the impact of Wnt5a on DC-mediated Treg cell differentiation in vitro but also further suppressed Treg cell differentiation by DCs genetically ablated for IDO (FIG. 12A). These data support the existence of additional mechanisms of DC-mediated Treg cell differentiation beyond IDO that are downstream of the Wnt5a-β-catenin-FAO signaling pathway.

Figure 12E:
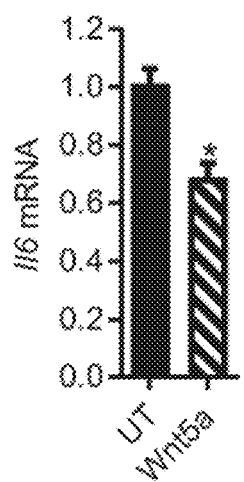
FIG. 12E shows bar graphs of Il6 (left) and Il12b (right) mRNA levels in BMDCs treated with rWnt5a based on qRT-PCR analysis.
Figure 12E:
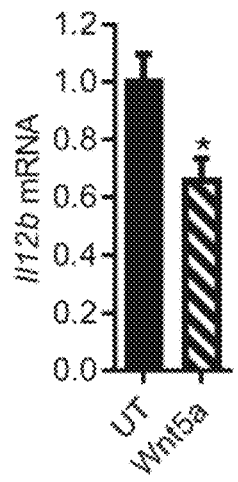
Figure 12F:
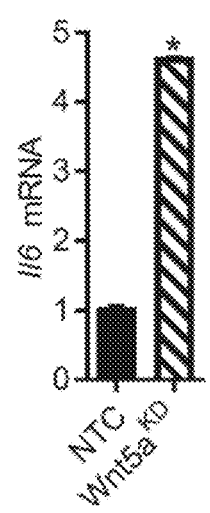
FIG. 12F shows bar graphs of in situ Il6 (left) and Il12b (right) mRNA levels in tumor-infiltrating DCs purified from Braf$^{V600E}$Pten$^{-/-}$-NTC or -Wnt5a$^{KD}$ melanomas based on qRT-PCR analysis. n=3/group.
Figure 12F:
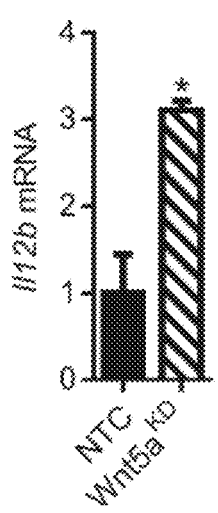
Figure 12G:
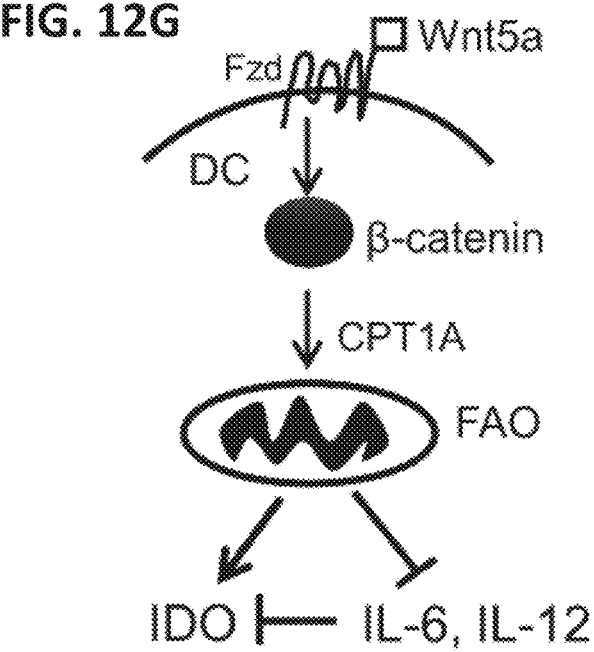
FIG. 12G shows a schematic of the proposed β-catenin-dependent pathway regulating IDO and pro-inflammatory cytokine expression via fatty acid oxidation (FAO) in DCs. All data are mean±SEM. *P<0.05.

Since the local cytokine milieu can influence naive CD4+ T cell differentiation into Treg cells, we examined the effect of FAO on the DC cytokine expression profile by comparing the expression of several cytokines between the DC2.4-CPT1A-silenced cell line and the DC2.4-NTC control cell line based on qRT-PCR and ELISA. These experiments demonstrated that genetically silencing Cpt1a to inhibit FAO results in significant elevations in expression of the pro-inflammatory cytokines, interleukin (IL)-6 and IL-12, while no significant differences in the expression of IL-10 or transforming growth factor β (TGF-β) were noted (FIG. 12B-12C; data not shown). These alterations in cytokine expression were further recapitulated in primary DC populations exposed to the CPT1A inhibitor, ETO (FIG. 12D). Additional studies confirmed Wnt5a suppresses IL-6 and IL-12 expression in primary DCs, implicating the Wnt5a-β-catenin signaling pathway in the regulation of these pro-inflammatory cytokines (FIG. 12E). To demonstrate that melanoma-derived Wnt5a induced a similar DC cytokine expression profile in situ, we purified tumor-infiltrating DCs from BrafV600E-Pten-/--NTC and BrafV600E-Pten-/--Wnt5a-silenced tumors as above and quantitated both Il6 and Il12b expression by qRT-PCR. These studies supported our previous findings in that BrafV600E-Pten-/- melanomas genetically silenced for Wnt5a were associated with significant elevations in tumor-infiltrating DC IL-6 and IL-12p40 expression (FIG. 12F). Together, DC FAO suppresses IL-6 and IL-12 expression, in addition to stimulating IDO enzymatic activity, creating an environment that favors Treg cell generation (FIG. 12G). Indeed, blocking IL-6 and IL-12 using antagonistic antibodies eliminated the additional suppressive effect of FAO inhibition on Treg cell generation, indicating that the Wnt5a-β-catenin-FAO pathway modulates both IDO and pro-inflammatory cytokine expression in DCs (FIG. 12A). Based on previous studies demonstrating that IL-6 promotes the proteosomal degradation of IDO, these data suggest that FAO in DCs may also promote IDO stabilization (Orabona et al., 2008). These dual mechanisms of IDO regulation suggest a central role for the Wnt5a-β-catenin signaling pathway in DC tolerization.

Figure 13A:
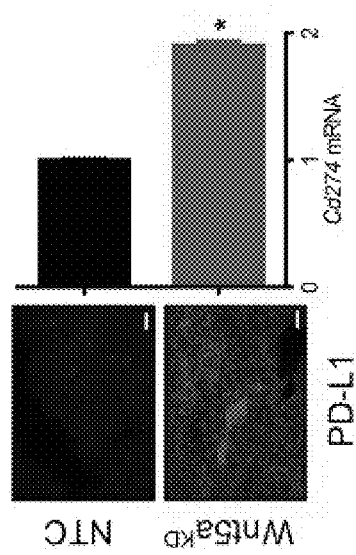
FIG. 13A shows a bar graph of IFN-γ ELISPOT analysis of tumor-infiltrating T cells derived from Braf$^{V600E}$Pten$^{-/-}$-NTC or -Wnt5a$^{KD}$ melanomas. n=3/group. The left panel shows photographs in which Wnt5a immunohistochemistry (IHC) was performed on resected Braf$^{V600E}$Pten$^{-/-}$-NTC or -Wnt5aKD melanoma tissues (scale bar, 1 cm). The right panel shows representative IFN-γ ELISPOT plates based on three independent experiments.
Figure 13B:
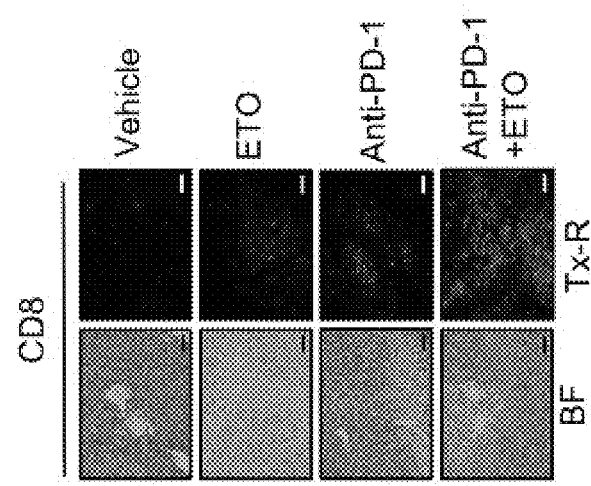
FIG. 13B shows representative images of immunofluorescent (IF) detection of Cd274 in Braf$^{V600E}$Pten$^{-/-}$-NTC and Braf$^{V600E}$Pten$^{-/-}$-Wnt5a$^{KD}$ melanomas (scale bar, 1 cm). The right panel shows a bar graph of Cd274 mRNA levels in these cells based on qRT-PCR analysis. n=3/group.
Figure 13C:
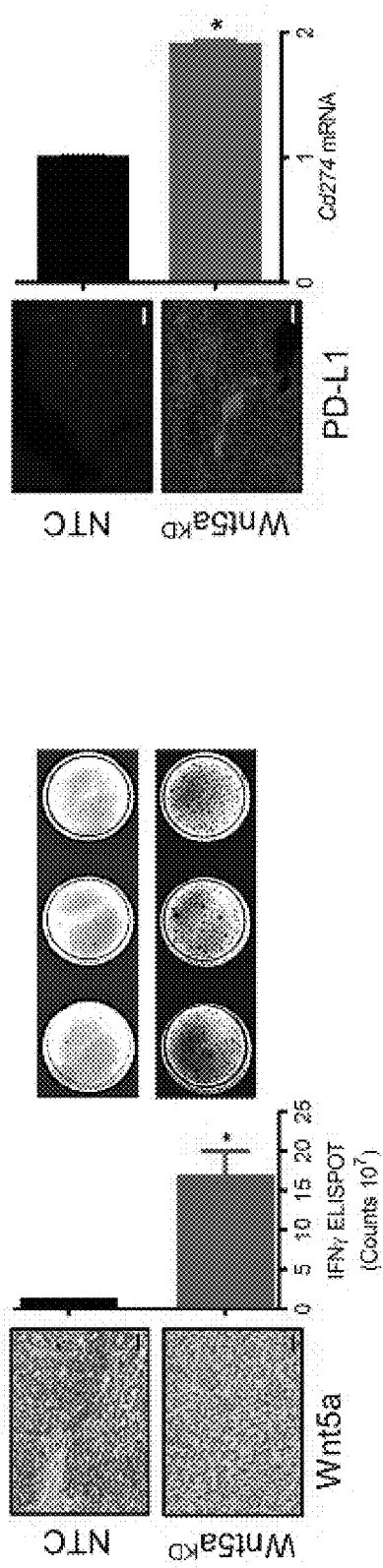
FIG. 13C shows a scatterplot of tumor volume over time, representing Braf$^{V600E}$Pten$^{-/-}$ melanoma growth in C57BL/6 mice undergoing treatment with vehicle and IgG isotype control, ETO and IgG isotype control, anti-PD-1 antibody and vehicle control, or anti-PD-1 antibody and ETO. n=6/group.
Figure 13D:
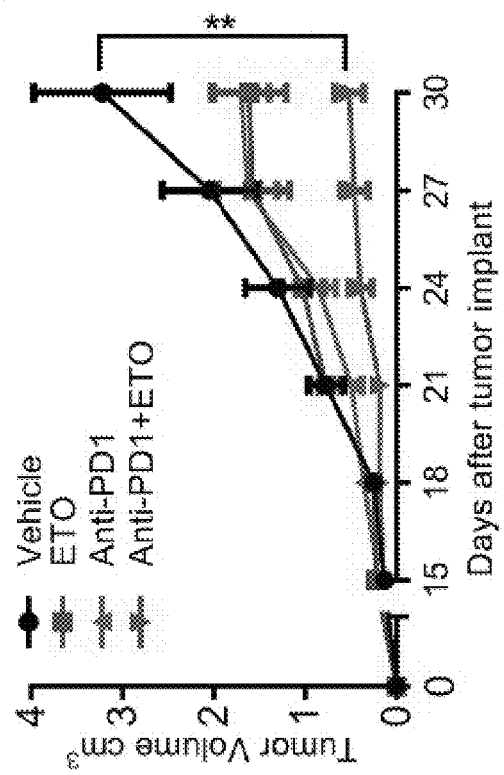
FIG. 13D shows IHC (left, BF: bright field) and IF (right, Tx-R: Texas Red) images probing for CD8$^+$ TIL in Braf$^{V600E}$Pten$^{-/-}$ melanomas resected from mice undergoing the indicated treatment (scale bar, 1 cm). Images are representative of three tumors/group.

Inhibition of Fatty Acid Oxidation Enhances Anti-PD-1 Antibody Therapy and Suppresses the Progression of an Autochthonous Melanoma Model The previous results suggest that a paracrine signaling axis mediated by melanoma-expressed Wnt5a induces FAO in local DCs to generate an immunotolerant microenvironment. To assess the impact of melanoma Wnt5a expression on T cell activity in melanoma, we performed IFN-γ ELIS-POT assays on tumor-infiltrating lymphocytes (TILs) harvested from BrafV600E-Pten-/--NTC and BrafV600E-Pten-/--Wnt5a-silenced tumors. We observed a significant enhancement in IFN-γ-expressing TILs within BrafV600E-Pten-/--Wnt5a-silenced tumors compared to control tumors, further supporting the immunotolerant role for Wnt5a (FIG. 13A). These findings were also associated with elevated Cd274 (PD-L1) expression based on qRT-PCR and immunofluorescence analysis of resected BrafV600E-Pten-/--Wnt5a-silenced tumor tissues (FIG. 13B). Since previous studies have indicated that an inflamed tumor environment characterized by elevated PD-L1 expression is associated with improved responses to anti-PD-1 antibody checkpoint inhibitor therapy, we proposed that pharmacological inhibition of FAO by targeting CPT1A downstream of Wnt5a would augment anti-PD-1 antibody immunotherapy (Spranger et al., 2013). We noted that ETO treatment of BrafV600E-Pten−/− tumor cells has no impact on the intrinsic proliferative capacity of this tumor model (FIG. 14A-14B). Therefore, any impact of ETO on the efficacy of anti-PD-1 antibody therapy would likely involve the stimulation of anti-tumor immunity. To test this hypothesis, we subcutaneously injected BrafV600E-Pten−/− melanoma cells into syngeneic C57BL/6 mice. Once tumors reached a volume of 80-100 mm$^3$, mice were treated with vehicle, ETO inhibitor, anti-PD-1 antibody, or both ETO inhibitor and anti-PD-1 antibody. Primary tumor volumes were monitored, and melanoma antigen-specific CD8+ T cell responses were quantified by IFN-γ ELISPOT assays. These data showed that ETO-mediated CPT1A inhibition suppresses the progression of BrafV600E-Pten−/− melanoma similarly to anti-PD-1 antibody monotherapy, while combination anti-PD-1 antibody-ETO therapy resulted in a significant reduction in primary melanoma growth (FIG. 13C). Reduced tumor growth correlated with enhanced numbers of CD8+ TILs in combination anti-PD-1 antibody-ETO-treated tumors and a more pronounced induction of TRP2-specific CD8+ T cells, suggesting this synergism is dependent on induction of an effective anti-tumor T cell response (FIG. 13D-13E). Further work showed ablation of CD8+ T cells in the host eliminated the ability of ETO to suppress BrafV600E-Pten−/− melanoma progression, confirming that FAO inhibition mediates anti-tumor activity in an immune-dependent manner (FIG. 13F and FIG. 14B). These results indicate FAO modulates anti-tumor immunity and is consistent with our previous data suggesting inhibition of the Wnt5a-β-catenin signaling pathway in DCs augments checkpoint inhibitor efficacy (Holtzhausen et al., 2015).

To investigate the impact of DC-specific FAO inhibition on melanoma progression, primary DCs were treated with Wnt5a with or without ETO prior to their transfer into the draining lymph node bed of developing autochthonous BrafV600E-Pten−/− transgenic melanomas (FIG. 13G). Consistently, DC-specific FAO inhibition potently suppressed primary melanoma progression (FIG. 13H). Correlative studies showed this effect also coincides with a suppression of Treg cells within local draining lymph node tissues and enhanced numbers of melanoma-infiltrating CD8+ T cells (FIG. 13I). Together, these data suggest the DC Wnt5a-β-catenin-PPAR-γ-CPT1A signaling axis is a pharmacologic target for enhancing the efficacy of cancer immunotherapy.

Discussion

In light of the critical role of DCs in driving effective anti-tumor immunity, we focused on elucidating those tumor-derived mechanisms that impair DC function (Gabrilovich, 2004). Indeed, there is emerging evidence that implicates DC tolerization in tumorigenesis (Hanks et al., 2013, Scarlett et al., 2012). This report demonstrates that melanomas induce local immune tolerance by manipulating the metabolism of DCs within the tumor microenvironment via a paracrine Wnt-β-catenin signaling pathway. Contrary to recently proposed theories that upregulation of IDO strictly represents a negative feedback mechanism of adaptive anti-tumor immunity (Spranger et al., 2013), we define an immune evasion mechanism that has evolved to actively manipulate IDO functionality.

Previous studies have suggested that DC tolerization depends on the β-catenin signaling pathway; however, the mechanisms by which tumors control this DC tolerization program and how this pathway ultimately drives immune tolerance has remained unclear (Jiang et al., 2007, Manicassamy et al., 2010). An understanding of these mechanisms could provide pharmacological targets to reverse the immunotolerant microenvironment. We recently demonstrated that melanoma expression of Wnt5a triggers β-catenin-dependent induction of DC IDO expression via a paracrine signaling pathway, and this culminates in driving local Treg cell differentiation (Holtzhausen et al., 2015). Others have shown that cellular metabolism regulates DC function, as TLR-induced DC maturation is critically dependent upon glycolysis and OXPHOS promotes the development of a pro-tolerogenic state (Everts et al., 2014, Malinarich et al., 2015). Additional studies have described a role for Wnt5a in the regulation of cellular metabolism (Sherwood et al., 2014). Thus, we hypothesized that melanoma-expressed Wnt5a metabolically reprograms DCs, and this functions as a central mechanism of tumor-mediated immune tolerance.

The data presented here demonstrate that melanoma-derived Wnt5a robustly shifts DCs toward OXPHOS in a manner that is dominant over LPS-induced glycolysis (Everts et al., 2014). Others have suggested that AMPK plays an important role in shifting DC metabolism from glycolysis to an OXPHOS-favored state; however, our data suggest that Wnt5a-mediated metabolic reprogramming of DCs is independent of AMPK. After determining that Wnt5a-stimulated DCs were not reliant on glutamine as an energy source for undergoing tolerization and that Wnt5a-stimulated DCs exhibit both enhanced fatty acid uptake and greater lipid stores, we reasoned that DC FAO was critical for driving this phenotype. Notably, a role for FAO in DC tolerance would also be consistent with the metabolic alterations observed in M2 macrophages and myeloid-derived suppressor cells (MDSCs) (Hossain et al., 2015, O'Neill and Pearce, 2016). Indeed, pharmacologically or genetically inhibiting FAO dominantly inhibited DC-mediated Treg cell generation and potently promoted DC-dependent stimulation of CD8+ T cell proliferation. The underlying mechanism of Wnt5a-induced FAO in DCs involves β-catenin-dependent PPAR-γ-mediated expression of CPT1A. We further demonstrate that β-catenin and PPAR-γ form a co-transcriptional activator complex in primary DCs upon Wnt5a exposure, and this DC signaling pathway modulates the development of melanoma antigen-specific T cell responses in vivo. These cumulative findings may also explain the induction of FAO in M2 macrophages and MDSCs within the tumor microenvironment.

While the cellular oxidative state has been shown to regulate IDO enzyme activity, to our knowledge a relationship between metabolic regulation and the enzymatic activity of IDO has not been appreciated (Thomas et al., 2001). Here, we have shown that Wnt5a drives heme biosynthesis and the accumulation of the PpIX prosthetic group by promoting both TCA flux and the expression of several enzymes involved in this pathway and the heme biosynthetic pathway including the rate-limiting enzyme, ALAS1. Since PpIX is a limiting factor of IDO activity (Thomas et al., 2001), we propose that this pathway is a previously unrecognized mechanism of IDO regulation. Although we were unable to measure the metabolic intermediate succinyl CoA due to its relative instability, the diminished quantities of the α-ketoglutarate precursor and the increased expression of each component of the α-ketoglutarate dehydrogenase complex in addition to ALAS1 suggest that Wnt5a-mediated metabolic reprogramming promotes heme synthesis by providing increased quantities of substrate while upregulating the expression of key TCA and heme synthesis enzymes.

Our data indicate that FAO in DCs has an impact on DC tolerization that extends beyond IDO. This led us to discover that this metabolic shift potently suppresses two key pro-inflammatory cytokines, IL-6 and IL-12, which contribute to a more favorable mileu for driving Treg cell differentiation. In particular, IL-6 antagonizes Treg cell development in several experimental systems by promoting the proteosomal degradation of IDO (Orabona et al., 2008). These effects on pro-inflammatory cytokine expression by DCs are consistent with previous work showing that Wnt5a suppresses upregulation of these same cytokines in response to LPS (Oderup et al., 2013). Given that FAO in DCs can influence multiple biochemical pathways important for DC tolerization, we speculate that targeting regulators of DC-specific FAO could potently impact the tumor immune microenvironment. Indeed, we have demonstrated that genetic silencing of CPT1A in primary DCs promotes antigen-specific CD8+ T cell activation, and adoptive transfer of DCs treated with a pharmacologic FAO inhibitor significantly suppressed melanoma progression in a poorly immunogenic transgenic model of melanoma. Together, these data suggest that targeting the Wnt5a-β-catenin-FAO pathway represents a promising strategy for augmenting checkpoint inhibitor immunotherapy. This is consistent with the robust effect generated by combining a CPT1A-targeted inhibitor with anti-PD-1 antibody therapy in the BrafV600E-Pten−/− melanoma model. Further, since the Wnt5a-β-catenin-FAO pathway regulates several components of DC tolerization that extend beyond IDO, we propose that designing strategies to inhibit this pathway upstream of IDO may be more effective at inducing anti-tumor immunity than strictly targeting the activity of this enzyme.

Melanomas with few TILs and a generally non-inflamed microenvironment are poorly responsive to checkpoint inhibitor therapy. In line with our mechanistic DC studies, recent gene expression profiling based on microarray and RNA-seq datasets have demonstrated that primary melanomas, as well as other solid tumors, associated with a deficiency in TILs are associated with elevated β-catenin and PPAR-γ signaling (Spranger et al., 2015, Sweis et al., 2016). Despite this finding, a minority of these "TIL-poor" cancers harbor genomic mutations that drive the β-catenin signaling pathway (Luke et al., 2016), suggesting that Wnt-mediated paracrine signaling pathways likely contribute to the elevated β-catenin activation state observed in these non-inflamed tumors. In this work, we have provided functional data indicating that Wnt5a promotes the establishment of an immune-privileged, "TIL-poor" melanoma microenvironment by driving FAO in DCs. The importance of Wnt5a in promoting an immune-tolerant state is supported by a recent report employing RNA-seq differential gene expression analysis demonstrating Wnt5a is one of the most significantly upregulated genes in melanomas refractory to pembrolizumab immunotherapy (Hugo et al., 2016).

Altogether, these findings demonstrate that DC tolerization in the tumor microenvironment contributes to immunotherapy resistance and that Wnt ligand antagonism would be a promising strategy for augmenting anti-PD-1 antibody immunotherapy. Finally, these data further advocate for DC-specific manipulation of the FAO pathway as an approach for designing the next generation of DC-based cancer vaccines.

| REAGENT or RESOURCE | SOURCE | IDENTIFIER |
|---|---|---|
| Antibodies | | |
| Anti-b-actin antibody, clone: C4 | Santa Cruz Biotechnology | RRID: AB_2714189 |
| Anti-CPT1A Rabbit mAb, clone: D3B3 | Cell Signaling | 12252 |
| Anti-PPAR-g Antibody, clone: H-100 | Santa Cruz Biotechnology | RRID: AB_654710 |
| Anti-b-catenin, rabbit polyclonal | Millipore Sigma | RRID: AB_310231 |
| Anti-Phospho-AMPKa (Thr172) rabbit mAb, clone: 40H9 | Cell Signaling | RRID: AB_331250 |
| Anti-AMPKa Rabbit mAb, clone: D5A2 | Cell Signaling | RRID: AB_10622186 |
| Anti-Phospho-Akt (Thr308) Antibody, rabbit polyclonal | Cell Signaling | RRID: AB_329828 |
| Anti-Akt Antibody, rabbit polyclonal | Cell Signaling | RRID: AB_329827 |
| Anti-Wnt5a Antibody, clone: A-5 | Santa Cruz Biotechnology | RRID: AB_10846090 |
| Anti-PD-L1 Rabbit mAb, Clone: D5V3B | Cell Signaling | 64988 |
| Anti-CD8a XP Rabbit mAb, Clone: D4W2Z | Cell Signaling | 98941 |
| Anti-mouse I-A/I-E(MHCII), Alexa Fluor 488 conjugated, clone: M5/114.15.2 | BD Pharmingen | RRID: AB_11151902 |
| Anti-Mouse CD11c, FITC conjugated, clone: HL3 | BD Pharmingen | RRID: AB_395060 |
| Anti-Mouse CD274, PE conjugated, clone: MIH5 | BD Pharmingen | RRID: AB_397018 |

-continued

| REAGENT or RESOURCE | SOURCE | IDENTIFIER |
| --- | --- | --- |
| Anti-Mouse CD8a, BV510 congugated, clone: 53-6.7 | BD Pharmingen | RRID: AB_2687548 |
| Anti-Mouse CD3e, PerCP-Cy5.5 congugated, clone: 145-2C11 | BD Pharmingen | RRID: AB_394082 |
| Anti-Mouse CD4, FITC congugated, clone: RM4-5 | BD Pharmingen | RRID: AB_394583 |
| Anti-Mouse Foxp3, PE congugated, clone: MF23 | BD Pharmingen | RRID: AB_1645251 |
| Anti-Mouse CD279, APC congugated, clone: J43 | BD Pharmingen | 562671 |
| Anti-mouse CD40 Pacific Blue conjugated, clone: 3/23 | Biolegend | RRID: AB_2561475 |
| Anti-mouse CD80, PerCP/Cy5.5 conjugated, clone: 16-10A1 | Biolegend | RRID: AB_2291392 |
| Anti-mouse CD86, APC conjugated, clone: GL-1 | Biolegend | RRID: AB_493342 |
| Anti-mouse F4/80 Antibody, APC congugated, clone: BM8 | Biolegend | RRID: AB_893481 |
| Anti-mouse IL-6, unconjugated, clone: MP5-20F3 | Biolegend | RRID: AB_315339 |
| Anti-mouse IL-12/IL23 p40, unconjugated, clone: C17.8 | Biolegend | RRID: AB_315375 |
| Goat Anti-Rabbit IgG (H + L)-HRP Conjugate | Bio-Rad | RRID: AB_11125143 |
| Goat Anti-Mouse IgG (H + L)-HRP Conjugate | Bio-Rad | RRID: AB_11125547 |
| InVivoMAB Anti-mouse PD-1, clone: RMP1-14 | BioXCell | RRID: AB_10949053 |
| InVivoMAb rat IgG2a isotype control, clone: 2A3 | BioXCell | RRID: AB_1107769 |
| Anti-mouse CD8 antibody from hybridoma, clone: 53.6.7 | Duke Cell Culture Facility | N/A |
| Chemicals, Peptides, and Recombinant Proteins | | |
| Recombinant Human/Mouse Wnt5a Protein | R&D Systems | 645-WN-010 |
| Recombinant Mouse Wnt3a Protein | R&D Systems | 1324-WN-002 |
| Recombinant Mouse IL-4 | BioAbChem | 42-IL4 |
| Recombinant Mouse GM-CSF Protein | R&D systems | 415-ML-010 |
| Glucose | Sigma-Aldrich | G7021-100G |
| Oligomycin | Sigma-Aldrich | O4876-25MG |
| 2-DG (2-Deoxy-D-glucose) | Sigma-Aldrich | D3179-1G |
| FCCP (Carbonyl cyanide 4-(trifluoromethoxy)phenylhydrazone) | Sigma-Aldrich | C2920-10MG |
| Rotenone | Sigma-Aldrich | 557368-1GM |
| Antimycin A | Sigma-Aldrich | A8674-50MG |
| (+)-Etomoxir sodium salt hydrate | Sigma-Aldrich | E1905-25MG |
| 4-hydroxytamoxifen | Sigma-Aldrich | H6278-10MG |
| L-tryptophan | Sigma-Aldrich | T4196-100G |
| L-kynurenine | Sigma-Aldrich | K8625-25MG |

-continued

| REAGENT or RESOURCE | SOURCE | IDENTIFIER |
|---|---|---|
| BPTES | Sigma-Aldrich | SML0601-5MG |
| AICAR | Sigma-Aldrich | A9978-5MG |
| XAV939 | Sigma-Aldrich | X3004-5MG |
| noble agar | Sigma-Aldrich | A5431-250G |
| NAD+ (b-Nicotinamide adenine dinucleotide) | Sigma-Aldrich | N6522 |
| Polyethylene glycol(PEG)-8000 | Sigma-Aldrich | 89510-250G-F |
| L-Lactic Dehydrogenase from rabbit muscle | Sigma-Aldrich | L2500-10KU |
| Glycine Buffer solution | Sigma-Aldrich | G5418-100ML |
| Sodium L-lactate | Sigma-Aldrich | L7022 |
| LPS (Lipopolysaccharides) | Sigma-Aldrich | L4391-1MG |
| ALA (5-Aminolevulinic acid hydrochloride) | Sigma-Aldrich | A3785-1G |
| Succinylacetone(4,6-Dioxoheptanoic acid) | Sigma-Aldrich | D1415-100MG |
| BODIPY 493/503 | ThermoFisher | D-3922 |
| BIO (GSK-3 Inhibitor IX) | Millipore | 361550-1MG |
| MeBIO(GSK-3 Inhibitor IX, Control) | Millipore | 361556-1MG |
| Critical Commercial Assays | | |
| CD11c MicroBeads UltraPure, mouse | Miltenyi Biotec | 130-108-338 |
| Naive CD4+ T Cell Isolation Kit, mouse | Miltenyi Biotec | 130-104-453 |
| RNeasy Plus Mini Kit | Qiagen | 74134 |
| Fatty Acid Uptake Kit | Sigma-Aldrich | MAK156-1KT |
| Prime PCR PCR Array PPAR targets M96 | Bio-Rad | 10034399 |
| Hemin kit | BioVision | K672 |
| Seahorse XFe24 FluxPaks | Agilent | 102342-100 |
| Annexin V-FITC Apoptosis Detection Kit | Sigma-Aldrich | APOAF-20TST |
| ATP Determination Kit | ThermoFisher | A22066 |
| Mouse IFN-g ELISpot PLUS (ALP) | MABTECH | 3321-4APW-2 |
| Mouse IL6 ELISA Kit | ThermoFisher (eBioscience) | 50-112-8863 |
| Mouse IL12(p40) ELISA Set | BD Biosciences | 555165 |
| Warp Red Chromogen Kit | Biocare | WR806 S |
| CellTrace Violet Cell Proliferation Kit | ThermoFisher | C34571 |
| SsoAdvanced Universal SYBR Green Supermix | BIO-Rad | 1725271 |
| iScript Reverse Transcription Supermix | BIO-Rad | 1708841 |
| SsoAdvance Universal Probes Supermix | BIO-Rad | 172-5281 |
| Pierce Gentle Ag/Ab Binding and Elution Buffer Kit | ThermoFisher | 21030 |

-continued

| REAGENT or RESOURCE | SOURCE | IDENTIFIER |
|---|---|---|
| *Experimental Models: Cell Lines* | | |
| BRAF$^{V600E}$PTEN-/-melanoma cells | Hanks Lab | PMID: 26041736 |
| BRAF$^{V600E}$PTEN-/--NTC | Hanks Lab | PMID: 26041736 |
| BRAF$^{V600E}$PTEN-/--Wnt5a$^{KD}$ | Hanks Lab | PMID: 26041736 |
| DC2.4 | Rock Lab | RRID: CVCL_J409 |
| DC2.4-NTC | Hanks Lab | this paper |
| DC2.4-CPT1A$^{KD}$ | Hanks Lab | this paper |
| DC2.4-b-catenin$^{KD}$ | Hanks Lab | this paper |
| *Experimental Models: Organisms/Strains* | | |
| Mouse: C57BL/6J | Jackson Laboratory | RRID: IMSR_JAX: 000664 |
| Mouse: BALB/cJ | Jackson Laboratory | RRID: IMSR_JAX: 000651 |
| Mouse: B6.Cg-Braf$^{tm1Mmcm}$ Pten$^{tm1Hwu}$ Tg(Tyr-cre/ERT2 H-2$^b$) 13Bos/BosJ | Jackson Laboratory | RRID: IMSR_JAX: 012328 |
| Mouse: C57BL/6-Tg(TcraTcrb)1100Mjb/J | Jackson Laboratory | RRID: IMSR_JAX: 003831 |
| Mouse: B6.129-Ido$^{tm1Alm}$/J | Jackson Laboratory | RRID: IMSR_JAX: 005867 |
| Mouse: C57BL/6-Foxp3$^{tm1Flv}$/J | Jackson Laboratory | RRID: IMSR_JAX: 008374 |
| Mouse: CD11c-bcat-/- | Manicassamy Lab | PMID: 25710911 |
| *Recombinant DNA* | | |
| Mission shRNA Plasmid DNA against CPT1A | Sigma-Aldrich | SHCLND-NM_013495 |
| Mission shRNA Plasmid DNA against CTNNB1(b-catenin) | Sigma-Aldrich | SHCLND-NM_001904 |
| Mission shRNA Plasmid DNA against Wnt5a | Sigma-Aldrich | SHCLND-NM_009524 |
| Mission pLKO.1-puro Empty vector Control Plasmid | Sigma-Aldrich | SHC001 |
| *Oligonucleotides* | | |
| Primer: mACTB Forward: GGCTGTATTCCCCTCCATCG (SEQ ID NO: 1) | IDT | N/A |
| Primer: mACTB Reverse: CCAGTTGGTAACAATGCCATGT (SEQ ID NO: 2) | IDT | N/A |
| Primer: mPPARg Forward: GCCCTTTGGTGACTTTATGGA (SEQ ID NO: 3) | IDT | N/A |
| Primer: mPPARg Reverse: GCAGCAGGTTGTCTTGGATG (SEQ ID NO: 4) | IDT | N/A |
| Primer: mCPT1A Forward: CTCAGTGGGAGCGACTCTTCA (SEQ ID NO: 5) | IDT | N/A |
| Primer: mCPT1A Reverse: GGCCTCTGTGGTACACGACAA (SEQ ID NO: 6) | IDT | N/A |

| REAGENT or RESOURCE | SOURCE | IDENTIFIER |
| --- | --- | --- |
| Primer: mCPT1B Forward:<br>TTCAACACTACACGCATCCC<br>(SEQ ID NO: 7) | IDT | N/A |
| Primer: mCPT1B Reverse:<br>GCCCTCATAGAGCCAGACC<br>(SEQ ID NO: 8) | IDT | N/A |
| Primer: mCPT1C Forward:<br>TCTTCACTGAGTTCCGATGGG<br>(SEQ ID NO: 9) | IDT | N/A |
| Primer: mCPT1C Reverse:<br>ACGCCAGAGATGCCTTTTCC<br>(SEQ ID NO: 10) | IDT | N/A |
| Primer: mIL6 Forward:<br>TAGTCCTTCCTACCCCAATTTCC<br>(SEQ ID NO: 11) | IDT | N/A |
| Primer: mIL6 Reverse:<br>TTGGTCCTTAGCCACTCCTTC<br>(SEQ ID NO: 12) | IDT | N/A |
| Primer: mIL10 Forward:<br>GACCAGCTGGACAACATAC<br>(SEQ ID NO: 13) | IDT | N/A |
| Primer: mIL10 Reverse:<br>CTGGAGTCCAGCAGACTC<br>(SEQ ID NO: 14) | IDT | N/A |
| Primer: mIL12B Forward:<br>GAACACATGCCCACTTGCTG<br>(SEQ ID NO: 15) | IDT | N/A |
| Primer: mIL12B Reverse:<br>CGTGCTCATGGCTGGTGCAAAG<br>(SEQ ID NO: 16) | IDT | N/A |
| Primer: mTGFb Forward:<br>GCAACAACGCCATCTATGAG<br>(SEQ ID NO: 17) | IDT | N/A |
| Primer: mTGFb Reverse:<br>TCTTTGCTGTCACAAGAGC<br>(SEQ ID NO: 18) | IDT | N/A |
| Primer: mPFK Forward:<br>GGAGGCGAGAACATCAAGCC<br>(SEQ ID NO: 19) | IDT | N/A |
| Primer: mPFK Reverse:<br>CGGCCTTCCCTCGTAGTGA<br>(SEQ ID NO: 20) | IDT | N/A |
| Primer: mHK3 Forward:<br>TGCTGCCCACATACGTGAG<br>(SEQ ID NO: 21) | IDT | N/A |
| Primer: mHK3 Reverse:<br>CCTGTCAGTGTTACCCACAA<br>(SEQ ID NO: 22) | IDT | N/A |
| Primer: mCTNNB Forward:<br>TCCCATCCACGCAGTTTGAC<br>(SEQ ID NO: 23) | IDT | N/A |
| Primer: mCTNNB Reverse:<br>TCCTCATCGTTTAGCAGTTTTGT<br>(SEQ ID NO: 24) | IDT | N/A |
| Primer: mALAS1 Forward:<br>GATGCCAGGCTGTGAAATTTACT<br>(SEQ ID NO: 25) | IDT | N/A |

| REAGENT or RESOURCE | SOURCE | IDENTIFIER |
|---|---|---|
| Primer: mALAS1 Reverse: CTGTTGCGAATCCCTTGGAT (SEQ ID NO: 26) | IDT | N/A |
| Primer: mGAPDH Forward: GTCTACATGTTCCAGTATGACTCC (SEQ ID NO: 27) | IDT | N/A |
| Primer: mGAPDH Reverse: AGTGAGTTGTCATATTTCTCGTGGT (SEQ ID NO: 28) | IDT | N/A |
| Software and Algorithms | | |
| Wave Desktop 2.4 | Agilent | www.agilent.com/ |
| Graphpad Prism 7 | GraphPad Software | www.graphpad.com/ |
| ImageJ | NIH | RRID: SCR_003070 |
| FlowJo v10.3 | Flowjo | www.flowjo.com/ |
| PrimePCR Analysis | Bio-Rad | www.bio-rad.com |
| Image Lab | Bio-Rad | www.bio-rad.com |
| 7500 software v2.3 | Applied Biosystems | www.thermofisher.com/us/en/home.html |
| ImmunoSpot 5.0 | ImmunoSpot | www.immunospot.com |
| ImmunoCapture6.3.5 | ImmunoSpot | www.immunospot.com |

References for Example 1

Banchereau, J., and Steinman, R. M. (1998). Dendritic cells and the control of immunity. Nature 392, 245-252.

Collier, G. R., Traianedes, K., Macaulay, S. L., and O'Dea, K. (1993). Effect of fatty acid oxidation inhibition on glucose metabolism in diabetic rats. Horm Metab Res. 25, 9-12.

Everts, B., Amiel, E., Huang, S. C., Smith, A. M., Chang, C. H., Lam, W. Y., Redmann, V., Freitas, T. C., Blagih, J., van der Windt, G. J., et al. (2014). TLRdrivenearly glycolytic reprogramming via the kinases TBK1-IKK 3 supports the anabolic demands of dendritic cell activation. Nat. Immunol. 15, 323-332.

Fallarino, F., Grohmann, U., You, S., McGrath, B. C., Cavener, D. R., Vacca, C., Orabona, C., Bianchi, R., Belladonna, M. L., Volpi, C., et al. (2006). The combined effects of tryptophan starvation and tryptophan catabolites down-regulate T cell receptor zeta-chain and induce a regulatory phenotype in naive T cells. J. Immunol. 176, 6752-6761.

Gabrilovich, D. (2004). Mechanisms and functional significance of tumourinduced dendritic-cell defects. Nat. Rev. Immunol. 4, 941-952.

Handschin, C., Lin, J., Rhee, J., Peyer, A. K., Chin, S., Wu, P. H., Meyer, U. A., and Spiegelman, B. M. (2005). Nutritional regulation of hepatic heme biosynthesis and porphyria through PGC-1alpha. Cell 122, 505-515.

Hanks, B. A., Holtzhausen, A., Evans, K. S., Jamieson, R., Gimpel, P., Campbell, O. M., Hector-Greene, M., Sun, L., Tewari, A., George, A., et al. (2013). Type III TGF-b receptor downregulation generates an immunotolerant tumor microenvironment. J. Clin. Invest. 123, 3925-3940.

Herber, D. L., Cao, W., Nefedova, Y., Novitskiy, S. V., Nagaraj, S., Tyurin, V. A., Corzo, A., Cho, H. I., Celis, E., Lennox, B., et al. (2010). Lipid accumulation and dendritic cell dysfunction in cancer. Nat. Med. 16, 880-886.

Holtzhausen, A., Zhao, F., Evans, K. S., Tsutsui, M., Orabona, C., Tyler, D. S., and Hanks, B. A. (2015). Melanoma-derived Wnt5a promotes local dendriticcell expression of IDO and immunotolerance: opportunities for pharmacologic enhancement of immunotherapy. Cancer Immunol. Res. 3, 1082-1095.

Hossain, F., Al-Khami, A. A., Wyczechowska, D., Hernandez, C., Zheng, L., Reiss, K., Valle, L. D., Trillo-Tinoco, J., Maj, T., Zou, W., et al. (2015). Inhibition of fatty acid oxidation modulates immunosuppressive functions of myeloid-derived suppressor cells and enhances cancer therapies. Cancer Immunol. Res. 3, 1236-1247.

Hryhorenko, E. A., Rittenhouse-Diakun, K., Harvey, N. S., Morgan, J., Stewart, C. C., and Oseroff, A. R. (1998). Characterization of endogenous protoporphyrin IX induced by delta-aminolevulinic acid in resting and activated peripheral blood lymphocytes by four-color flow cytometry. Photochem. Photobiol. 67, 565-572.

Hugo, W., Zaretsky, J. M., Sun, L., Song, C., Moreno, B. H., Hu-Lieskovan, S., Berent-Maoz, B., Pang, J., Chmielowski, B., Cherry, G., et al. (2016). Genomic and transcriptomic features of response to anti-PD-1 therapy in metastatic melanoma. Cell 165, 35-44.

Inaba, K., Inaba, M., Romani, N., Aya, H., Deguchi, M., Ikehara, S., Muramatsu, S., and Steinman, R. M. (1992). Generation of large numbers of dendritic cells from mouse bone marrow cultures supplemented with granulocyte/macrophage colony-stimulating factor. J. Exp. Med. 176, 1693-1702.

Jansson, E. A., Are, A., Greicius, G., Kuo, I. C., Kelly, D., Arulampalam, V., and Pettersson, S. (2005). The Wnt/beta-catenin signaling pathway targets PPARgamma activity in colon cancer cells. Proc. Natl. Acad. Sci. USA 102, 1460-1465.

Jiang, A., Bloom, O., Ono, S., Cui, W., Unternaehrer, J., Jiang, S., Whitney, J. A., Connolly, J., Banchereau, J., and Mellman, I. (2007). Disruption of E-cadherin-mediated adhesion induces a functionally distinct pathway of dendritic cell maturation. Immunity 27, 610-624.

Krawczyk, C. M., Holowka, T., Sun, J., Blagih, J., Amiel, E., DeBerardinis, R. J., Cross, J. R., Jung, E., Thompson, C. B., Jones, R. G., and Pearce, E. J. (2010). Toll-like receptor-induced changes in glycolytic metabolism regulate dendritic cell activation. Blood 115, 4742-4749.

Liu, X., Ser, Z., Cluntun, A. A., Mentch, S. J., and Locasale, J. W. (2014a). A strategy for sensitive, large scale quantitative metabolomics. J. Vis. Exp. (87) https://doi.org/10.3791/51358.

Liu, X., Ser, Z., and Locasale, J. W. (2014b). Development and quantitative evaluation of a high-resolution metabolomics technology. Anal. Chem. 86, 2175-2184.

Luke, J. J., Bao, R., Spranger, S., Sweis, R. F., and Gajewski, T. F. (2016). Correlation of WNT/b-catenin pathway activation with immune exclusion across most human cancers. J. Clin. Oncol. 34.

Malinarich, F., Duan, K., Hamid, R. A., Bijin, A., Lin, W. X., Poidinger, M., Fairhurst, A. M., and Connolly, J. E. (2015). High mitochondrial respiration and glycolytic capacity represent a metabolic phenotype of human tolerogenic dendritic cells. J. Immunol. 194, 5174-5186.

Manicassamy, S., Reizis, B., Ravindran, R., Nakaya, H., Salazar-Gonzalez, R. M., Wang, Y. C., and Pulendran, B. (2010). Activation of beta-catenin in dendritic cells regulates immunity versus tolerance in the intestine. Science 329, 849-853.

Mellor, A. L., and Munn, D. H. (2008). Creating immune privilege: active local suppression that benefits friends, but protects foes. Nat. Rev. Immunol. 8, 74-80.

Mullard, A. (2015). Immunotherapy interest drives IDO deals. Nat. Rev. Drug Discov. 14, 373.

Munn, D. H., and Mellor, A. L. (2007). Indoleamine 2,3-dioxygenase and tumorinduced tolerance. J. Clin. Invest. 117, 1147-1154.

Munn, D. H., Sharma, M. D., Lee, J. R., Jhaver, K. G., Johnson, T. S., Keskin, D. B., Marshall, B., Chandler, P., Antonia, S. J., Burgess, R., et al. (2002). Potential regulatory function of human dendritic cells expressing indoleamine 2,3-dioxygenase. Science 297, 1867-1870.

Munn, D. H., Sharma, M. D., Hou, D., Baban, B., Lee, J. R., Antonia, S. J., Messina, J. L., Chandler, P., Koni, P. A., and Mellor, A. L. (2004). Expression of indoleamine 2,3-dioxygenase by plasmacytoid dendritic cells in tumordraining lymph nodes. J. Clin. Invest. 114, 280-290.

Nair, S., Archer, G. E., and Tedder, T. F. (2012). Isolation and generation of human dendritic cells. In Current Protocols in Immunology (John Wiley & Sons). https://doi.org/10.1002/0471142735.im0732s99, 7.32.

O'Neill, L. A., and Pearce, E. J. (2016). Immunometabolism governs dendritic cell and macrophage function. J. Exp. Med. 213, 15-23.

Oderup, C., LaJevic, M., and Butcher, E. C. (2013). Canonical and noncanonical Wnt proteins program dendritic cell responses for tolerance. J. Immunol. 190, 6126-6134.

Orabona, C., Pallotta, M. T., Volpi, C., Fallarino, F., Vacca, C., Bianchi, R., Belladonna, M. L., Fioretti, M. C., Grohmann, U., and Puccetti, P. (2008). SOCS3 drives proteasomal degradation of indoleamine 2,3-dioxygenase (IDO) and antagonizes IDO-dependent tolerogenesis. Proc. Natl. Acad. Sci. USA 105, 20828-20833.

Pallotta, M. T., Orabona, C., Volpi, C., Vacca, C., Belladonna, M. L., Bianchi, R., Servillo, G., Brunacci, C., Calvitti, M., Bicciato, S., et al. (2011). Indoleamine 2,3-dioxygenase is a signaling protein in long-term tolerance by dendritic cells. Nat. Immunol. 12, 870-878.

Pesce, M. A., Bodourian, S. H., and Nicholson, J. F. (1975). Rapid kinetic measurement of lactate in plasma with a centrifugal analyzer. Clin. Chem. 21, 1932-1934.

Salmon, H., Idoyaga, J., Rahman, A., Leboeuf, M., Remark, R., Jordan, S., Casanova-Acebes, M., Khudoynazarova, M., Agudo, J., Tung, N., et al. (2016). Expansion and activation of CD103(+) dendritic cell progenitors at the tumor site enhances tumor responses to therapeutic PD-L1 and BRAF inhibition. Immunity 44, 924-938.

Scarlett, U. K., Rutkowski, M. R., Rauwerdink, A. M., Fields, J., Escovar-Fadul, X., Baird, J., Cubillos-Ruiz, J. R., Jacobs, A. C., Gonzalez, J. L., Weaver, J., et al. (2012). Ovarian cancer progression is controlled by phenotypic changes in dendritic cells. J. Exp. Med. 209, 495-506.

Sharma, M. D., Baban, B., Chandler, P., Hou, D.-Y., Singh, N., Yagita, H., Azuma, M., Blazar, B. R., Mellor, A. L., and Munn, D. H. (2007). Plasmacytoid dendritic cells from mouse tumor-draining lymph nodes directly activate mature Tregs via indoleamine 2,3-dioxygenase. J. Clin. Invest. 117, 2570-2582.

Shen, Z., Reznikoff, G., Dranoff, G., and Rock, K. L. (1997). Cloned dendritic cells can present exogenous antigens on both MHC class I and class II molecules. J. Immunol. 158, 2723-2730.

Sherwood, V., Chaurasiya, S. K., Ekstro m, E. J., Guilmain, W., Liu, Q., Koeck, T., Brown, K., Hansson, K., Agnarsdo'ttir, M., Bergqvist, M., et al. (2014). WNT5A-mediated b-catenin-independent signalling is a novel regulator of cancer cell metabolism. Carcinogenesis 35, 784-794.

Shimizu, T., Nomiyama, S., Hirata, F., and Hayaishi, O. (1978). Indoleamine 2,3-dioxygenase. Purification and some properties. J. Biol. Chem. 253, 4700-4706.

Spranger, S., Spaapen, R. M., Zha, Y., Williams, J., Meng, Y., Ha, T. T., and Gajewski, T. F. (2013). Up-regulation of PD-L1, IDO, and T(regs) in the melanoma tumor microenvironment is driven by CD8(+) T cells. Sci. Transl. Med. 5, 200ra116.

Spranger, S., Bao, R., and Gajewski, T. F. (2015). Melanoma-intrinsic b-catenin signalling prevents anti-tumour immunity. Nature 523, 231-235.

Spranger, S., Dai, D., Horton, B., and Gajewski, T. F. (2017). Tumor-residing Batf3 dendritic cells are required for effector T cell trafficking and adoptive T cell therapy. Cancer Cell 31, 711-723 e714.

Sweis, R. F., Spranger, S., Bao, R., Paner, G. P., Stadler, W. M., Steinberg, G., and Gajewski, T. F. (2016). Molecular drivers of the non-T-cell-inflamed tumor microenvironment in urothelial bladder cancer. Cancer Immunol. Res. 4, 563-568.

Thomas, S. R., Salahifar, H., Mashima, R., Hunt, N. H., Richardson, D. R., and Stocker, R. (2001). Antioxidants inhibit indoleamine 2,3-dioxygenase in IFNgamma-activated human macrophages: posttranslational regulation by pyrrolidine dithiocarbamate. J. Immunol. 166, 6332-6340.

Zhao, F., and Klimecki, W. T. (2015). Culture conditions profoundly impact phenotype in BEAS-2B, a human pulmonary epithelial model. J. Appl. Toxicol. 35, 945-951.

Zhao, F., Malm, S. W., Hinchman, A. N., Li, H., Beeks, C. G., and Klimecki, W. T. (2014). Arsenite-induced pseudo-hypoxia results in loss of anchorage-dependent growth in BEAS-2B pulmonary epithelial cells. PLoS ONE 9, el 14549.

Example 2: Specific Biomarkers are Associated with Anti-PD-1 Antibody Immunotherapy Resistance and Relate to the Inflammasome-Wnt Ligand Signaling Axis Adaptive resistance to checkpoint inhibitor therapy includes negative feedback mechanisms inherent to the immune system and results in about 30% of eventual treatment failures in advanced melanoma and often a higher failure rate in solid tumors. This Example demonstrates that specific biomarkers are associated with immune checkpoint inhibitor resistant cancers, specifically anti-PD-1 antibody therapy. These biomarkers can be used as markers to determine and treat a subpopulation of cancer patients with Wnt-β-catenin inhibitors, which, when combined with anti-PD-1 therapy, result in increased reduction and suppression of tumor cell growth. The use of these biomarkers to determine anti-PD-1 antibody therapy resistance allows for the ability to target a population of cancer patients that may be able to be targeted with a Wnt inhibitor.

Figures 15A, 15B, 15C, 15D, 15E, 15F:
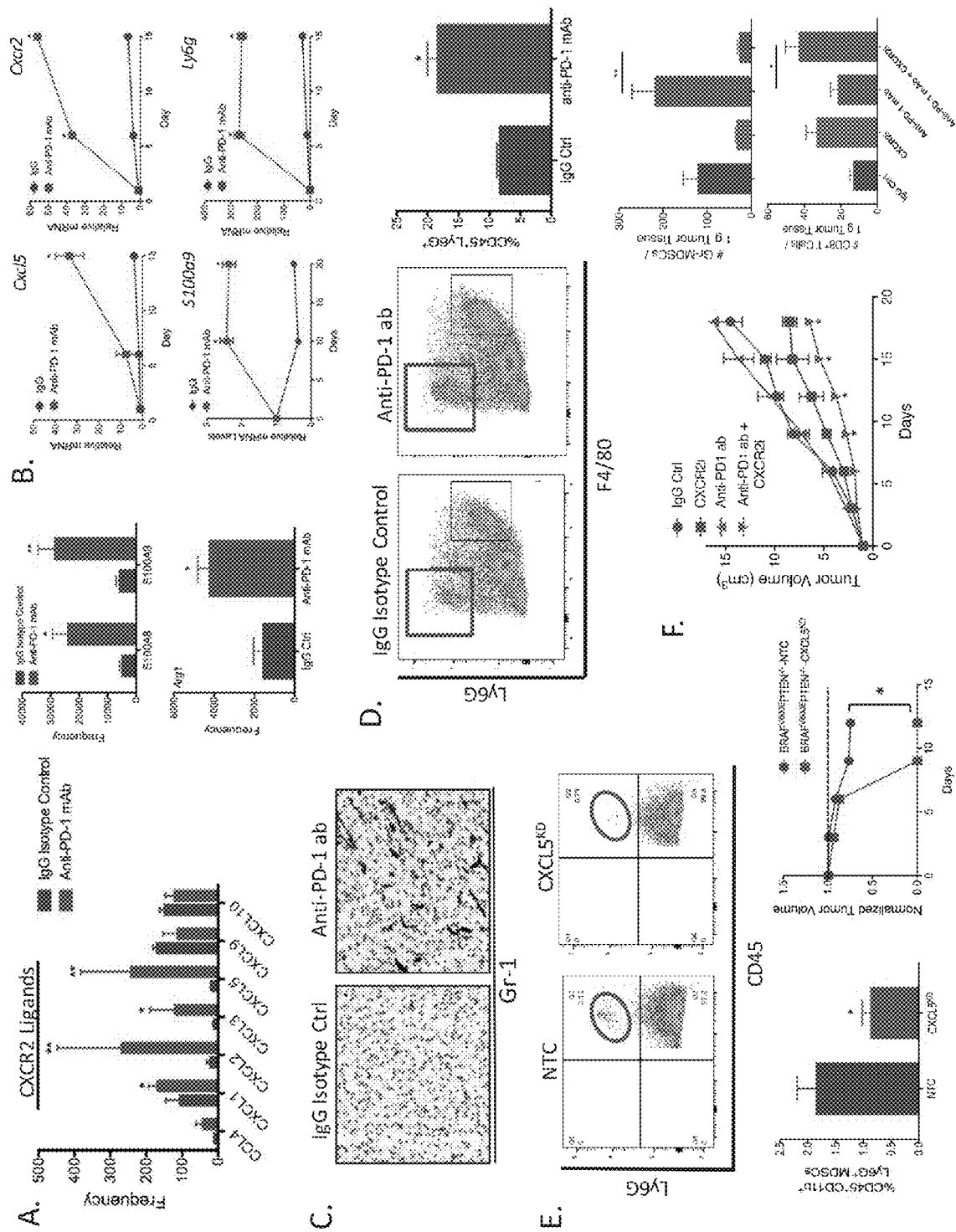
FIGS. 15A-15F demonstrate Gr-MDSC Accumulation Contributes to Tumor Progression through Anti-PD-1 Antibody Immunotherapy. (A) RNAseq differential gene expression analysis of resected tumor tissues following treatment of the autochthonous BRAF$^{V600E}$PTEN$^{-/-}$ melanoma model with anti-PD-1 ab therapy versus IgG isotype control. (n=3). (B) Qrt-PCR analysis of target genes of interest in serial tumor biopsy specimens harvested from the transgenic BRAF$^{V600E}$PTEN$^{-/-}$ melanoma model undergoing anti-PD-1 ab therapy versus IgG isotype control. (n=5). (C) Gr-1 immunohistochemical (IHC) analysis of resected transgenic BRAF$^{V600E}$PTEN$^{-/-}$ melanoma tissues following anti-PD-1 ab therapy versus IgG isotype control. Representative of 3 tumors per group. 40×. Gr-1, red. ctrl, control. (D) Gr-MDSC flow cytometry analysis of resected transgenic BRAF$^{V600E}$PTEN$^{-/-}$ melanoma tissues following anti-PD-1 ab therapy versus IgG isotype control. Gr-MDSCs defined as live$^+$CD45$^+$CD11b$^+$Ly6G$^+$Ly6C$^-$F4/80$^-$ cells. left, representative flow dot plot. right, flow data in graphical form. (n=5). (E) In vivo tumor study of BRAF$^{V600E}$PTEN$^{-/-}$ melanoma genetically silenced for CXCL5. top, representative flow cytometry dot plot of tumor-infiltrating Gr-MDSCs. bottom, flow data in graphical form. In vivo tumor growth curve of CXCL5-silenced BRAF$^{V600E}$PTEN$^{-/-}$ melanoma vs BRAF$^{V600E}$PTEN$^{-/-}$-NTC melanoma control tumors (n=5). KD, knockdown. NTC, non-target control. (F) Anti-PD-1 ab—CXCR2i combination in vivo BRAF$^{V600E}$PTEN$^{-/-}$ melanoma study (n=5). Anti-PD-1 ab (200 µg ip q 3 days), CXCR2i, AZD5069 (100 mg/kg po bid). right, flow cytometry analysis of tumor-infiltrating Gr-MDSCs (top) and live$^+$CD45$^+$CD3$^+$CD8$^+$ T cells (bottom). All data is mean±SEM. *P<0.05. **P<0.005.
Figures 16A, 16B, 16C, 16D, 16E, 16F, 16G, 16H, 16I:
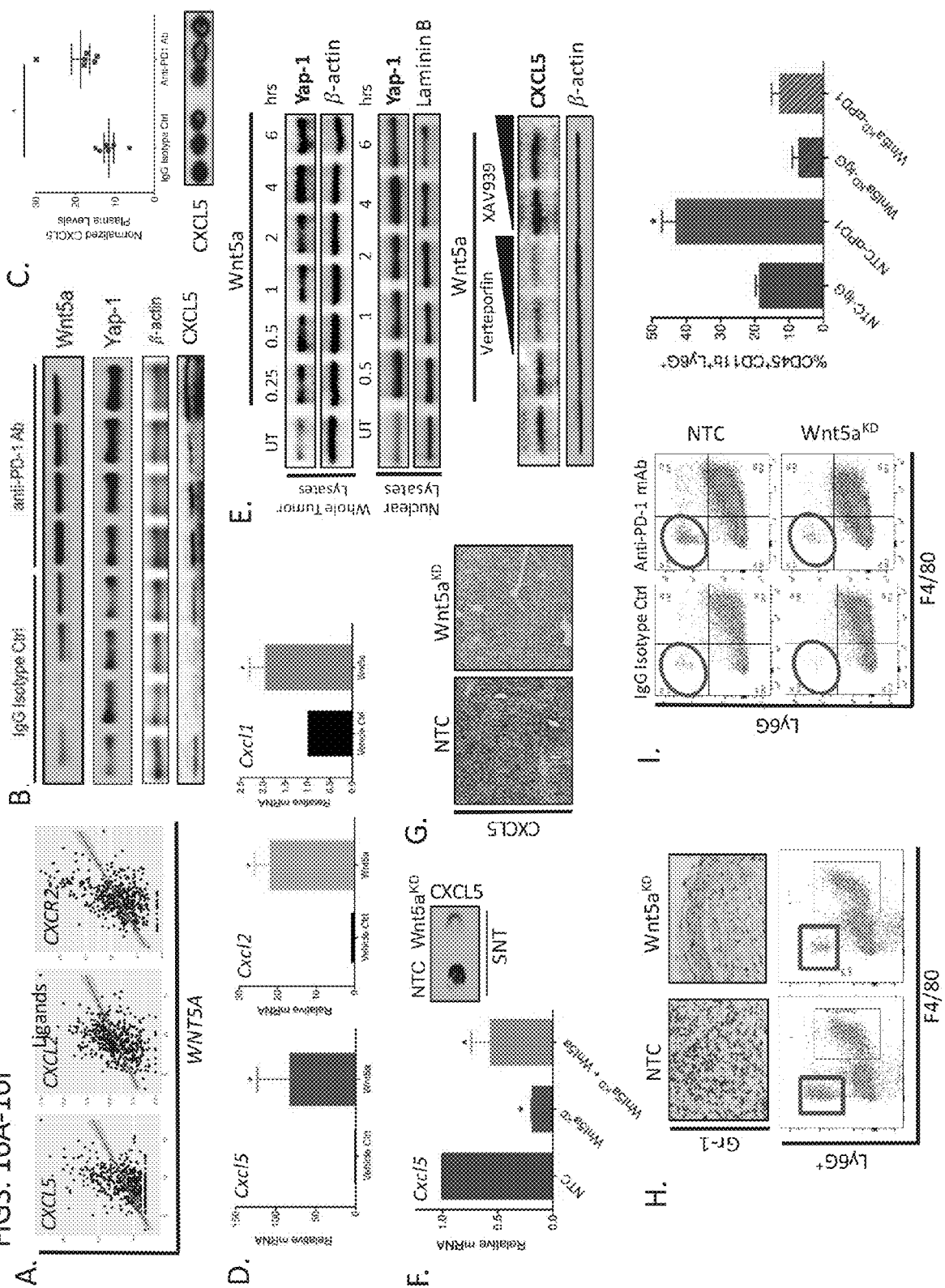
FIGS. 16A-16I demonstrate Wnt5a Induces CXCR2-dependent Chemokine Expression in Response to Anti-PD-1 Ab Immunotherapy. (A) TCGA melanoma database gene expression association analysis of CXCL5, CXCL2, and CXCR2 with WNT5A. (B) Whole tumor tissue Western blot analysis of Wnt5a, nuclear Yap-1, CXCL5 and β-actin (loading control). Representative blot shown (n=3). (C) Plasma CXCL5 ELISA following anti-PD-1 ab therapy vs IgG isotype ctrl therapy in the transgenic BRAF$^{V600E}$PTEN$^{-/-}$ melanoma model (n=5). bottom, plasma CXCL5 dot blot following anti-PD-1 ab therapy vs IgG isotype ctrl therapy in the transgenic BRAF$^{V600E}$PTEN$^{-/-}$ melanoma model. Representative of 3 independent experiments. pseudo-red reflective of density. (D) Qrt-PCR analysis of Cxcl5, Cxcl2, and Cxcl1 in the BRAF$^{V600E}$PTEN$^{-/-}$ melanoma cell line following treatment with recombinant Wnt5a (rWnt5a) vs vehicle ctrl (n=3). (E) Western blot analysis of Yap-1 expression in total cellular lysates (top) and nuclear lysates (middle) following treatment of BRAF$^{V600E}$PTEN$^{-/-}$ melanoma cells with rWnt5a at various time points. β-actin, total lysate loading ctrl. Laminin B, nuclear lysate loading ctrl. (bottom) rWnt5a induction of CXCL5 in the absence and presence of verteporfin (YAP inhibitor) or XAV939 (β-catenin inhibitor). All representative of 3 independent experiments. (F) Qrt-PCR analysis of Cxcl5 in BRAF$^{V600E}$PTEN$^{-/-}$-NTC and Wnt5a-silenced BRAF$^{V600E}$PTEN$^{-/-}$ melanoma cells (BRAF$^{V600E}$PTEN$^{-/-}$-Wnt5a$^{KD}$). right, dot blot analysis of CXCL5 in BRAF$^{V600E}$PTEN$^{-/-}$-NTC and BRAF$^{V600E}$PTEN$^{-/-}$-Wnt5a$^{KD}$ cells (n=3). (G) CXCL5 IHC in BRAF$^{V600E}$PTEN$^{-/-}$-NTC and BRAF$^{V600E}$PTEN$^{-/-}$-Wnt5a$^{KD}$ tumors. Representative of 3 tumors. 10×. (H) (top) Gr-1 IHC of BRAF$^{V600E}$PTEN$^{-/-}$-NTC and BRAF$^{V600E}$PTEN$^{-/-}$-Wnt5a$^{KD}$ tumors. (bottom) Gr-MDSC flow cytometry analysis of BRAF$^{V600E}$PTEN$^{-/-}$-NTC and BRAF$^{V600E}$PTEN$^{-/-}$-Wnt5a$^{KD}$ tumors. (n=3). (I) Gr-MDSC flow cytometry analysis of BRAF$^{V600E}$PTEN$^{-/-}$-NTC and BRAF$^{V600E}$PTEN$^{-/-}$-Wnt5a$^{KD}$ tumors following anti-PD-1 ab therapy vs IgG isotype ctrl (n=5). All data is mean±SEM. *P<0.05. **P<0.005.

As demonstrated in FIGS. 15A-F, granulocytic myeloid-derived suppressor cells (Gr-MDSC) accumulation contributes to tumor progression through Anti-PD-1 Antibody Immunotherapy. Gr-MDSC recruitment accompanies Anti-PD-1 antibody escape. The autochthonous $BRAF^{V600E}PTEN^{-/-}$ melanoma model was used and treated with anti-PD-1 ab therapy versus IgG isotype control. (n=3). Tumor biopsies were collected and underwent RNA isolation and qrt-PCR analysis. FIG. 15 demonstrates an increase in CXCR2 ligands (CXCL1, CXCL2, CLCL3 and CXCL5) in mice treated with anti-PD-1 antibodies. Qrt-PCR analysis of CXCL5, CXCR2, S100a9, and Ly6g (Gr-1) were assayed in serial tumor biopsy specimens harvested from the transgenic $BRAF^{V600E}PTEN^{-/-}$ melanoma model undergoing anti-PD-1 ab therapy versus IgG isotype control. (n=5) as shown in FIG. 15B. All 4 markers are upregulated after Anti-PD-1 therapy. Anti-PD-1 therapy in the mouse model also correlated with an increase in Gr-1.

The increase in Gr-1 expression was also seen by immunohistochemical (IHC) analysis of resected transgenic $BRAF^{V600E}PTEN^{-/-}$ melanoma tissues following anti-PD-1 ab therapy versus IgG isotype control (FIG. 15C). Gr-MDSC cells were also detected by flow cytometry (Gr-MDSC cells were considered live$^+$CD45$^+$CD11b$^+$Ly6G$^+$Ly6C$^+$F4/80, FIG. 15D)$^+$ In vivo tumor study of $BRAF^{V600E}PTEN^{-/-}$ melanoma genetically silenced for CXCL5 showed loss of the tumor-infiltrating Gr-MDSCs in CXCL5-mice. Anti-PD-1 ab—CXCR2 inhibitor combination in vivo $BRAF^{V600E}PTEN^{-/-}$ melanoma study (n=5). Anti-PD-1 ab (200 μg ip q 3 days), CXCR2 inhibitor, AZD5069 (100 mg/kg po bid, commercially available, AdooQ Bioscience) showed an increase in tumor cell growth.

Wnt5a promotes CXCR2-dependent chemokine upregulation in response to anti-PD-1 therapy as demonstrated in FIG. 15. TCGA melanoma database gene expression association analysis of CXCL5, CXCL2, and CXCR2 with WNT5A demonstrated that CXCL5, CXCL2, and CXCR2 are markers are upregulated after treatment with anti-PD1 therapy (FIG. 15A-C) Qrt-PCR analysis of Cxcl5, Cxcl2, and Cxcl1 in the $BRAF^{V600E}PTEN^{-/-}$ melanoma cell line following treatment with recombinant Wnt5a (rWnt5a) vs vehicle ctrl (n=3) showed increased expression of Cxcl5, Cxcl2, and Cxcl1 (FIGS. 15D-E). FIG. 15F shows Qrt-PCR analysis of Cxcl5 in $BRAF^{V600E}PTEN^{-/-}$-NTC and Wnt5a-silenced $BRAF^{V600E}PTEN^{-/-}$ melanoma cells ($BRAF^{V600E}PTEN^{-/-}$-Wnt5a$^{KD}$). right, dot blot analysis of CXCL5 in $BRAF^{V600E}PTEN^{-/-}$-NTC and $BRAF^{V600E}PTEN^{-/-}$-Wnt5a$^{KD}$ cells (n=3). CXCL5 expression is upregulated in NTC tumors compared to Wnt5a knock down tumors (FIG. 15G). IHC in $BRAF^{V600E}PTEN^{-/-}$-NTC and $BRAF^{V600E}PTEN^{-/-}$-Wnt5a$^{KD}$ tumors. Representative of 3 tumors. 10×. Gr-1 and Ly6G are also biomarkers associated with Wnt5a expression in tumors (FIG. 15H) and show increased expression after anti-PD-1 therapy. (FIG. 15I).

Figures 17A, 17B, 17C, 17D, 17E, 17F, 17G, 17H, 17I, 17J:
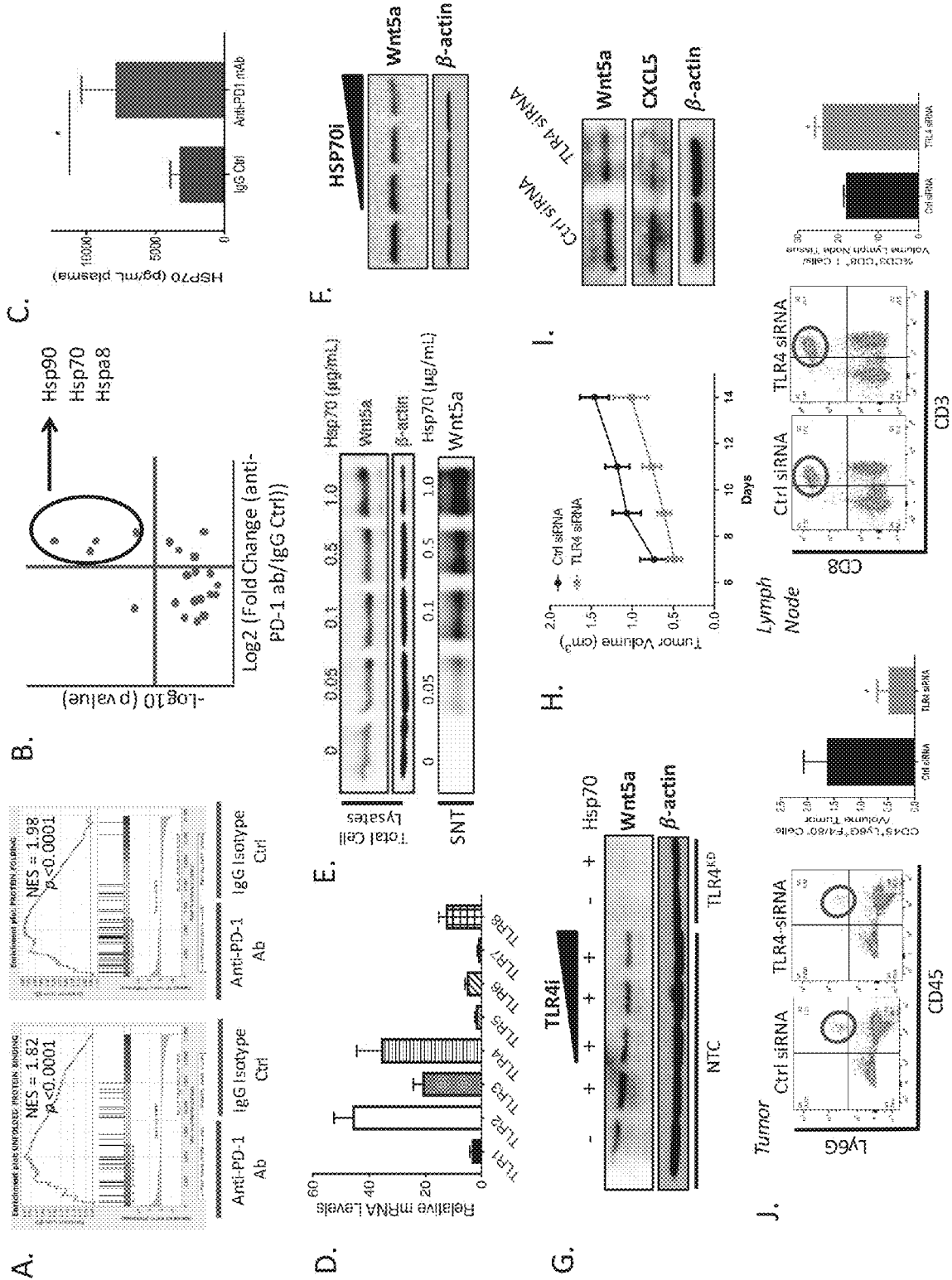
FIGS. 17A-17J demonstrate HSP70-TLR4 Induces Wnt5a Expression in Response to Anti-PD-1 Ab Immunotherapy. (A) GSEA analysis of stress response pathways in autochthonous BRAF$^{V600E}$PTEN$^{-/-}$ melanoma model following anti-PD-1 ab therapy vs IgG isotype ctrl. NES, normalized enrichment analysis. (B) SILAC-AHA LC/MS-MS secretome analysis of resected autochthonous BRAF$^{V600E}$PTEN$^{-/-}$ melanoma tissues following anti-PD-1 ab therapy vs IgG isotype ctrl (n=3). (C) Plasma HSP70 ELISA analysis following anti-PD-1 vs IgG isotype ctrl treatment of autochthonous BRAF$^{V600E}$PTEN$^{-/-}$ melanoma mice (n=5). (D) Qrt-PCR analysis of TLR expression analysis of BRAF$^{V600E}$PTEN$^{-/-}$ melanoma cells. Data normalized to TLR9 expression levels (n=3). (E) Treatment of BRAF$^{V600E}$PTEN$^{-/-}$ melanoma cells with titrated concentrations of recombinant HSP70 (rHSP70) followed by Wnt5a Western blot analysis of total cell lysates (top) and supernatant (SNT) (bottom). Representative of 2 independent experiments. (F) Treatment of BRAF$^{V600E}$PTEN$^{-/-}$ melanoma cells with titrated concentrations of HSP70 inhibitor (HSP70i). Representative of 2 independent experiments. (G) Treatment of BRAF$^{V600E}$PTEN$^{-/-}$-NTC cells with rHSP70 in the absence and presence of increasing concentrations of a TLR4 inhibitor (TLR4i) and treatment of TLR4-silenced BRAF$^{V600E}$PTEN$^{-/-}$ melanoma cells (TLR4$^{KD}$) with HSP70 followed by Wnt5a Western blot. Representative of 3 independent experiments. (H) BRAF$^{V600E}$PTEN$^{-/-}$ melanoma tumor growth curve following TLR4 siRNA vs Ctrl siRNA treatment (n=5). (I) Whole tissue Western blot analysis of Wnt5a, CXCL5, and β-actin in TLR4 siRNA-treated and Ctrl siRNA-treated BRAF$^{V600E}$PTEN$^{-/-}$ melanomas. Representative of 2 independent experiments. (J) left, Gr-MDSC flow cytometry analysis of TLR4 siRNA-treated and Ctrl siRNA-treated BRAF$^{V600E}$PTEN$^{-/-}$ melanomas (n=4). right, CD8$^+$ T cell flow cytometry analysis of TLR4 siRNA-treated and Ctrl siRNA-treated BRAF$^{V600E}$PTEN$^{-/-}$ melanomas (n=4). All data is mean±SEM. *P<0.05.
Figures 18A, 18B, 18C, 18D, 18E, 18F:
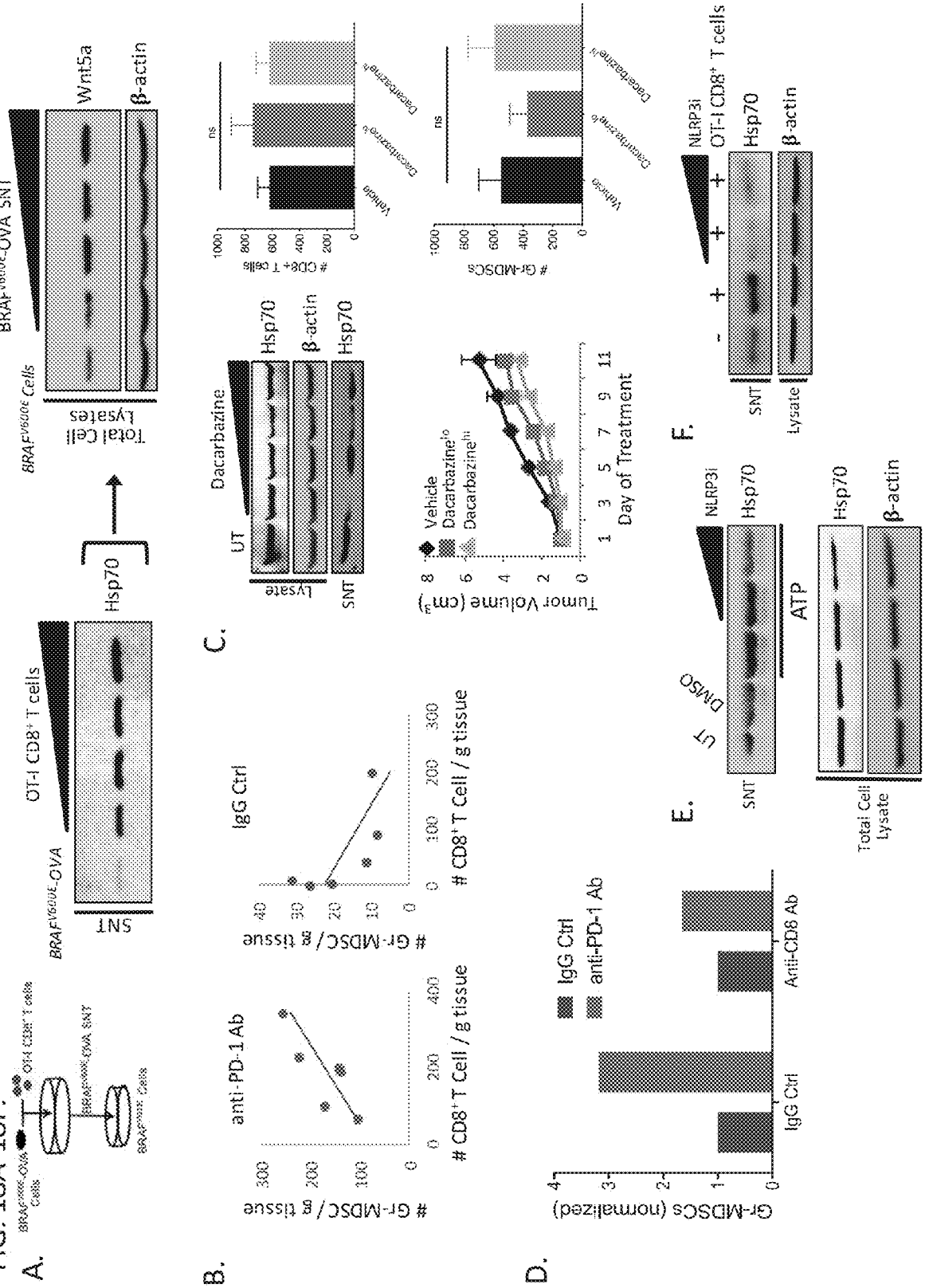
FIGS. 18A-18F demonstrate CD8$^+$ T Cells Induce Tumor HSP70 Release in a NLRP3-dependent Manner. (A) left, Co-culture of OT-I CD8$^+$ T cells with OVA-expressing BRAF$^{V600E}$PTEN$^{-/-}$ melanoma cells followed by HSP70 Western blot analysis of isolated supernatant (SNT). right, Harvested SNT co-incubated at increasing concentrations with wild type BRAF$^{V600E}$PTEN$^{-/-}$ melanoma cells followed by Wnt5a Western blot analysis. (B) Gr-MDSC and CD8⁺ T cell flow cytometry analysis of resected autochthonous BRAF$^{V600E}$PTEN$^{-/-}$ melanoma tissues following anti-PD-1 ab and IgG isotype ctrl therapy. Data expressed per gram of tumor tissue (n=6). (C). top left, HSP70 and β-actin Western blot following treatment of BRAF$^{V600E}$PTEN$^{-/-}$ melanoma cells with increasing concentrations of dacarbazine. Representative of 3 independent experiments. bottom left, Tumor growth curve of syngeneic BRAF$^{V600E}$PTEN$^{-/-}$ melanomas following vehicle control or low (lo) vs high (hi) dose dacarbazine therapy (n=5). top right, CD8⁺ T cell flow cytometry analysis of BRAF$^{V600E}$PTEN$^{-/-}$ melanomas following vehicle control or low (lo) vs high (hi) dose dacarbazine therapy (n=5). ns, non-significant. bottom right, Gr-MDSC cell flow cytometry analysis of BRAF$^{V600E}$PTEN$^{-/-}$ melanomas following vehicle control or low (lo) vs high (hi) dose dacarbazine therapy (n=5). (D) Tumor-infiltrating Gr-MDSC flow cytometry analysis of autochthonous BRAF$^{V600E}$PTEN$^{-/-}$ melanoma mice following anti-PD-1 ab vs IgG isotype ctrl therapy in the absence and presence of anti-CD8 antibody. Data normalized to IgG ctrl-treated tumors (n=5). (E) HSP70 Western blot analysis of SNT and tumor cell lysates following ATP stimulation of BRAF$^{V600E}$PTEN$^{-/-}$ melanoma cells in the absence and presence of NLRP3 inhibitor (NLRP3i) treatment. Representative of 3 independent experiments. (F) HSP70 Western blot following co-incubation of OT-1 CD8⁺ T cells and OVA-expressing BRAF$^{V600E}$PTEN$^{-/-}$ melanoma cells in the absence and presence of increasing concentrations of NLRP3i. Representative of 3 independent experiments. All data is mean±SEM.

HSP70-TLR4 Induces Wnt5a Expression in Response to Anti-PD-1 Ab Immunotherapy as demonstrated in FIG. 17. Anti-PD-1 therapy results in an antibody mediated Gr-MDSC recruitment which is dependent on HSP70. Thus, HSP70 is another marker associated with anti-PD-1 therapy resistance and as a marker for wnt-5a dependent tumors. Further, FIG. 18 demonstrates CD8+ T cells induce NLRP3 inflammasome-dependent HSP70 release in response to anti-PD-1 therapy.

Figures 19A, 19B, 19C, 19D, 19E, 19F, 19G, 19H, 19I:
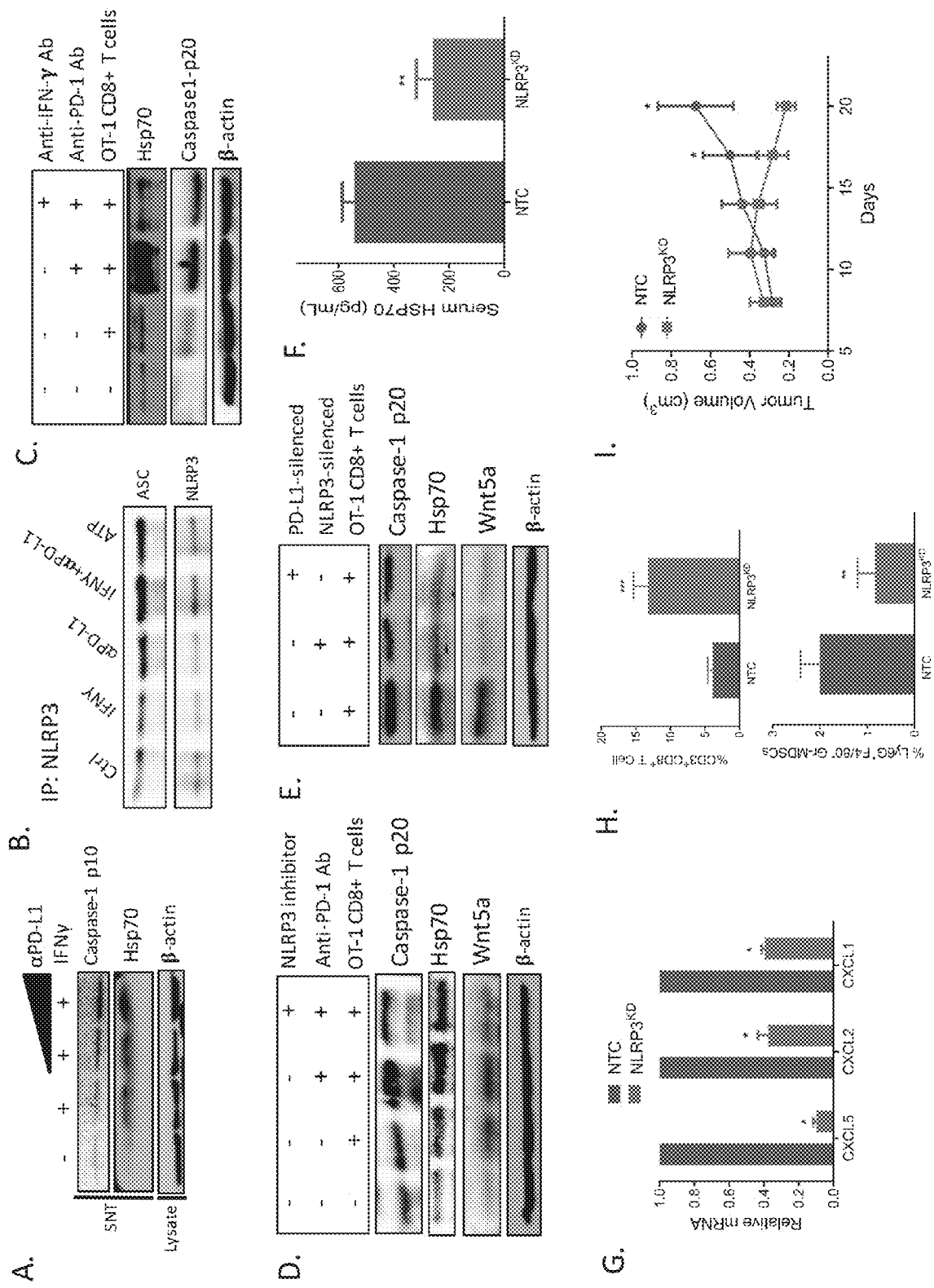
FIGS. 19A-19I demonstrate CD8⁺ T cells Trigger a PD-L1:NLRP3 Signaling Pathway to Drive Gr-MDSC Recruitment to the Tumor. (A) Caspase-1 p10 Western blot analysis as a surrogate for NLRP3 inflammasome activation following treatment of BRAF$^{V600E}$PTEN$^{-/-}$ melanoma cells with IFN-γ in the absence and presence of increasing concentrations of anti-PD-L1 ab. HSP70 and β-actin Western blots also performed. Representative of 3 independent experiments. (B) Immunoprecipitation of NLRP3 following treatment of BRAF$^{V600E}$PTEN$^{-/-}$ melanoma cells with IFN-γ, anti-PD-L1, or both followed by ASC and NLRP3 Western blot analysis. Representative of 2 independent experiments. (C) Co-culture of OT-I CD8⁺ T cells with OVA-expressing BRAF$^{V600E}$PTEN$^{-/-}$ melanoma cells followed by HSP70 and Caspase-1 p20 Western blot analysis in the absence and presence of anti-PD-1 ab alone or anti-PD-1 ab+anti-IFN-γ blocking ab. Representative of 3 independent experiments. (D) Co-culture of OT-I CD8⁺ T cells with OVA-expressing BRAF$^{V600E}$PTEN$^{-/-}$ melanoma cells followed by Caspase-1 p20, HSP70, and Wnt5a Western blot analysis in the absence and presence of anti-PD-1 ab alone or anti-PD-1 ab+NLRP3i. Representative of 3 independent experiments. (E) Caspase-1 p20, HSP70, and Wnt5a Western blot analysis of OVA-expressing BRAF$^{V600E}$PTEN$^{-/-}$ melanoma cells following co-culture with OT-I CD8⁺ T cells after genetically silencing either NLRP3 or PD-L1. Representative of 3 independent experiments. (F) Plasma HSP70 ELISA analysis following growth of BRAF$^{V600E}$PTEN$^{-/-}$-NTC or NLRP3-silenced BRAF$^{V600E}$PTEN$^{-/-}$ melanomas (n=5). KD, knockdown. (G) Qrt-PCR analysis of CXCR2-dependent chemokine expression in BRAF$^{V600E}$PTEN$^{-/-}$-NTC and BRAF$^{V600E}$PTEN$^{-/-}$-NLRP3$^{KD}$ melanomas (n=3). (H) top, CD8⁺ T cell flow cytometry analysis of resected BRAF$^{V600E}$PTEN$^{-/-}$-NTC and BRAF$^{V600E}$PTEN$^{-/-}$-NLRP3$^{KD}$ melanomas (n=5). bottom, Gr-MDSC flow cytometry analysis of resected BRAF$^{V600E}$PTEN$^{-/-}$-NTC and BRAF$^{V600E}$PTEN$^{-/-}$-NLRP3$^{KD}$ melanomas (n=5). (I) Tumor growth curve of BRAF$^{V600E}$PTEN$^{-/-}$-NTC and BRAF$^{V600E}$PTEN$^{-/-}$-NLRP3$^{KD}$ melanomas (n=5). All data is mean±SEM. *P<0.05. P<0.005. *P<0.0005.

These CD8$^+$ T Cells Induce Tumor HSP70 Release in a NLRP3-dependent Manner as demonstrated in FIG. 19. CD8$^+$ T cells Trigger a PD-L1:NLRP3 Signaling Pathway to Drive Gr-MDSC Recruitment to the Tumor as demonstrated in FIG. 19.

Figures 20A, 20B, 20C:
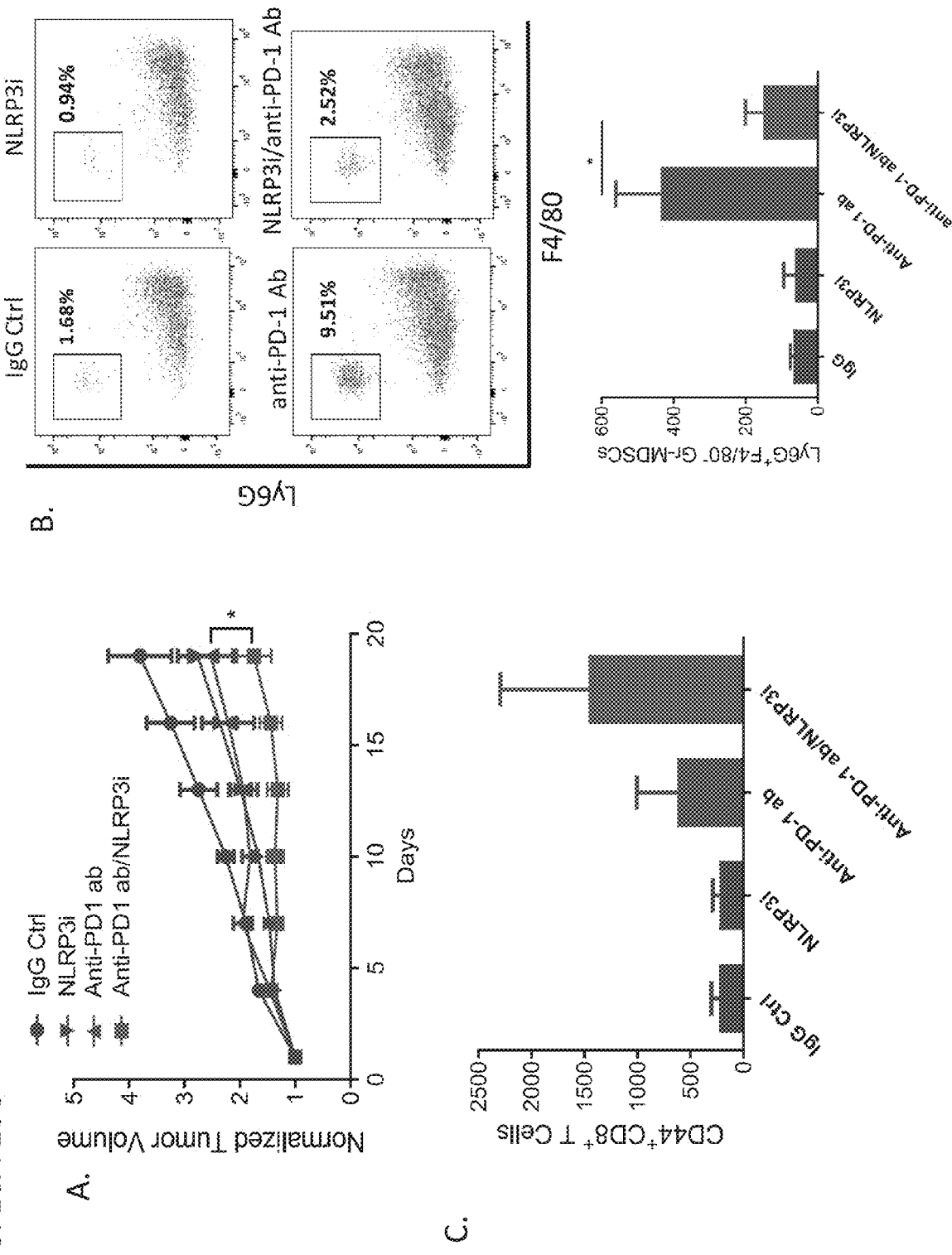
FIGS. 20A-20C demonstrate pharmacologic Inhibition of NLRP3 Suppresses Gr-MDSC Recruitment and Enhances the Efficacy of Anti-PD-1 Ab Immunotherapy. (A) Treatment of syngeneic BRAF$^{V600E}$PTEN$^{-/-}$ melanomas with IgG isotype control ab (200 µg ip every 3 days), NLRP3i (MCC950 10 µg ip every 3 days), anti-PD-1 ab (200 µg ip every 3 days), or both NLRP3i and anti-PD-1 ab combination therapy (n=8). (B) Gr-MDSC flow cytometry analysis of resected BRAF$^{V600E}$PTEN$^{-/-}$ melanomas following treatment with IgG isotype control ab, NLRP3i, anti-PD-1 ab, or both NLRP3i and anti-PD-1 ab combination therapy (n=4). top, representative flow cytometry dot plot. (C) CD8⁺ T cell flow cytometry analysis of resected BRAF$^{V600E}$PTEN$^{-/-}$ melanomas following treatment with IgG isotype control ab, NLRP3i, anti-PD-1 ab, or both NLRP3i and anti-PD-1 ab combination therapy (n=4). All data is mean±SEM. *P<0.05.
Figures 21A, 21B, 21C:
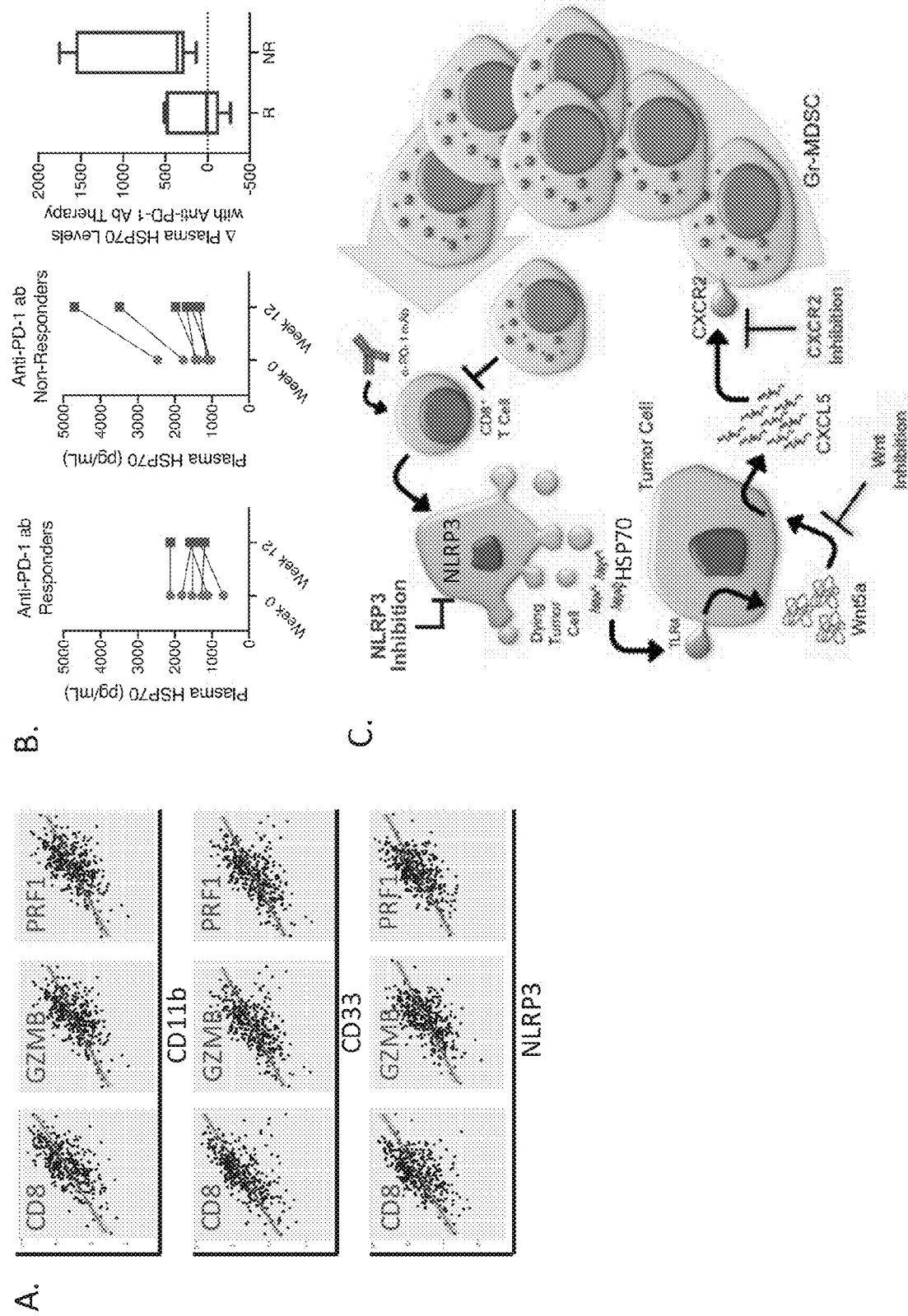
FIGS. 21A-21C show the clinical Significance of the PD-L1:NLRP3:HSP70 Gr-MDSC Adaptive Recruitment Pathway. (A) Cytolytic T cell markers correlated with CD11B, CD33, and NLRP3 gene expression in the melanoma TCGA database. (B) Plasma HSP70 ELISA at week 0 and week 12 in advanced melanoma patients undergoing anti-PD-1 ab immunotherapy. left, responders. middle, non-responders. right, change in HSP70 plasma levels following anti-PD-1 ab immunotherapy in responding (R) and non-responding (NR) advanced melanoma patients. Response based on week 12 CT imaging and RECIST1.1 response criteria. (C) Schematic figure illustrating the CD8⁺ T cell: PD-L1:NLRP3:HSP70:Wnt5a:CXCL5:Gr-MDSC adaptive resistance pathway induced by anti-PD-1 ab immunotherapy.

Pharmacologic Inhibition of NLRP3 Suppresses Gr-MDSC Recruitment and Enhances the Efficacy of Anti-PD-1 which is demonstrated in FIG. 20. As depicted in FIG. 21A, NLRP3 inhibition can be combined with a Wnt inhibitor (e.g. PD-1 inhibitor) to augment the anti-tumor effect of the PD-1 inhibitor therapy. Treatment with the combination of an anti-PD-1 antibody and an inhibitor of NLR family pyrin domain containing 3 (NLRP3) results in an increase in reduction of tumor cell volume i (FIG. 20A) and in increase in the number of CD8+ T cells (FIG. 20C) in the melanoma model. Treatment with both anti-PD-1 and an anti-NLRP3 antibody (inhibitor of NLRP3) results in a reduction in the number of Ly6G+ Gr-MDSCsD (FIG. 20D), correlating with the lower tumor volume, demonstrating inhibition of NLRP3 suppresses Gr-MDSC Recruitment and enhances the efficacy of anti-PD-1.

FIG. 21 depicts the clinical Significance of the PD-L1:NLRP3:HSP70 Gr-MDSC Adaptive Recruitment Pathway. Cytolytic T cell markers correlated with CD11B, CD33, and NLRP3 gene expression in the melanoma TCGA database (FIG. 21A). FIG. 21B demonstrates an increase in the plasma concentration of HSP70 in anti-PD-1 treated advanced melanoma patients, showing that there is an increase expression of HSP70 associated with non-responsiveness to anti-PD-1 therapy. FIG. 21C is a schematic figure illustrating the CD8$^+$ T cell:PD-L1:NLRP3:HSP70:Wnt5a:CXCL5:Gr-MDSC adaptive resistance pathway induced by anti-PD-1 ab immunotherapy, pointing out the synergistic pathways that maybe combined with anti-PD1 therapy to improve the anti-tumor immune response to immunotherapies, specifically PD-1 immunotherapy.

The invention claimed is:

1. A method of selecting a subject having a wnt-β-catenin-mediated cancer comprising: (a) obtaining a biological sample from the subject; (b) detecting in the biological sample derived from the subject three or more biomarkers associated with wnt-β-catenin-mediated cancer selected from the group consisting of wnt5a, CXCL2, CXCL5, CXCR2, HSP70, S100A8/S100A9, YAP1, NLRP3 and combinations thereof; (c) selecting a subject having wnt-β-catenin-mediated cancer, wherein detection of the three or more biomarkers in an amount greater than that of the control sample indicates the presence of a wnt-β-catenin-mediated cancer in the subject and (d) administering to the subject selected in step (c) an anti-wnt-β-catenin-mediated cancer therapy if a wnt-β-catenin-mediated cancer is detected.

2. The method of claim 1, wherein the anti-wnt-β-catenin-mediated cancer therapy is selected from the group consisting of PORCN inhibitors, PAK4 inhibitors, Fzd receptor antagonistic antibodies, Wnt ligand traps and combinations thereof.

3. The method of claim 1, wherein the anti-wnt-β-catenin-mediated cancer therapy is administered in combination with an anti-PD-1 immunotherapy.

4. The method of claim 3, wherein the anti-PD1 immunotherapy is an anti-PD1 antibody capable of blocking PD-1 binding to a cell.

5. The method of claim 1, wherein the biological sample is selected from the group consisting of tissues, cells, biopsies, blood, lymph, serum, plasma, urine, saliva, mucus, and tears.

6. The method of claim 5, wherein the sample comprises a biopsy.

7. The method of claim 1, wherein the wnt-β-catenin-mediated cancer comprises melanoma.

8. A method of selecting a subject having the presence of an immunotherapy-resistant wnt-β-catenin-mediated cancer comprising: (a) obtaining a biological sample from a subject; (b) detecting three or more biomarkers that are associated with an immunotherapy resistant wnt-β-catenin-mediated cancer in the biological sample selected from the group consisting of wnt5a, CXCL2, CXCL5, CXCR2, HSP70, S100A8/S100A9, YAP1, NLRP3 and combinations thereof; (c) selecting the patient expressing three or more biomarkers in the sample in an amount greater than that of the control as a subject having an immunotherapy-resistant wnt-β-catenin-mediated cancer; and (d) administering to the patient selected in step (c) an anti-wnt-β-catenin signaling pathway inhibitor and an anti-wnt-β-catenin-mediated cancer immunotherapy if an immunotherapy-resistant wnt-β-catenin-mediated cancer is detected.

9. The method of claim 8, wherein the anti-wnt-β-catenin-mediated cancer immunotherapy is an anti-PD-1 immunotherapy.

10. The method as in claim 9, wherein the anti-PD1 immunotherapy is an anti-PD1 antibody capable of blocking PD-1 binding to a cell.

11. The method of claim 8, wherein the biological sample is selected from the group consisting of tissues, cells, biopsies, blood, lymph, serum, plasma, urine, saliva, mucus, and tears.

12. The method of claim 11, wherein the sample comprises a biopsy.

13. The method of claim 8, wherein the wnt-β-catenin-mediated cancer is a cancer selected from the group consisting of melanoma, metastatic melanoma, non-small cell lung cancer, renal cell carcinoma, Hodgkin Lymphoma, squamous cell carcinoma of the head and neck, urothelial carcinoma, colorectal cancer, pancreatic cancer or hepatocellular carcinoma.

14. The method of claim 8, wherein the cancer is melanoma.

15. A method of treating a subject having or suspected of having an immunotherapy resistant tumor, the method comprising: (a) detecting the presence of a wnt-β-catenin-mediated cancer in a subject comprising detecting in a biological sample derived from the subject three or more biomarkers associated with wnt-β-catenin-mediated cancer selected from the group consisting of wnt5a, CXCL2, CXCL5, CXCR2, HSP70, S100A8/S100A9, YAP1, NLRP3 and combinations thereof,
  (b) selecting the subject having detection of the three or more biomarkers as a subject with a immunotherapy resistant tumor, and
  (c) administering a therapeutically effective amount of one or more anti-wnt-β-catenin-mediated cancer immunotherapy to the selected subject having an immunotherapy resistant tumor.

16. The method of claim 15, wherein the immunotherapy is an anti-PD-1 immunotherapy.

17. The method of claim 15, the method of step (a) comprising the steps of: (i) obtaining a biological sample from the subject; (ii) determining the expression level of three or more biomarkers that are associated with a wnt-β-catenin-mediated cancer selected from the group consisting of wnt5a, CXCL2, CXCL5, CXCR2, HSP70, S100A8/S100A9, YAP1, and NLRP3 and combinations thereof in the biological sample; and (iii) detecting the expression level of the three or more biomarkers in a control, wherein the presence of three or more of the biomarkers in the sample in an amount greater than that of the control indicates the presence of a immunotherapy resistant cancer.

\* \* \* \* \*

UNITED STATES PATENT AND TRADEMARK OFFICE
CERTIFICATE OF CORRECTION

PATENT NO. : 11,643,691 B2
APPLICATION NO. : 16/384710
DATED : May 9, 2023
INVENTOR(S) : Brent Hanks et al.

It is certified that error appears in the above-identified patent and that said Letters Patent is hereby corrected as shown below:

In the Specification

Column 4, Line 6, "PJk1" should be --Pfk1--.

Column 4, Line 46, "1 g/ml" should be --1 µg/ml--.

Column 4, Line 52, "21H" should be --2H--.

Column 4, Line 62, "$CD^{3+}CD^{+}$" should be --$CD^{3+}CD^{8+}$--.

Column 6, Line 18, "CD1 c" should be --CD11c--.

Column 6, Line 43, "Wnt/p-catenin" should be --Wnt/β-catenin--.

Column 14, Line 62, "Wnt-3-catenin" should be --Wnt-β-catenin--.

Column 18, Line 61, "wnt-p-catenin" should be --wnt-β-catenin--.

Column 23, Line 57, "500p 1" should be --500µl--.

Column 26, Line 63, "3-catenin" should be --β-catenin--.

Signed and Sealed this
Twenty-first Day of May, 2024

Katherine Kelly Vidal
*Director of the United States Patent and Trademark Office*